United States Patent
Selness et al.

(10) Patent No.: US 9,365,546 B2
(45) Date of Patent: *Jun. 14, 2016

(54) SUBSTITUTED PYRIDINONE-PYRIDINYL COMPOUNDS

(71) Applicant: CONFLUENCE LIFE SCIENCES INC., St. Louis, MO (US)

(72) Inventors: Shaun R. Selness, Chesterfield, MO (US); Joseph B. Monahan, St. Louis, MO (US); John F. Schindler, Chesterfield, MO (US); Balekudru Devadas, Chesterfield, MO (US)

(73) Assignee: CONFLUENCE LIFE SCIENCES INC., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/149,659

(22) Filed: Jan. 7, 2014

(65) Prior Publication Data

US 2014/0171449 A1 Jun. 19, 2014

Related U.S. Application Data

(63) Continuation of application No. 13/312,924, filed on Dec. 6, 2011, now abandoned.

(60) Provisional application No. 61/420,074, filed on Dec. 6, 2010.

(51) Int. Cl.
| | |
|---|---|
| C07D 401/14 | (2006.01) |
| A61K 31/4412 | (2006.01) |
| C07D 413/14 | (2006.01) |
| C07D 409/14 | (2006.01) |
| C07D 417/14 | (2006.01) |
| A61K 45/06 | (2006.01) |

(52) U.S. Cl.
CPC ............ *C07D 401/14* (2013.01); *A61K 45/06* (2013.01); *C07D 409/14* (2013.01); *C07D 413/14* (2013.01); *C07D 417/14* (2013.01)

(58) Field of Classification Search
CPC .................. C07D 401/14; A61K 31/4412
USPC .................... 544/333; 546/257; 514/256, 332
See application file for complete search history.

(56) References Cited

U.S. PATENT DOCUMENTS

| | | | |
|---|---|---|---|
| 7,067,540 B2 | 6/2006 | Devadas et al. | 514/348 |
| 7,314,752 B2 | 1/2008 | Kritzman et al. | 435/288.7 |
| 7,345,054 B2 | 3/2008 | Hale et al. | 514/300 |
| 8,221,753 B2 | 7/2012 | Theuer et al. | 424/133.1 |
| 2005/0176775 A1 | 8/2005 | Devadas et al. | 514/340 |
| 2007/0167621 A1 | 7/2007 | Durley et al. | 544/60 |
| 2008/0085884 A1* | 4/2008 | Armour et al. | 514/210.2 |
| 2009/0030017 A1 | 1/2009 | Hanada et al. | 514/256 |

FOREIGN PATENT DOCUMENTS

| | | | |
|---|---|---|---|
| CN | 1646125 | 7/2005 | ......... A61K 31/4412 |
| EP | 1447401 | 8/2004 | ........... C07D 211/76 |
| EP | 1741702 | 1/2007 | ........... C07D 211/82 |
| JP | 2005-255675 | 9/2005 | ......... A61K 31/4418 |
| WO | WO 00/17175 | 3/2000 | ........... C07D 277/48 |
| WO | WO 00/71535 | 11/2000 | ........... C07D 401/06 |
| WO | WO 02/42292 | 5/2002 | ........... C07D 401/06 |
| WO | WO 03/068230 | 8/2003 | ......... A61K 31/4412 |
| WO | WO 2004/014859 | 2/2004 | ........... C07D 213/00 |
| WO | WO 2004/024078 | 3/2004 | |
| WO | WO 2004/087677 | 10/2004 | ........... C07D 239/00 |
| WO | WO 2005/018557 | 3/2005 | |
| WO | WO 2005/077050 | 8/2005 | |
| WO | WO 2006/109876 | 10/2006 | ........... A61K 31/444 |
| WO | WO 2007/006591 | 1/2007 | ........... C07D 213/64 |
| WO | WO 2007/141200 | 12/2007 | ........... C07D 213/69 |
| WO | WO 2008/062905 | 5/2008 | ........... C07D 413/10 |
| WO | WO 2008/073306 | 6/2008 | ........... C07D 213/75 |
| WO | WO 2007/081901 | 7/2008 | ........... A61K 31/513 |

(Continued)

OTHER PUBLICATIONS

Boehm et al., New Inhibitors of p38 kinase, Expert Opinion in Therapeutic Patents, 10(1), pp. 25-37, (2000).*

(Continued)

*Primary Examiner* — Deepak Rao
(74) *Attorney, Agent, or Firm* — Harness, Dickey & Pierce, P.L.C.

(57) ABSTRACT

The present disclosure provides pyridinone-pyridinyl compounds useful in the treatment of p38 kinase mediated diseases, such as lymphoma and auto-inflammatory disease, having the structure of Formula (I):

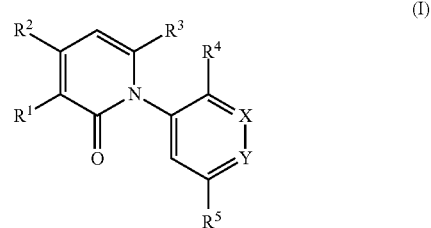

wherein $R^1$, $R^2$, $R^3$, $R^4$, $R^5$, X and Y are as defined in the detailed description; pharmaceutical compositions comprising at least one of the compounds; and methods for treating p38 kinase mediated diseases using the compound.

28 Claims, No Drawings

(56) References Cited

FOREIGN PATENT DOCUMENTS

| WO | WO 2008/153942 | 12/2008 | ............. A01N 43/54 |
|----|----|----|----|
| WO | WO 2009/012275 | 1/2009 | ........... C07D 401/12 |
| WO | WO 2009/012277 | 1/2009 | ........... C07D 401/12 |
| WO | WO 2009/156484 | 12/2009 | ........... C07D 213/81 |
| WO | WO 2011/003007 | 1/2011 | ............. A61K 31/50 |
| WO | WO 2011/003012 | 1/2011 | ............. A61K 31/50 |
| WO | WO 2011/003021 | 1/2011 | ............. A61K 31/50 |

OTHER PUBLICATIONS

Dodeller et al., The p38 mitogen-activated protein kinase signalling cascade in CD4 T cells, Arthritis Research & Therapy, vol. 8, No. 2, (2006). Online at http://arthritis-research.com/content/8/2/205.*

Gura et al., Systems for identifying new drugs are often faulty, Science, 278:1041-1042, 1997.*

Johnson et al., Relationships between drug activity in NCI preclinical in vitro and in vivo models and early clinical trials, British Journal of Cancer, 84(10):1424-1431, 2001.*

Pearce et al., Failure modes in anticancer drug discovery and development, Cancer Drug Design and Discovery Edited by Stephen Neidle, Chapter 18, pp. 424-435 (2008).*

Simone, Oncology: Introduction, Cecil Textbook of Medicine, 20th Edition, vol. 1, pp. 1004-1010, 1996.*

Chinese Office Action dated Jun. 6, 2014 in Chinese Application No. 201180066860.X with English translation.

Burnette, BL. et al., (2009) "SD0006: a potent, selective and orally available inhibitor of p38 kinase" Pharmacology 84(1): 42-60.

Davidson, W. et al., (2004) "Discovery and characterization of a substrate selective p38alpha inhibitor" Biochemistry 43: 11658-71.

Deady, L. et al., (1998) "Studies on the synthesis of benzimidazo[2,1-a]isoquinolines" Australian Journal of Chemistry 51(10): 941-45.

Kato, T. et al., (1964) "Ketene and its derivatives. VIII. Reactions of diketene with amino heterocycles." *Yakugaku Zasshi* 34(12): 1201-5.

Kato, T. et al., (1964) "Studies on Ketene and its Derivatives. VI. Reaction of diketene with aminopyridines and their N-oxides." *Chem. Pharm. Bull.* 12(8): 910-16.

Kato, T. et al., (1972) "Studies on Ketene and Its Derivatives. XLVI. Mass spectrometric studies of 3-Acetyl-4-hydroxy-6-methyl-l-pyridyl-2-pyridones and N-Pyridyl-2, 6-dimethyl-4-pyrone-3-carboxamides." *Chem. Pharm. Bull.* 20(1): 133-41.

Sherlock, M. et al., (1988) "Antiallergy agents. 1. Substituted 1,8-naphthyridin-2(1H)-ones as inhibitors of SRS-A release." *J. Med. Chem.* 31(11): 2108-21.

Tonkiha, N. et al., (2005) "Syntheses of 7,8-dihydro-9H-pyrido[3,2-b][1,4]diazepin-8-ones and 2,3-dihydro-1H-1,5-benzodiazepines in reactions of 4-hydroxycoumarin and 4-hydroxy-6-methyl-2H-pyran-2-one with aromatic o-diamines." *Latvijas Kimijas Zurnals* 1: 51-60.

Hu, E., et al., "Discovery of Aryl Aminoquinazoline Pyridones as Potent, Selective, and Orally Efficacious Inhibitors of Receptor Tyrosine Kinase e-Kit", J. Med. Chem., 51, 3065-3068, 2008.

Supplemental Search Report of 11847595.3 dated Apr. 2, 2014.

* cited by examiner

SUBSTITUTED PYRIDINONE-PYRIDINYL COMPOUNDS

CROSS-REFERENCE TO RELATED APPLICATIONS

This application is a continuation application of U.S. application Ser. No. 13/312,924 filed on Dec. 6, 2011 which claims the benefit and priority to U.S. Provisional Application No. 61/420,074, filed on Dec. 6, 2010. The entire disclosure of the above application is incorporated herein by reference.

FIELD

The present disclosure generally relates to a compound having enzyme inhibitory activity, pharmaceutical compositions comprising the compound, and methods useful for treating diseases. More specifically, the present disclosure relates to a class of bi-pyridinone compounds, pharmaceutical compositions comprising the compound, and methods useful for treating p38 kinase mediated diseases.

BACKGROUND

Mitogen-activated protein kinases (MAPK) are a conserved family of enzymes that relay and propagate external stimuli, using phosphorylation cascades to generate a coordinated cellular response to the environment. The MAPK are proline-directed serine/threonine-specific protein kinases that regulate cellular activities, such as gene expression, mitosis, differentiation, and cell survival/apoptosis. To date, 4 distinct classes of mammalian MAPK have been identified: the extracellular signaling kinases (ERK1 and 2), the c-jun N-terminal kinase-1 (JNK1-3), the p38 MAPK (p38α, β, γ, and δ), and ERK5. The MAPK are activated by the dual phosphorylation of Thr and Tyr residues within a TXY activation motif by coordinated dual-specificity MAPKK, where X is Glu, Pro, and Gly in ERK, JNK, and p38 MAPK, respectively. MAPK are 60-70% identical to each other, yet differ in their activation loop sequences and sizes. The activation loop is adjacent to the enzyme-active site, and its phosphorylation allows the enzyme to reposition active-site residues into the optimal orientation for substrate binding and catalysis. Downstream substrates of MAPK include mitogen-activated protein-kinase-activated protein (MAPKAP) kinases and transcription factors, the phosphorylation of which, either directly or indirectly, regulates gene expression at several points, including transcription, nuclear export, and mRNA stability and translation. The cellular consequences of MAPK activation include inflammation, apoptosis, differentiation, and proliferation.

Distinct genes encode 4 p38 MAPK in humans: p38α, β, γ, and δ. Significant amino acid sequence homology is observed among the 4 isoforms, with 60%-75% overall sequence identity and >90% identity within the kinase domains. Tissue-selective expression is observed, with p38γ found predominantly in skeletal muscle, p38δ in the testes, pancreas, and small intestine. In contrast, p38α and β are more ubiquitously expressed.

An understanding of the broad biologic and pathophysiological roles of p38 MAPK family members has grown significantly over the past decade, as has the complexity of the signaling network leading to their activation. Scientific exploration of this pathway from biological, cellular, and in vivo perspectives was largely enabled by the availability of well-behaved, selective, small-molecule inhibitors of p38 MAPK that target the a and, to a lesser extent, β isoforms. p38α MAPK is the major isoform involved in the immune and inflammatory response. As such its function is critical for the production and activity of multiple pro-inflammatory cytokines, including TNFα, IL-1, IL-6, and IL-8, in cells such as macrophages, monocytes, synovial cells, and endothelial cells. p38 MAPK is also responsible for the induction of key inflammatory enzymes such as COX2 and iNOS, the major sources of eicosanoids and nitric oxide at sites of inflammation, respectively. Additionally, the p38 MAPK pathway regulates the expression of matrix metalloproteinases (MMP), including MMP2, MMP9, and MMP13.

The use of selective and potent inhibitors has facilitated the discovery of several families of p38 MAPK substrates, including transcription factors, MAPKAP kinases, and other enzymes. p38 MAPK can directly phosphorylate several transcription factors, such as myocyte-specific enhancer binding factor 2C (MEF2C), CHOP, peroxisome proliferator-activated receptor (PPAR) α, PPAR γ co-activator 1 and p53. These transcription factors are involved in cellular functions such as apoptosis, gluconeogenesis, and synthesis of enzymes involved in fatty acid oxidation. p38 MAPK is also involved in the direct or indirect phosphorylation of enzyme substrates, such as cytosolic phospholipase A2, and the Cdc25 phosphatases, which are involved in the activation of cyclin-dependent protein kinase activity and cell-cycle regulation. Therefore in addition to its role in the inflammatory response, p38 MAPK has other functions associated with normal and abnormal cell growth and survival as well as cellular function and homeostasis.

The MAPKAP kinases—MK2, MK-3, and PRAK—are selectively phosphorylated by p38 MAPK, while the phosphorylation of MSK1/2, MNK1/2, and RSKb is catalyzed by both p38 MAPK and ERK. Activation of RSKb is thought to play a role in cell survival, although the identification of substrates has been difficult, due to the lack of specific inhibitors. MNK is involved in the phosphorylation of eukaryotic initiation factor-4E, which binds to the 'cap' structure of mRNA and enhances protein translation. MNK phosphorylates the mRNA binding protein hnRNP-A0, a protein that regulates mRNA stability of transcripts encoding inflammatory proteins. MSK1/2 is involved in the phosphorylation of the transcription factors CREB and ATF-1, which regulate AP-1 binding proteins. In addition, MSK1/2 can phosphorylate Histone H3, which is involved in chromatin remodeling. While evidence suggests that MSK and MNK play a role in the mediation of pro-inflammatory cytokines, in vivo data with selective inhibitors and/or knockout mice are lacking.

MK-2, MK-3, and PRAK, once phosphorylated and activated by p38 MAPK, share similar substrate specificities. All of these kinases can phosphorylate the small heat-shock protein Hsp27. Studies have shown that the PRAK- and MK3-deficient mice do not display any resistance to endotoxic shock or a decrease in lipopolysaccharide-(LPS)-induced cytokine production. In contrast, MK-2-deficient mice show a resistance to endotoxic shock and an impaired inflammatory response, as well as a significantly decreased production of cytokines such as TNFα, IFNγ and IL-6. Thus, the p38/MK2 axis specifically is necessary and sufficient for mediating pro-inflammatory responses.

Recently, Davidson et al (2004) Discovery and characterization of a substrate selective p38alpha inhibitor, *Biochemistry* 43:11658-71, described a novel approach for increasing selectivity of a p38 MAPK inhibitors. In these studies, a high throughput screen was carried out using an assay that measured the p38-dependent phosphorylation and activation of MK2. The p38:MK2 complex is very stable with a Kd of 6 nM. The binding affinity of p38 for MK2 is driven by the C-terminal domain of MK2 containing several positively charged amino acid residues. Crystallographic studies of the p38:MK2 complex demonstrated that the C-terminal region of MK2 wraps around p38α and binds to the negatively charged ED binding site. The tight binding of p38 to MK2 may give rise to conformational changes providing additional binding pockets for inhibitors that would specifically be dependent upon the p38:MK2 interaction.

Taking advantage of the p38:MK2 interaction and using MK2 as the p38 substrate, a novel inhibitor of p38α was discovered exhibiting interesting properties (Davidson et al). This inhibitor demonstrated substrate selectivity by preventing the p38α dependent phosphorylation of MK2 (Ki app 300 nM) while sparing the p38α dependent phosphorylation of ATF2 (Ki app>20 uM). This novel inhibitor is functionally unique compared with traditional p38 ATP competitive inhibitors that block the p38-dependent phosphorylation of all p38 substrates. A second independent study also describes p38 inhibitors with unique mechanistic properties. This work demonstrates a novel mechanism for the selective inhibition of the p38 dependent phosphorylation of MK2. Unlike the previous study of Davidson et al., these mechanistically unique compounds are competitive with ATP and stabilize the p38/MK2 complex. Taken together, these two studies clearly prove the concept that selective p38/MK2 axis blockade is achievable with small molecule inhibitors. In comparison to traditional p38 MAPK inhibitors these p38/MK2 inhibitors should retain or enhance potency and exhibit improved safety features in animal models of disease or in human clinical settings.

The p38/MK2 role in the regulation of inflammatory cytokines (TNFα, IL-1β, IL-6) and enzymes responsible for inflammation (COX-2, iNOS, and MMPs) makes it an attractive drug target. Several classical p38 MAPK inhibitors have progressed to testing in clinical trials. Some of these candidates have failed, for safety or other reasons, but several have reported clinical data in diseases such as rheumatoid arthritis, pain, Crohn's disease, acute coronary syndrome, multiple myeloma and chronic obstructive pulmonary disease. In addition to these diseases several IL-1β mediated diseases could be impacted by a p38 inhibitor based upon the key role for the p38 MAPK pathway in the biosynthesis and activity of this cytokine. These diseases include the family of cryopyrin associated periodic disorders (CAPS), chronic gout, diabetes, Still's disease, Familial Mediterranean Fever among others.

In addition to human inflammatory pathways, p38 MAPK has been linked to canine B cell growth and survival. The role of p38 MAPK in B cell growth suggests that inhibition of this enzyme may be therapeutically beneficial for the treatment of canine B cell lymphoma. Canine lymphoma is one of the most common malignancies diagnosed in companion animals representing 10-25% of canine neoplasms and >80% of the hematopoietic tumors. An orally available, selective B cell growth inhibitor would meet a significant unmet medical need.

Compounds useful for treating diseases and conditions caused or exacerbated by unregulated p38 MAP Kinase and/or TNF activity are described in WO 2000/017175 published 30 Mar. 2000. The compounds described therein include a class of substituted urea compounds.

Compounds useful for treating diseases and conditions caused or exacerbated by unregulated p38 MAP Kinase and/or TNF activity are described in WO 2000/071535 published 30 Nov. 2000. The compounds described therein include a class of indole-type compounds.

Compounds useful for treating diseases and conditions caused or exacerbated by unregulated p38 MAP Kinase and/or TNF activity are described in WO 2002/042292 published 30 May 2002. The compounds described therein include a class of coupled indole-type derivatives.

Compounds useful for prophylaxis or treatment of circulatory diseases, metabolic diseases and/or central nervous system diseases are described in WO 2008/062905 published 29 May 2008. The compounds described therein include an alkyl-pyrimidinone-phenyl compounds wherein the phenyl fragment is substituted with a cyclopropyl radical, e.g., 6-butyl-3-(3-cyclopropylphenyl)-2methyl-5-{[2'-(5-oxo-4,5-dihydro-1,2,4-oxadizol-3-yl)biphenyl-4-yl]methyl}pyrimidin-4(3H)-one.

Various potential inhibitors or modulators of p38 kinase and the p38 kinase pathway are described in WO 2005/018557 published 3 Mar. 2005. The compounds described therein include di-fluorophenyl-methoxy-pyridinone-pyridyl compounds wherein the pyridyl fragment is substituted with various radicals including alkyl, alkenyl, hydroxyalkyl, halo, cyano, amino, carboxy, carbamoyl, methoxycarbonyl and hydroxyalkenylimino radicals.

Compounds useful for treating diseases and conditions caused or exacerbated by unregulated p38 MAP Kinase and/or TNF activity are described in US 2007/0167621 published 19 Jul. 2007. The compounds described therein include di-fluorophenyl-methoxy-pyrimidinone-phenyl compounds wherein the phenyl fragment is substituted with methyl amido radical.

Compounds useful for treating diseases and conditions caused or exacerbated by unregulated p38 MAP Kinase and/or TNF activity are described in WO 2004/087677 published 14 Oct. 2004. The compounds described therein include di-fluorophenyl-methoxy-pyrimidinone-phenyl compounds wherein the phenyl fragment is substituted with piperazinyl or a morpholinyl radical through a carbonyl bridge.

Pyrimidinone derivatives (as inhibitors of protein kinases and useful in treating disorders related to abnormal protein kinase activities such as inflammatory diseases and certain types of cancer), are described in WO 2007/081901 published 19 Jul. 2008. The compounds described therein include di-fluorophenyl-methoxy-pyrimidinone-phenyl compounds wherein the phenyl fragment is substituted with a cyclopropanyl or a morpholinyl radical through an amidoalkylamido bridge.

Pyrimidinone derivatives (as inhibitors of protein kinases and useful in treating disorders related to abnormal protein kinase activities such as inflammatory diseases and certain types of cancer) are described in WO 2008/153942 published 18 Dec. 2008. The compounds described therein include di-fluorophenyl-methoxy-pyrimidinone-phenyl compounds where the phenyl radical is substituted with cyclopentyl or a cyclohexyl radical through an amido bridge.

Compounds useful for treating diseases and conditions caused or exacerbated by unregulated p38 MAP Kinase and/or TNF activity are described in U.S. Pat. No. 7,067,540 published 27 Jun. 2007. The compounds described therein include di-fluorophenyl-methoxy-pyridinone-phenyl compounds wherein the phenyl radical is substituted with a five-membered heteroaryl radical (e.g., pyrazolyl or imidazolyl).

SUMMARY

In one embodiment, there is provided a compound of Formula (I):

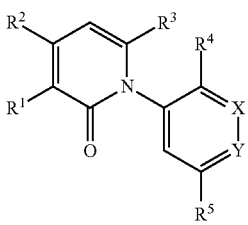
(I)

and a pharmaceutically acceptable salts thereof; wherein $R^1$, $R^2$, $R^3$, $R^4$, $R^5$, X and Y are as defined in the detailed description.

In another embodiment, there is provided a pharmaceutical composition comprising a compound of Formula (I) or a pharmaceutically acceptable salt thereof, and a pharmaceutically-acceptable carrier.

In various embodiments, the pharmaceutical composition further comprises one or more additional pharmaceutically active compounds.

In yet another embodiment, there is provided a method for treating a condition comprising administering to a subject a therapeutically effective amount of a compound of Formula (I), wherein the condition to be treated includes, but is not limited to, autoimmune disorders, chronic inflammatory disorders, acute inflammatory disorders, auto-inflammatory disorders, pain, atherosclerosis, diabetes, fibrotic diseases, metabolic disorders, cancer, neoplasia, leukemia, and lymphoma.

In various embodiments, the method comprises administering a combination of a compound of Formula (I) and at least one additional pharmaceutically active compound.

In yet another embodiment, there is provided a method for preparing a compound of Formula (I) or a pharmaceutically acceptable salt thereof.

In yet another embodiment, there is provided an intermediate useful in making a compound of Formula (I) or a pharmaceutically acceptable salt thereof.

The compounds above are more fully described in the detailed description that follows.

DETAILED DESCRIPTION

The following description is merely exemplary in nature and is not intended to limit the present disclosure, application, or uses.

A. Definitions

The use of generic terms in the description of the compounds are herein defined for clarity.

This specification uses the terms "substituent", "radical", "group", "moiety", and "fragment" interchangeably.

The term "hydrido" denotes a single —H atom (H) and may be used interchangeably with the symbol "H" or the term "hydrogen".

If a substituent is described as being "optionally substituted," the substituent may be either (1) not substituted or (2) substituted. If a substitutable position is not substituted, the default substituent is a hydrido radical.

As used herein, the singular forms "a" and "an" may include plural reference unless the context clearly dictates otherwise.

The term "alkyl", either alone or within other terms such as "haloalkyl" and "alkylaryl", refers to an acyclic alkyl radical containing 1, 2, 3, 4, 5, 6, 7, 8, 9 or 10 carbon atoms. In some embodiments, alkyl is a $C_1$-$C_{10}$ alkyl group or a $C_1$-$C_6$ alkyl group. Examples of alkyl groups include, but are not limited to, methyl, ethyl, propyl, isopropyl, butyl, isobutyl, t-butyl, pentyl, hexyl, heptyl, octyl, nonyl and decyl.

The term "alkoxy" is RO— where R is alkyl as defined herein. Non-limiting examples of alkoxy groups include methoxy, ethoxy and propoxy. The terms alkyloxy and alkoxy may be used interchangeably.

The term "alkoxyalkyl" refers to an alkyl moiety substituted with an alkoxy group. Examples of alkoxyalkyl groups include methoxymethyl, methoxyethyl, methoxypropyl and ethoxyethyl.

The term "aralkoxy" embraces an arylalkyl radical attached through an oxygen atom to the parent molecular scaffold. The terms "arylalkoxy" and "aralkoxy" may be used interchangeable.

The term "aryl" refers to any monocyclic, bicyclic or tricyclic carbon ring of up to 6 atoms in each ring, wherein at least one ring is aromatic, or an aromatic ring system of 5 to 14 carbons atoms which includes a carbocyclic aromatic group fused with a 5- or 6-membered cycloalkyl group. Examples of aryl groups include, but are not limited to, phenyl, naphthyl, tetrahydronaphthyl and indanyl.

The term "arylalkyl" embraces an aryl-substituted alkyl radical and may be used interchangeably with the term "aralkyl". Examples include benzyl, diphenylmethyl, triphenylmethyl, phenylethyl and diphenylethyl. The terms benzyl and phenylmethyl are interchangeable.

The term "aryloxy" is RO—, where R is aryl. "Arylthio" is RS—, where R is aryl.

The term "aryloxyalkyl" embraces an aryloxy radical attached to an alkyl group.

The term "cyano" denotes a carbon radical having 3 of 4 covalent bonds shared by a nitrogen atom.

The term "cycloalkyl" is a hydrocarbyl group containing at least one saturated or partially unsaturated ring structure, and attached via a ring carbon. In various embodiments, it refers to a saturated or a partially unsaturated $C_3$-$C_{12}$ cyclic moiety. Examples of cycloalkyl groups include cyclopropyl, cyclobutyl, cyclopentyl, cyclopentenyl, cyclohexyl, cyclohexenyl, cycloheptyl and cyclooctyl.

The term "halo" refers to fluoro (—F), chloro (—Cl), bromo (—Br), or iodo (—I).

The term "haloalkyl" refers to an alkyl moiety substituted with one or more halo groups. Examples of haloalkyl groups include —$CF_3$ and —$CHF_2$.

The term "haloaralkoxy" refers to aralkoxy group substituted with one or more halo radicals. Examples of haloaralkoxy groups include fluorobenzyloxy, difluorobenzyloxy. In various embodiments of the invention, haloaralkoxy is 4-fluorobenzyloxy or 2,4-difluorobenzyloxy.

The term "heterocyclyl" includes the heteroaryls defined below and refers to a saturated or partially unsaturated monocyclic, bicyclic or tricyclic group of 2 to 14 ring-carbon atoms and, in addition to ring-carbon atoms, 1 to 4 heteroatoms selected from P, N, O and S. In various embodiments the heterocyclic group is attached to another moiety through carbon or through a heteroatom, and is optionally substituted on carbon or a heteroatom. Examples of heterocyclyl include azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

The term "heteroaryl" refers to a monocyclic, bicyclic or tricyclic ring having up to 6 atoms in each ring, wherein at least one ring is aromatic and contains from 1 to 4 heteroatoms in the ring selected from the group consisting of N, O and S. Non-limiting examples of heteroaryl include pyridyl, thienyl, furanyl, pyrimidyl, imidazolyl, pyranyl, pyrazolyl, thiazolyl, thiadiazolyl, isothiazolyl, oxazolyl, isoxazoyl, pyrrolyl, pyridazinyl, pyrazinyl, quinolinyl, isoquinolinyl, benzofuranyl, dibenzofuranyl, dibenzothiophenyl, benzothienyl, indolyl, benzothiazolyl, benzooxazolyl, benzimidazolyl, isoindolyl, benzotriazolyl, purinyl, thianaphthenyl and pyrazinyl. Attachment of heteroaryl can occur via an aromatic ring, or, if heteroaryl is bicyclic or tricyclic and one of the rings is not aromatic or contains no heteroatoms, through a non-aromatic ring or a ring containing no heteroatoms. "Heteroaryl" is also understood to include the N-oxide derivative of any nitrogen containing heteroaryl.

The term "heteroaralkoxy" embraces a heteroarylalkyl radical attached through an oxygen atom to the molecular scaffold. A class of preferred heteroaralkoxy radicals is "lower heteroaralkoxy" radicals having an alkyl range of 1-3 carbon atoms. A preferred class of $C_6$-heteroarylalkoxy radicals is (pyridin-2-yl)methoxy.

The term "heteroaryloxy" is RO—, where R is heteroaryl as defined herein. Examples include thiophen-2-yl-oxy, pyridin-2-yl-oxy, pyridin-3-yl-oxy, and pyridin-4-yl-oxy.

The term "heteroaryloxyalkyl" is a heteroaryloxy radical further attached to an alkyl radical.

The term "hydroxyl" refers to —OH radical and may be used interchangeably with "hydroxyl".

The term "hydroxyalkyl" refers to a linear or branched monovalent $C_1$-$C_{10}$ hydrocarbon group substituted with at least one hydroxy group and examples of hydroxyalkyl groups include, but are not limited to, hydroxymethyl, hydroxyethyl, hydroxypropyl and hydroxybutyl.

The number of carbon atoms in a hydrocarbyl substituent can be indicated by the prefix "$C_X$-$C_Y$" where X is the minimum and Y is the maximum number of carbon atoms in the substituent.

The term "pharmaceutically-acceptable" means suitable for use in pharmaceutical preparations, generally considered as safe for such use, officially approved by a regulatory agency of a national or state government for such use, or being listed in the U. S. Pharmacopoeia or other generally recognized pharmacopoeia for use in animals, and more particularly in humans.

The term "pharmaceutically-acceptable salt" refers to a salt which may enhance desired pharmacological activity. Examples of pharmaceutically-acceptable salts include acid addition salts formed with inorganic or organic acids, metal salts and amine salts. Examples of acid addition salts formed with inorganic acids include salts with hydrochloric acid, hydrobromic acid, sulfuric acid, nitric acid and phosphoric acid. Examples of acid addition salts formed with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxy-benzoyl)-benzoic acid, cinnamic acid, mandelic acid, methanesulfonic acid, ethanesulfonic acid, 1,2-ethanedisulfonic acid, 2-hydroxyethane-sulfonic acid, benzenesulfonic acid, p-chlorobenzenesulfonic acid, 2-naphthalenesulfonic acid, p-toluenesulfonic acid, camphorsulfonic acid, 4-methyl-bicyclo[2.2.2]oct-2-ene1-carboxylic acid, gluco-heptonic acid, 4,4'-methylenebis(3-hydroxy-2-naphthoic) acid, 3-phenylpropionic acid, trimethyl-acetic acid, tertiary butylacetic acid, lauryl sulfuric acid, gluconic acid, glutamic acid, hydroxy-naphthoic acids, salicylic acid, stearic acid and muconic acid. Examples of metal salts include salts with sodium, potassium, calcium, magnesium, aluminum, iron, and zinc ions. Examples of amine salts include salts with ammonia and organic nitrogenous bases strong enough to form salts with carboxylic acids.

The term "therapeutically-effective amount" refers to an amount of a compound that, when administered to a subject for treating a disease, is sufficient to effect treatment for the disease. "Therapeutically effective amount" can vary depending on the compound, the disease and its severity, the age, the weight, etc. of the subject to be treated.

Compounds of the present invention can exist in tautomeric, geometric or stereoisomeric forms. The compounds' corresponding esters, metabolites, oximes, prodrugs, oniums and N-oxides are also embraced by the invention. The present invention contemplates all such compounds, including cis- and trans-geometric isomers, E- and Z-geometric isomers, R- and S-enantiomers, diastereomers, d-isomers, l-isomers, mixtures of isomers and racemates thereof, as falling within the scope of the invention.

The terms "cis" and "trans" denote a form of geometric isomerism in which two carbon atoms connected by a double bond will each have a radical atom on the same side of the double bond ("cis") or on opposite sides of the double bond ("trans").

Some of the compounds described contain one or more stereocenters and are meant to include R, S and mixtures of R and S forms for each stereocenter present.

The compounds of the invention may also exist as atropisomers, i.e., chiral rotational isomers. The invention encompasses the racemic, resolved atropisomers, and mixtures thereof.

B. Compounds

The present disclosure provides a compound having the structure of Formula (I):

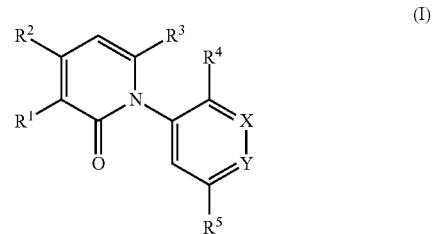

and a pharmaceutically acceptable salt thereof, wherein:

X and Y are independently selected from the group consisting of CH and N, with the proviso that when X is CH, Y is N, and when X is N, Y is CH;

$R^1$ is selected from the group consisting of —H, $C_1$-$C_6$-alkyl, and halo;

$R^2$ is selected from the group consisting of alkyl and alkoxy, wherein the alkyl or alkoxy is optionally substituted with one or more substituents independently selected from the group consisting of cycloalkyl, aryl, and heterocyclyl, and wherein the cycloalkyl or aryl is optionally substituted with one or more substituents independently selected from the group consisting of alkyl, alkoxy and halo, and wherein the heterocyclyl is optionally substituted with one or more substituents independently selected from the group consisting of alkyl, alkoxy and cyano;

$R^3$ and $R^4$ are independently selected from the group consisting of —H, alkyl and halo; and $R^5$ is selected from the group consisting of cycloalkyl, aryl, and heterocyclyl, wherein the cycloalkyl or aryl is optionally substituted with one or more substituents independently selected from the group consisting of halo, cyano, alkyl, hydroxyalkyl, alkoxyalkyl and aminoalkyl, and wherein the heterocyclyl is optionally substituted with one or more substituents independently selected from the group consisting of cyano, alkyl, hydroxyalkyl, alkoxyalkyl and aminoalkyl.

In one embodiment of the compounds of Formula (I), X is CH and Y is N; $R^1$ is selected from the group consisting of $C_1$-$C_3$-alkyl, bromo, chloro and fluoro; $R^2$ is alkoxy, optionally substituted with one or more heterocyclyl substituents optionally substituted with one or more substituents independently selected from the group consisting of $C_1$-$C_3$-alkyl and cyano; $R^3$ is $C_1$-$C_3$-alkyl; $R^4$ is selected from the group consisting of —H, $C_1$-$C_3$-alkyl, bromo, chloro and fluoro; and $R^5$ is heterocyclyl optionally substituted with one or more substituents independently selected from the group consisting of alkyl, hydroxyalkyl and aminoalkyl.

In another embodiment of the compounds of Formula (I), X is CH and Y is N; $R^1$ is methyl, bromo or chloro; $R^2$ is alkoxy optionally substituted with five- or six-membered heteroaryl optionally substituted with one or more substituents independently selected from $C_1$-$C_3$-alkyl; $R^3$ is methyl; $R^4$ is —H, methyl or chloro; and $R^5$ is five- or six-membered heteroaryl optionally substituted with one or more substituents independently selected from the group consisting of alkyl and hydroxyalkyl.

In still another embodiment of the compounds of Formula (I), X is CH and Y is N; $R^1$ is methyl, bromo or chloro; $R^2$ is alkoxy substituted with five-membered heteroaryl optionally substituted with one or more methyl substituents; $R^3$ is methyl; $R^4$ is —H, methyl or chloro; and $R^5$ is pyridine or pyrimidine, each of which is optionally substituted with one or more substituents independently selected from the group consisting of alkyl and hydroxyalkyl.

In another embodiment, there is provided a compound having the structure of Formula (II):

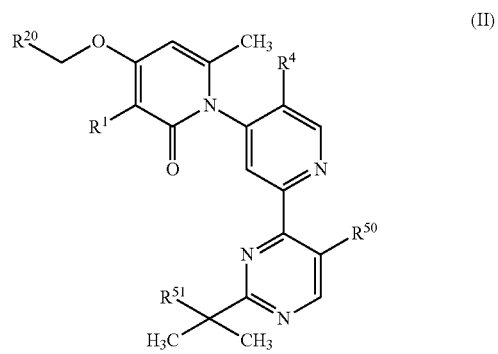

(II)

and a pharmaceutically acceptable salt thereof, wherein:

$R^1$ is methyl, bromo or chloro;

$R^4$ is —H, methyl or chloro;

$R^{20}$ is five-membered heteroaryl optionally substituted with one or more methyl groups;

$R^{50}$ is —H or methyl; and $R^{51}$ is —H, methyl or hydroxy.

Non-limiting examples of Formula (II) compounds include the following compounds and pharmaceutically acceptable salts thereof:

| No. | Compound Name |
|---|---|
| 1. | 2'-(2-(2-hydroxypropan-2-yl)pyrimidin-4-yl)-3,5',6-trimethyl-4-((2-methyloxazol-4-yl)methoxy)-2H-[1,4'-bipyridin]-2-one; |
| 2. | 2'-(2-(2-hydroxypropan-2-yl)pyrimidin-4-yl)-3,5',6-trimethyl-4-((2-methylthiazol-4-yl)methoxy)-2H-[1,4'-bipyridin]-2-one; |
| 3. | 2'-(2-(2-hydroxypropan-2-yl)pyrimidin-4-yl)-3,5',6-trimethyl-4-((1-methyl-1H-pyrazol-3-yl)methoxy)-2H-[1,4'-bipyridin]-2-one; |
| 4. | 3-bromo-2'-(2-(2-hydroxypropan-2-yl)pyrimidin-4-yl)-5',6-dimethyl-4-((2-methyloxazol-4-yl)methoxy)-2H-[1,4'-bipyridin]-2-one; |
| 5. | 3-bromo-2'-(2-(2-hydroxypropan-2-yl)pyrimidin-4-yl)-5',6-dimethyl-4-((2-methylthiazol-4-yl)methoxy)-2H-[1,4'-bipyridin]-2-one; |
| 6. | 3-bromo-2'-(2-(2-hydroxypropan-2-yl)pyrimidin-4-yl)-5',6-dimethyl-4-((1-methyl-1H-pyrazol-3-yl)methoxy)-2H-[1,4'-bipyridin]-2-one; |
| 7. | 2'-(2-(2-hydroxypropan-2-yl)-5-methylpyrimidin-4-yl)-3,5',6-trimethyl-4-((2-methyloxazol-4-yl)methoxy)-2H-[1,4'-bipyridin]-2-one; |
| 8. | 2'-(2-(2-hydroxypropan-2-yl)-5-methylpyrimidin-4-yl)-3,5',6-trimethyl-4-((2-methylthiazol-4-yl)methoxy)-2H-[1,4'-bipyridin]-2-one; |
| 9. | 2'-(2-(2-hydroxypropan-2-yl)-5-methylpyrimidin-4-yl)-3,5',6-trimethyl-4-((1-methyl-1H-pyrazol-3-yl)methoxy)-2H-[1,4'-bipyridin]-2-one; |
| 10. | 3-bromo-2'-(2-(2-hydroxypropan-2-yl)-5-methylpyrimidin-4-yl)-5',6-dimethyl-4-((2-methyloxazol-4-yl)methoxy)-2H-[1,4'-bipyridin]-2-one; |
| 11. | 3-bromo-2'-(2-(2-hydroxypropan-2-yl)-5-methylpyrimidin-4-yl)-5',6-dimethyl-4-((2-methylthiazol-4-yl)methoxy)-2H-[1,4'-bipyridin]-2-one; |
| 12. | 3-bromo-2'-(2-(2-hydroxypropan-2-yl)-5-methylpyrimidin-4-yl)-5',6-dimethyl-4-((1-methyl-1H-pyrazol-3-yl)methoxy)-2H-[1,4'-bipyridin]-2-one; |
| 13. | 3-chloro-2'-(2-(2-hydroxypropan-2-yl)pyrimidin-4-yl)-5',6-dimethyl-4-((2-methyloxazol-4-yl)methoxy)-2H-[1,4'-bipyridin]-2-one; |
| 14. | 3-chloro-2'-(2-(2-hydroxypropan-2-yl)pyrimidin-4-yl)-5',6-dimethyl-4-((2-methylthiazol-4- |

| No. | Compound Name |
|---|---|
| | yl)methoxy)-2H-[1,4'-bipyridin]-2-one; and |
| 15. | 3-chloro-2'-(2-(2-hydroxypropan-2-yl)pyrimidin-4-yl)-5',6-dimethyl-4-((1-methyl-1H-pyrazol-3-yl)methoxy)-2H-[1,4'-bipyridin]-2-one. |
| 16. | 3-bromo-2'-(2-(tert-butyl)pyrimidin-4-yl)-5',6-dimethyl-4-((2-methyloxazol-4-yl)methoxy)-2H-[1,4'-bipyridin]-2-one; |
| 17. | 2'-(2-(tert-butyl)pyrimidin-4-yl)-3-chloro-5',6-dimethyl-4-((2-methyloxazol-4-yl)methoxy)-2H-[1,4'-bipyridin]-2-one; |
| 18. | 2'-(2-(tert-butyl)pyrimidin-4-yl)-3,5',6-trimethyl-4-((2-methyloxazol-4-yl)methoxy)-2H-[1,4'-bipyridin]-2-one; |
| 19. | 3-bromo-2'-(2-(tert-butyl)pyrimidin-4-yl)-5'-chloro-6-methyl-4-((2-methyloxazol-4-yl)methoxy)-2H-[1,4'-bipyridin]-2-one; |
| 20. | 2'-(2-(tert-butyl)pyrimidin-4-yl)-3,5'-dichloro-6-methyl-4-((2-methyloxazol-4-yl)methoxy)-2H-[1,4'-bipyridin]-2-one; |
| 21. | 2'-(2-(tert-butyl)pyrimidin-4-yl)-5'-chloro-3,6-dimethyl-4-((2-methyloxazol-4-yl)methoxy)-2H-[1,4'-bipyridin]-2-one; |
| 22. | 3-bromo-2'-(2-(tert-butyl)pyrimidin-4-yl)-6-methyl-4-((2-methyloxazol-4-yl)methoxy)-2H-[1,4'-bipyridin]-2-one; |
| 23. | 2'-(2-(tert-butyl)pyrimidin-4-yl)-3-chloro-6-methyl-4-((2-methyloxazol-4-yl)methoxy)-2H-[1,4'-bipyridin]-2-one; |
| 24. | 2'-(2-(tert-butyl)pyrimidin-4-yl)-3,6-dimethyl-4-((2-methyloxazol-4-yl)methoxy)-2H-[1,4'-bipyridin]-2-one; |
| 25. | 3-bromo-2'-(2-(tert-butyl)-5-methylpyrimidin-4-yl)-5',6-dimethyl-4-((2-methyloxazol-4-yl)methoxy)-2H-[1,4'-bipyridin]-2-one; |
| 26. | 2'-(2-(tert-butyl)-5-methylpyrimidin-4-yl)-3-chloro-5',6-dimethyl-4-((2-methyloxazol-4-yl)methoxy)-2H-[1,4'-bipyridin]-2-one; |
| 27. | 2'-(2-(tert-butyl)-5-methylpyrimidin-4-yl)-3,5',6-trimethyl-4-((2-methyloxazol-4-yl)methoxy)-2H-[1,4'-bipyridin]-2-one; |
| 28. | 3-bromo-2'-(2-(tert-butyl)-5-methylpyrimidin-4-yl)-5'-chloro-6-methyl-4-((2-methyloxazol-4-yl)methoxy)-2H-[1,4'-bipyridin]-2-one; |
| 29. | 2'-(2-(tert-butyl)-5-methylpyrimidin-4-yl)-3,5'-dichloro-6-methyl-4-((2-methyloxazol-4-yl)methoxy)-2H-[1,4'-bipyridin]-2-one; |
| 30. | 2'-(2-(tert-butyl)-5-methylpyrimidin-4-yl)-5'-chloro-3,6-dimethyl-4-((2-methyloxazol-4-yl)methoxy)-2H-[1,4'-bipyridin]-2-one; |
| 31. | 3-bromo-2'-(2-(tert-butyl)-5-methylpyrimidin-4-yl)-6-methyl-4-((2-methyloxazol-4-yl)methoxy)-2H-[1,4'-bipyridin]-2-one; |
| 32. | 2'-(2-(tert-butyl)-5-methylpyrimidin-4-yl)-3-chloro-6-methyl-4-((2-methyloxazol-4-yl)methoxy)-2H-[1,4'-bipyridin]-2-one; |
| 33. | 2'-(2-(tert-butyl)-5-methylpyrimidin-4-yl)-3,6-dimethyl-4-((2-methyloxazol-4-yl)methoxy)-2H-[1,4'-bipyridin]-2-one; |
| 34. | 3-bromo-2'-(2-isopropylpyrimidin-4-yl)-5',6-dimethyl-4-((2-methyloxazol-4-yl)methoxy)-2H-[1,4'-bipyridin]-2-one; |
| 35. | 3-chloro-2'-(2-isopropylpyrimidin-4-yl)-5',6-dimethyl-4-((2-methyloxazol-4-yl)methoxy)-2H-[1,4'-bipyridin]-2-one; |
| 36. | 2'-(2-isopropylpyrimidin-4-yl)-3,5',6-trimethyl-4-((2-methyloxazol-4-yl)methoxy)-2H-[1,4'-bipyridin]-2-one; |
| 37. | 3-bromo-5'-chloro-2'-(2-isopropylpyrimidin-4-yl)-6-methyl-4-((2-methyloxazol-4-yl)methoxy)-2H-[1,4'-bipyridin]-2-one; |
| 38. | 3,5'-dichloro-2'-(2-isopropylpyrimidin-4-yl)-6-methyl-4-((2-methyloxazol-4-yl)methoxy)-2H-[1,4'-bipyridin]-2-one; |
| 39. | 5'-chloro-2'-(2-isopropylpyrimidin-4-yl)-3,6-dimethyl-4-((2-methyloxazol-4-yl)methoxy)-2H-[1,4'-bipyridin]-2-one; |
| 40. | 3-bromo-2'-(2-isopropylpyrimidin-4-yl)-6-methyl-4-((2-methyloxazol-4-yl)methoxy)-2H-[1,4'-bipyridin]-2-one; |
| 41. | 3-chloro-2'-(2-isopropylpyrimidin-4-yl)-6-methyl-4-((2-methyloxazol-4-yl)methoxy)-2H-[1,4'-bipyridin]-2-one; |
| 42. | 2'-(2-isopropylpyrimidin-4-yl)-3,6-dimethyl-4-((2-methyloxazol-4-yl)methoxy)-2H-[1,4'-bipyridin]-2-one; |
| 43. | 3-bromo-2'-(2-isopropyl-5-methylpyrimidin-4-yl)-5',6-dimethyl-4-((2-methyloxazol-4-yl)methoxy)-2H-[1,4'-bipyridin]-2-one; |
| 44. | 3-chloro-2'-(2-isopropyl-5-methylpyrimidin-4-yl)-5',6-dimethyl-4-((2-methyloxazol-4-yl)methoxy)-2H-[1,4'-bipyridin]-2-one; |
| 45. | 2'-(2-isopropyl-5-methylpyrimidin-4-yl)-3,5',6-trimethyl-4-((2-methyloxazol-4-yl)methoxy)-2H-[1,4'-bipyridin]-2-one; |
| 46. | 3-bromo-5'-chloro-2'-(2-isopropyl-5-methylpyrimidin-4-yl)-6-methyl-4-((2-methyloxazol-4-yl)methoxy)-2H-[1,4'-bipyridin]-2-one; |
| 47. | 3,5'-dichloro-2'-(2-isopropyl-5-methylpyrimidin-4-yl)-6-methyl-4-((2-methyloxazol-4-yl)methoxy)-2H-[1,4'-bipyridin]-2-one; |
| 48. | 5'-chloro-2'-(2-isopropyl-5-methylpyrimidin-4-yl)-3,6-dimethyl-4-((2-methyloxazol-4-yl)methoxy)-2H-[1,4'-bipyridin]-2-one; |
| 49. | 3-bromo-2'-(2-isopropyl-5-methylpyrimidin-4-yl)-6-methyl-4-((2-methyloxazol-4-yl)methoxy)-2H-[1,4'-bipyridin]-2-one; |
| 50. | 3-chloro-2'-(2-isopropyl-5-methylpyrimidin-4-yl)-6-methyl-4-((2-methyloxazol-4-yl)methoxy)-2H-[1,4'-bipyridin]-2-one; |
| 51. | 2'-(2-isopropyl-5-methylpyrimidin-4-yl)-3,6-dimethyl-4-((2-methyloxazol-4-yl)methoxy)-2H-[1,4'-bipyridin]-2-one; |
| 52. | 3-bromo-5'-chloro-2'-(2-(2-hydroxypropan-2-yl)pyrimidin-4-yl)-6-methyl-4-((2-methyloxazol-4-yl)methoxy)-2H-[1,4'-bipyridin]-2-one; |

| No. | Compound Name |
|---|---|
| 53. | 3,5'-dichloro-2'-(2-(2-hydroxypropan-2-yl)pyrimidin-4-yl)-6-methyl-4-((2-methyloxazol-4-yl)methoxy)-2H-[1,4'-bipyridin]-2-one; |
| 54. | 5'-chloro-2'-(2-(2-hydroxypropan-2-yl)pyrimidin-4-yl)-3,6-dimethyl-4-((2-methyloxazol-4-yl)methoxy)-2H-[1,4'-bipyridin]-2-one; |
| 55. | 3-bromo-2'-(2-(2-hydroxypropan-2-yl)pyrimidin-4-yl)-6-methyl-4-((2-methyloxazol-4-yl)methoxy)-2H-[1,4'-bipyridin]-2-one; |
| 56. | 3-chloro-2'-(2-(2-hydroxypropan-2-yl)pyrimidin-4-yl)-6-methyl-4-((2-methyloxazol-4-yl)methoxy)-2H-[1,4'-bipyridin]-2-one; |
| 57. | 2'-(2-(2-hydroxypropan-2-yl)pyrimidin-4-yl)-3,6-dimethyl-4-((2-methyloxazol-4-yl)methoxy)-2H-[1,4'-bipyridin]-2-one; |
| 58. | 3-chloro-2'-(2-(2-hydroxypropan-2-yl)-5-methylpyrimidin-4-yl)-5',6-dimethyl-4-((2-methyloxazol-4-yl)methoxy)-2H-[1,4'-bipyridin]-2-one; |
| 59. | 3-bromo-5'-chloro-2'-(2-(2-hydroxypropan-2-yl)-5-methylpyrimidin-4-yl)-6-methyl-4-((2-methyloxazol-4-yl)methoxy)-2H-[1,4'-bipyridin]-2-one; |
| 60. | 3,5'-dichloro-2'-(2-(2-hydroxypropan-2-yl)-5-methylpyrimidin-4-yl)-6-methyl-4-((2-methyloxazol-4-yl)methoxy)-2H-[1,4'-bipyridin]-2-one; |
| 61. | 5'-chloro-2'-(2-(2-hydroxypropan-2-yl)-5-methylpyrimidin-4-yl)-3,6-dimethyl-4-((2-methyloxazol-4-yl)methoxy)-2H-[1,4'-bipyridin]-2-one; |
| 62. | 3-bromo-2'-(2-(2-hydroxypropan-2-yl)-5-methylpyrimidin-4-yl)-6-methyl-4-((2-methyloxazol-4-yl)methoxy)-2H-[1,4'-bipyridin]-2-one; |
| 63. | 3-chloro-2'-(2-(2-hydroxypropan-2-yl)-5-methylpyrimidin-4-yl)-6-methyl-4-((2-methyloxazol-4-yl)methoxy)-2H-[1,4'-bipyridin]-2-one; |
| 64. | 2'-(2-(2-hydroxypropan-2-yl)-5-methylpyrimidin-4-yl)-3,6-dimethyl-4-((2-methyloxazol-4-yl)methoxy)-2H-[1,4'-bipyridin]-2-one; |
| 65. | 3-bromo-2'-(2-(tert-butyl)pyrimidin-4-yl)-5',6-dimethyl-4-((1-methyl-1H-pyrazol-3-yl)methoxy)-2H-[1,4'-bipyridin]-2-one; |
| 66. | 2'-(2-(tert-butyl)pyrimidin-4-yl)-3-chloro-5',6-dimethyl-4-((1-methyl-1H-pyrazol-3-yl)methoxy)-2H-[1,4'-bipyridin]-2-one; |
| 67. | 2'-(2-(tert-butyl)pyrimidin-4-yl)-3,5',6-trimethyl-4-((1-methyl-1H-pyrazol-3-yl)methoxy)-2H-[1,4'-bipyridin]-2-one; |
| 68. | 3-bromo-2'-(2-(tert-butyl)pyrimidin-4-yl)-5'-chloro-6-methyl-4-((1-methyl-1H-pyrazol-3-yl)methoxy)-2H-[1,4'-bipyridin]-2-one; |
| 69. | 2'-(2-(tert-butyl)pyrimidin-4-yl)-3,5'-dichloro-6-methyl-4-((1-methyl-1H-pyrazol-3-yl)methoxy)-2H-[1,4'-bipyridin]-2-one; |
| 70. | 2'-(2-(tert-butyl)pyrimidin-4-yl)-5'-chloro-3,6-dimethyl-4-((1-methyl-1H-pyrazol-3-yl)methoxy)-2H-[1,4'-bipyridin]-2-one; |
| 71. | 3-bromo-2'-(2-(tert-butyl)pyrimidin-4-yl)-6-methyl-4-((1-methyl-1H-pyrazol-3-yl)methoxy)-2H-[1,4'-bipyridin]-2-one; |
| 72. | 2'-(2-(tert-butyl)pyrimidin-4-yl)-3-chloro-6-methyl-4-((1-methyl-1H-pyrazol-3-yl)methoxy)-2H-[1,4'-bipyridin]-2-one; |
| 73. | 2'-(2-(tert-butyl)pyrimidin-4-yl)-3,6-dimethyl-4-((1-methyl-1H-pyrazol-3-yl)methoxy)-2H-[1,4'-bipyridin]-2-one; |
| 74. | 3-bromo-2'-(2-(tert-butyl)-5-methylpyrimidin-4-yl)-5',6-dimethyl-4-((1-methyl-1H-pyrazol-3-yl)methoxy)-2H-[1,4'-bipyridin]-2-one; |
| 75. | 2'-(2-(tert-butyl)-5-methylpyrimidin-4-yl)-3-chloro-5',6-dimethyl-4-((1-methyl-1H-pyrazol-3-yl)methoxy)-2H-[1,4'-bipyridin]-2-one; |
| 76. | 2'-(2-(tert-butyl)-5-methylpyrimidin-4-yl)-3,5',6-trimethyl-4-((1-methyl-1H-pyrazol-3-yl)methoxy)-2H-[1,4'-bipyridin]-2-one; |
| 77. | 3-bromo-2'-(2-(tert-butyl)-5-methylpyrimidin-4-yl)-5'-chloro-6-methyl-4-((1-methyl-1H-pyrazol-3-yl)methoxy)-2H-[1,4'-bipyridin]-2-one; |
| 78. | 2'-(2-(tert-butyl)-5-methylpyrimidin-4-yl)-3,5'-dichloro-6-methyl-4-((1-methyl-1H-pyrazol-3-yl)methoxy)-2H-[1,4'-bipyridin]-2-one; |
| 79. | 2'-(2-(tert-butyl)-5-methylpyrimidin-4-yl)-5'-chloro-3,6-dimethyl-4-((1-methyl-1H-pyrazol-3-yl)methoxy)-2H-[1,4'-bipyridin]-2-one; |
| 80. | 3-bromo-2'-(2-(tert-butyl)-5-methylpyrimidin-4-yl)-6-methyl-4-((1-methyl-1H-pyrazol-3-yl)methoxy)-2H-[1,4'-bipyridin]-2-one; |
| 81. | 2'-(2-(tert-butyl)-5-methylpyrimidin-4-yl)-3-chloro-6-methyl-4-((1-methyl-1H-pyrazol-3-yl)methoxy)-2H-[1,4'-bipyridin]-2-one; |
| 82. | 2'-(2-(tert-butyl)-5-methylpyrimidin-4-yl)-3,6-dimethyl-4-((1-methyl-1H-pyrazol-3-yl)methoxy)-2H-[1,4'-bipyridin]-2-one; |
| 83. | 3-bromo-2'-(2-isopropylpyrimidin-4-yl)-5',6-dimethyl-4-((1-methyl-1H-pyrazol-3-yl)methoxy)-2H-[1,4'-bipyridin]-2-one; |
| 84. | 3-chloro-2'-(2-isopropylpyrimidin-4-yl)-5',6-dimethyl-4-((1-methyl-1H-pyrazol-3-yl)methoxy)-2H-[1,4'-bipyridin]-2-one; |
| 85. | 2'-(2-isopropylpyrimidin-4-yl)-3,5',6-trimethyl-4-((1-methyl-1H-pyrazol-3-yl)methoxy)-2H-[1,4'-bipyridin]-2-one; |
| 86. | 3-bromo-5'-chloro-2'-(2-isopropylpyrimidin-4-yl)-6-methyl-4-((1-methyl-1H-pyrazol-3-yl)methoxy)-2H-[1,4'-bipyridin]-2-one; |
| 87. | 3,5'-dichloro-2'-(2-isopropylpyrimidin-4-yl)-6-methyl-4-((1-methyl-1H-pyrazol-3-yl)methoxy)-2H-[1,4'-bipyridin]-2-one; |
| 88. | 5'-chloro-2'-(2-isopropylpyrimidin-4-yl)-3,6-dimethyl-4-((1-methyl-1H-pyrazol-3-yl)methoxy)-2H-[1,4'-bipyridin]-2-one; |
| 89. | 3-bromo-2'-(2-isopropylpyrimidin-4-yl)-6-methyl-4-((1-methyl-1H-pyrazol-3-yl)methoxy)-2H-[1,4'-bipyridin]-2-one; |
| 90. | 3-chloro-2'-(2-isopropylpyrimidin-4-yl)-6-methyl-4-((1-methyl-1H-pyrazol-3-yl)methoxy)-2H-[1,4'-bipyridin]-2-one; |
| 91. | 2'-(2-isopropylpyrimidin-4-yl)-3,6-dimethyl-4-((1-methyl-1H-pyrazol-3-yl)methoxy)-2H-[1,4'- |

| No. | Compound Name |
|---|---|
| | bipyridin]-2-one; |
| 92. | 3-bromo-2'-(2-isopropyl-5-methylpyrimidin-4-yl)-5',6-dimethyl-4-((1-methyl-1H-pyrazol-3-yl)methoxy)-2H-[1,4'-bipyridin]-2-one; |
| 93. | 3-chloro-2'-(2-isopropyl-5-methylpyrimidin-4-yl)-5',6-dimethyl-4-((1-methyl-1H-pyrazol-3-yl)methoxy)-2H-[1,4'-bipyridin]-2-one; |
| 94. | 2'-(2-isopropyl-5-methylpyrimidin-4-yl)-3,5',6-trimethyl-4-((1-methyl-1H-pyrazol-3-yl)methoxy)-2H-[1,4'-bipyridin]-2-one; |
| 95. | 3-bromo-5'-chloro-2'-(2-isopropyl-5-methylpyrimidin-4-yl)-6-methyl-4-((1-methyl-1H-pyrazol-3-yl)methoxy)-2H-[1,4'-bipyridin]-2-one; |
| 96. | 3,5'-dichloro-2'-(2-isopropyl-5-methylpyrimidin-4-yl)-6-methyl-4-((1-methyl-1H-pyrazol-3-yl)methoxy)-2H-[1,4'-bipyridin]-2-one; |
| 97. | 5'-chloro-2'-(2-isopropyl-5-methylpyrimidin-4-yl)-3,6-dimethyl-4-((1-methyl-1H-pyrazol-3-yl)methoxy)-2H-[1,4'-bipyridin]-2-one; |
| 98. | 3-bromo-2'-(2-isopropyl-5-methylpyrimidin-4-yl)-6-methyl-4-((1-methyl-1H-pyrazol-3-yl)methoxy)-2H-[1,4'-bipyridin]-2-one; |
| 99. | 3-chloro-2'-(2-isopropyl-5-methylpyrimidin-4-yl)-6-methyl-4-((1-methyl-1H-pyrazol-3-yl)methoxy)-2H-[1,4'-bipyridin]-2-one; |
| 100. | 2'-(2-isopropyl-5-methylpyrimidin-4-yl)-3,6-dimethyl-4-((1-methyl-1H-pyrazol-3-yl)methoxy)-2H-[1,4'-bipyridin]-2-one; |
| 101. | 3-bromo-5'-chloro-2'-(2-(2-hydroxypropan-2-yl)pyrimidin-4-yl)-6-methyl-4-((1-methyl-1H-pyrazol-3-yl)methoxy)-2H-[1,4'-bipyridin]-2-one; |
| 102. | 3,5'-dichloro-2'-(2-(2-hydroxypropan-2-yl)pyrimidin-4-yl)-6-methyl-4-((1-methyl-1H-pyrazol-3-yl)methoxy)-2H-[1,4'-bipyridin]-2-one; |
| 103. | 5'-chloro-2'-(2-(2-hydroxypropan-2-yl)pyrimidin-4-yl)-3,6-dimethyl-4-((1-methyl-1H-pyrazol-3-yl)methoxy)-2H-[1,4'-bipyridin]-2-one; |
| 104. | 3-bromo-2'-(2-(2-hydroxypropan-2-yl)pyrimidin-4-yl)-6-methyl-4-((1-methyl-1H-pyrazol-3-yl)methoxy)-2H-[1,4'-bipyridin]-2-one; |
| 105. | 3-chloro-2'-(2-(2-hydroxypropan-2-yl)pyrimidin-4-yl)-6-methyl-4-((1-methyl-1H-pyrazol-3-yl)methoxy)-2H-[1,4'-bipyridin]-2-one; |
| 106. | 2'-(2-(2-hydroxypropan-2-yl)pyrimidin-4-yl)-3,6-dimethyl-4-((1-methyl-1H-pyrazol-3-yl)methoxy)-2H-[1,4'-bipyridin]-2-one; |
| 107. | 3-chloro-2'-(2-(2-hydroxypropan-2-yl)-5-methylpyrimidin-4-yl)-5',6-dimethyl-4-((1-methyl-1H-pyrazol-3-yl)methoxy)-2H-[1,4'-bipyridin]-2-one; |
| 108. | 3-bromo-5'-chloro-2'-(2-(2-hydroxypropan-2-yl)-5-methylpyrimidin-4-yl)-6-methyl-4-((1-methyl-1H-pyrazol-3-yl)methoxy)-2H-[1,4'-bipyridin]-2-one; |
| 109. | 3,5'-dichloro-2'-(2-(2-hydroxypropan-2-yl)-5-methylpyrimidin-4-yl)-6-methyl-4-((1-methyl-1H-pyrazol-3-yl)methoxy)-2H-[1,4'-bipyridin]-2-one; |
| 110. | 5'-chloro-2'-(2-(2-hydroxypropan-2-yl)-5-methylpyrimidin-4-yl)-3,6-dimethyl-4-((1-methyl-1H-pyrazol-3-yl)methoxy)-2H-[1,4'-bipyridin]-2-one; |
| 111. | 3-bromo-2'-(2-(2-hydroxypropan-2-yl)-5-methylpyrimidin-4-yl)-6-methyl-4-((1-methyl-1H-pyrazol-3-yl)methoxy)-2H-[1,4'-bipyridin]-2-one; |
| 112. | 3-chloro-2'-(2-(2-hydroxypropan-2-yl)-5-methylpyrimidin-4-yl)-6-methyl-4-((1-methyl-1H-pyrazol-3-yl)methoxy)-2H-[1,4'-bipyridin]-2-one; |
| 113. | 2'-(2-(2-hydroxypropan-2-yl)-5-methylpyrimidin-4-yl)-3,6-dimethyl-4-((1-methyl-1H-pyrazol-3-yl)methoxy)-2H-[1,4'-bipyridin]-2-one; |
| 114. | 3-bromo-2'-(2-(tert-butyl)pyrimidin-4-yl)-5',6-dimethyl-4-((2-methylthiazol-4-yl)methoxy)-2H-[1,4'-bipyridin]-2-one; |
| 115. | 2'-(2-(tert-butyl)pyrimidin-4-yl)-3-chloro-5',6-dimethyl-4-((2-methylthiazol-4-yl)methoxy)-2H-[1,4'-bipyridin]-2-one; |
| 116. | 2'-(2-(tert-butyl)pyrimidin-4-yl)-3,5',6-trimethyl-4-((2-methylthiazol-4-yl)methoxy)-2H-[1,4'-bipyridin]-2-one; |
| 117. | 3-bromo-2'-(2-(tert-butyl)pyrimidin-4-yl)-5'-chloro-6-methyl-4-((2-methylthiazol-4-yl)methoxy)-2H-[1,4'-bipyridin]-2-one; |
| 118. | 2'-(2-(tert-butyl)pyrimidin-4-yl)-3,5'-dichloro-6-methyl-4-((2-methylthiazol-4-yl)methoxy)-2H-[1,4'-bipyridin]-2-one; |
| 119. | 2'-(2-(tert-butyl)pyrimidin-4-yl)-5'-chloro-3,6-dimethyl-4-((2-methylthiazol-4-yl)methoxy)-2H-[1,4'-bipyridin]-2-one; |
| 120. | 3-bromo-2'-(2-(tert-butyl)pyrimidin-4-yl)-6-methyl-4-((2-methylthiazol-4-yl)methoxy)-2H-[1,4'-bipyridin]-2-one; |
| 121. | 2'-(2-(tert-butyl)pyrimidin-4-yl)-3-chloro-6-methyl-4-((2-methylthiazol-4-yl)methoxy)-2H-[1,4'-bipyridin]-2-one; |
| 122. | 2'-(2-(tert-butyl)pyrimidin-4-yl)-3,6-dimethyl-4-((2-methylthiazol-4-yl)methoxy)-2H-[1,4'-bipyridin]-2-one; |
| 123. | 3-bromo-2'-(2-(tert-butyl)-5-methylpyrimidin-4-yl)-5',6-dimethyl-4-((2-methylthiazol-4-yl)methoxy)-2H-[1,4'-bipyridin]-2-one; |
| 124. | 2'-(2-(tert-butyl)-5-methylpyrimidin-4-yl)-3-chloro-5',6-dimethyl-4-((2-methylthiazol-4-yl)methoxy)-2H-[1,4'-bipyridin]-2-one; |
| 125. | 2'-(2-(tert-butyl)-5-methylpyrimidin-4-yl)-3,5',6-trimethyl-4-((2-methylthiazol-4-yl)methoxy)-2H-[1,4'-bipyridin]-2-one; |
| 126. | 3-bromo-2'-(2-(tert-butyl)-5-methylpyrimidin-4-yl)-5'-chloro-6-methyl-4-((2-methylthiazol-4-yl)methoxy)-2H-[1,4'-bipyridin]-2-one; |
| 127. | 2'-(2-(tert-butyl)-5-methylpyrimidin-4-yl)-3,5'-dichloro-6-methyl-4-((2-methylthiazol-4-yl)methoxy)-2H-[1,4'-bipyridin]-2-one; |
| 128. | 2'-(2-(tert-butyl)-5-methylpyrimidin-4-yl)-5'-chloro-3,6-dimethyl-4-((2-methylthiazol-4-yl)methoxy)-2H-[1,4'-bipyridin]-2-one; |
| 129. | 3-bromo-2'-(2-(tert-butyl)-5-methylpyrimidin-4-yl)-6-methyl-4-((2-methylthiazol-4-yl)methoxy)-2H-[1,4'-bipyridin]-2-one; |

-continued

| No. | Compound Name |
|---|---|
| 130. | 2'-(2-(tert-butyl)-5-methylpyrimidin-4-yl)-3-chloro-6-methyl-4-((2-methylthiazol-4-yl)methoxy)-2H-[1,4'-bipyridin]-2-one; |
| 131. | 2'-(2-(tert-butyl)-5-methylpyrimidin-4-yl)-3,6-dimethyl-4-((2-methylthiazol-4-yl)methoxy)-2H-[1,4'-bipyridin]-2-one; |
| 132. | 3-bromo-2'-(2-isopropylpyrimidin-4-yl)-5',6-dimethyl-4-((2-methylthiazol-4-yl)methoxy)-2H-[1,4'-bipyridin]-2-one; |
| 133. | 3-chloro-2'-(2-isopropylpyrimidin-4-yl)-5',6-dimethyl-4-((2-methylthiazol-4-yl)methoxy)-2H-[1,4'-bipyridin]-2-one; |
| 134. | 2'-(2-isopropylpyrimidin-4-yl)-3,5',6-trimethyl-4-((2-methylthiazol-4-yl)methoxy)-2H-[1,4'-bipyridin]-2-one; |
| 135. | 3-bromo-5'-chloro-2'-(2-isopropylpyrimidin-4-yl)-6-methyl-4-((2-methylthiazol-4-yl)methoxy)-2H-[1,4'-bipyridin]-2-one; |
| 136. | 3,5'-dichloro-2'-(2-isopropylpyrimidin-4-yl)-6-methyl-4-((2-methylthiazol-4-yl)methoxy)-2H-[1,4'-bipyridin]-2-one; |
| 137. | 5'-chloro-2'-(2-isopropylpyrimidin-4-yl)-3,6-dimethyl-4-((2-methylthiazol-4-yl)methoxy)-2H-[1,4'-bipyridin]-2-one; |
| 138. | 3-bromo-2'-(2-isopropylpyrimidin-4-yl)-6-methyl-4-((2-methylthiazol-4-yl)methoxy)-2H-[1,4'-bipyridin]-2-one; |
| 139. | 3-chloro-2'-(2-isopropylpyrimidin-4-yl)-6-methyl-4-((2-methylthiazol-4-yl)methoxy)-2H-[1,4'-bipyridin]-2-one; |
| 140. | 2'-(2-isopropylpyrimidin-4-yl)-3,6-dimethyl-4-((2-methylthiazol-4-yl)methoxy)-2H-[1,4'-bipyridin]-2-one; |
| 141. | 3-bromo-2'-(2-isopropyl-5-methylpyrimidin-4-yl)-5',6-dimethyl-4-((2-methylthiazol-4-yl)methoxy)-2H-[1,4'-bipyridin]-2-one; |
| 142. | 3-chloro-2'-(2-isopropyl-5-methylpyrimidin-4-yl)-5',6-dimethyl-4-((2-methylthiazol-4-yl)methoxy)-2H-[1,4'-bipyridin]-2-one; |
| 143. | 2'-(2-isopropyl-5-methylpyrimidin-4-yl)-3,5',6-trimethyl-4-((2-methylthiazol-4-yl)methoxy)-2H-[1,4'-bipyridin]-2-one; |
| 144. | 3-bromo-5'-chloro-2'-(2-isopropyl-5-methylpyrimidin-4-yl)-6-methyl-4-((2-methylthiazol-4-yl)methoxy)-2H-[1,4'-bipyridin]-2-one; |
| 145. | 3,5'-dichloro-2'-(2-isopropyl-5-methylpyrimidin-4-yl)-6-methyl-4-((2-methylthiazol-4-yl)methoxy)-2H-[1,4'-bipyridin]-2-one; |
| 146. | 5'-chloro-2'-(2-isopropyl-5-methylpyrimidin-4-yl)-3,6-dimethyl-4-((2-methylthiazol-4-yl)methoxy)-2H-[1,4'-bipyridin]-2-one; |
| 147. | 3-bromo-2'-(2-isopropyl-5-methylpyrimidin-4-yl)-6-methyl-4-((2-methylthiazol-4-yl)methoxy)-2H-[1,4'-bipyridin]-2-one; |
| 148. | 3-chloro-2'-(2-isopropyl-5-methylpyrimidin-4-yl)-6-methyl-4-((2-methylthiazol-4-yl)methoxy)-2H-[1,4'-bipyridin]-2-one; |
| 149. | 2'-(2-isopropyl-5-methylpyrimidin-4-yl)-3,6-dimethyl-4-((2-methylthiazol-4-yl)methoxy)-2H-[1,4'-bipyridin]-2-one; |
| 150. | 3-bromo-5'-chloro-2'-(2-(2-hydroxypropan-2-yl)pyrimidin-4-yl)-6-methyl-4-((2-methylthiazol-4-yl)methoxy)-2H-[1,4'-bipyridin]-2-one; |
| 151. | 3,5'-dichloro-2'-(2-(2-hydroxypropan-2-yl)pyrimidin-4-yl)-6-methyl-4-((2-methylthiazol-4-yl)methoxy)-2H-[1,4'-bipyridin]-2-one; |
| 152. | 5'-chloro-2'-(2-(2-hydroxypropan-2-yl)pyrimidin-4-yl)-3,6-dimethyl-4-((2-methylthiazol-4-yl)methoxy)-2H-[1,4'-bipyridin]-2-one; |
| 153. | 3-bromo-2'-(2-(2-hydroxypropan-2-yl)pyrimidin-4-yl)-6-methyl-4-((2-methylthiazol-4-yl)methoxy)-2H-[1,4'-bipyridin]-2-one; |
| 154. | 3-chloro-2'-(2-(2-hydroxypropan-2-yl)pyrimidin-4-yl)-6-methyl-4-((2-methylthiazol-4-yl)methoxy)-2H-[1,4'-bipyridin]-2-one; |
| 155. | 2'-(2-(2-hydroxypropan-2-yl)pyrimidin-4-yl)-3,6-dimethyl-4-((2-methylthiazol-4-yl)methoxy)-2H-[1,4'-bipyridin]-2-one; |
| 156. | 3-chloro-2'-(2-(2-hydroxypropan-2-yl)-5-methylpyrimidin-4-yl)-5',6-dimethyl-4-((2-methylthiazol-4-yl)methoxy)-2H-[1,4'-bipyridin]-2-one; |
| 157. | 3-bromo-5'-chloro-2'-(2-(2-hydroxypropan-2-yl)-5-methylpyrimidin-4-yl)-6-methyl-4-((2-methylthiazol-4-yl)methoxy)-2H-[1,4'-bipyridin]-2-one; |
| 158. | 3,5'-dichloro-2'-(2-(2-hydroxypropan-2-yl)-5-methylpyrimidin-4-yl)-6-methyl-4-((2-methylthiazol-4-yl)methoxy)-2H-[1,4'-bipyridin]-2-one; |
| 159. | 5'-chloro-2'-(2-(2-hydroxypropan-2-yl)-5-methylpyrimidin-4-yl)-3,6-dimethyl-4-((2-methylthiazol-4-yl)methoxy)-2H-[1,4'-bipyridin]-2-one; |
| 160. | 3-bromo-2'-(2-(2-hydroxypropan-2-yl)-5-methylpyrimidin-4-yl)-6-methyl-4-((2-methylthiazol-4-yl)methoxy)-2H-[1,4'-bipyridin]-2-one; |
| 161. | 3-chloro-2'-(2-(2-hydroxypropan-2-yl)-5-methylpyrimidin-4-yl)-6-methyl-4-((2-methylthiazol-4-yl)methoxy)-2H-[1,4'-bipyridin]-2-one; |
| 162. | 2'-(2-(2-hydroxypropan-2-yl)-5-methylpyrimidin-4-yl)-3,6-dimethyl-4-((2-methylthiazol-4-yl)methoxy)-2H-[1,4'-bipyridin]-2-one; |
| 163. | 3-bromo-2'-(2-(tert-butyl)pyrimidin-4-yl)-5',6-dimethyl-4-((5-methylthiophen-3-yl)methoxy)-2H-[1,4'-bipyridin]-2-one; |
| 164. | 2'-(2-(tert-butyl)pyrimidin-4-yl)-3-chloro-5',6-dimethyl-4-((5-methylthiophen-3-yl)methoxy)-2H-[1,4'-bipyridin]-2-one; |
| 165. | 2'-(2-(tert-butyl)pyrimidin-4-yl)-3,5',6-trimethyl-4-((5-methylthiophen-3-yl)methoxy)-2H-[1,4'-bipyridin]-2-one; |
| 166. | 3-bromo-2'-(2-(tert-butyl)pyrimidin-4-yl)-5'-chloro-6-methyl-4-((5-methylthiophen-3-yl)methoxy)-2H-[1,4'-bipyridin]-2-one; |
| 167. | 2'-(2-(tert-butyl)pyrimidin-4-yl)-3,5'-dichloro-6-methyl-4-((5-methylthiophen-3-yl)methoxy)-2H-[1,4'-bipyridin]-2-one; |
| 168. | 2'-(2-(tert-butyl)pyrimidin-4-yl)-5'-chloro-3,6-dimethyl-4-((5-methylthiophen-3-yl)methoxy)-2H-[1,4'- |

| No. | Compound Name |
|---|---|
| | bipyridin]-2-one; |
| 169. | 3-bromo-2'-(2-(tert-butyl)pyrimidin-4-yl)-6-methyl-4-((5-methylthiophen-3-yl)methoxy)-2H-[1,4'-bipyridin]-2-one; |
| 170. | 2'-(2-(tert-butyl)pyrimidin-4-yl)-3-chloro-6-methyl-4-((5-methylthiophen-3-yl)methoxy)-2H-[1,4'-bipyridin]-2-one; |
| 171. | 2'-(2-(tert-butyl)pyrimidin-4-yl)-3,6-dimethyl-4-((5-methylthiophen-3-yl)methoxy)-2H-[1,4'-bipyridin]-2-one; |
| 172. | 3-bromo-2'-(2-(tert-butyl)-5-methylpyrimidin-4-yl)-5',6-dimethyl-4-((5-methylthiophen-3-yl)methoxy)-2H-[1,4'-bipyridin]-2-one; |
| 173. | 2'-(2-(tert-butyl)-5-methylpyrimidin-4-yl)-3-chloro-5',6-dimethyl-4-((5-methylthiophen-3-yl)methoxy)-2H-[1,4'-bipyridin]-2-one; |
| 174. | 2'-(2-(tert-butyl)-5-methylpyrimidin-4-yl)-3,5',6-trimethyl-4-((5-methylthiophen-3-yl)methoxy)-2H-[1,4'-bipyridin]-2-one; |
| 175. | 3-bromo-2'-(2-(tert-butyl)-5-methylpyrimidin-4-yl)-5'-chloro-6-methyl-4-((5-methylthiophen-3-yl)methoxy)-2H-[1,4'-bipyridin]-2-one; |
| 176. | 2'-(2-(tert-butyl)-5-methylpyrimidin-4-yl)-3,5'-dichloro-6-methyl-4-((5-methylthiophen-3-yl)methoxy)-2H-[1,4'-bipyridin]-2-one; |
| 177. | 2'-(2-(tert-butyl)-5-methylpyrimidin-4-yl)-5'-chloro-3,6-dimethyl-4-((5-methylthiophen-3-yl)methoxy)-2H-[1,4'-bipyridin]-2-one; |
| 178. | 3-bromo-2'-(2-(tert-butyl)-5-methylpyrimidin-4-yl)-6-methyl-4-((5-methylthiophen-3-yl)methoxy)-2H-[1,4'-bipyridin]-2-one; |
| 179. | 2'-(2-(tert-butyl)-5-methylpyrimidin-4-yl)-3-chloro-6-methyl-4-((5-methylthiophen-3-yl)methoxy)-2H-[1,4'-bipyridin]-2-one; |
| 180. | 2'-(2-(tert-butyl)-5-methylpyrimidin-4-yl)-3,6-dimethyl-4-((5-methylthiophen-3-yl)methoxy)-2H-[1,4'-bipyridin]-2-one; |
| 181. | 3-bromo-2'-(2-isopropylpyrimidin-4-yl)-5',6-dimethyl-4-((5-methylthiophen-3-yl)methoxy)-2H-[1,4'-bipyridin]-2-one; |
| 182. | 3-chloro-2'-(2-isopropylpyrimidin-4-yl)-5',6-dimethyl-4-((5-methylthiophen-3-yl)methoxy)-2H-[1,4'-bipyridin]-2-one; |
| 183. | 2'-(2-isopropylpyrimidin-4-yl)-3,5',6-trimethyl-4-((5-methylthiophen-3-yl)methoxy)-2H-[1,4'-bipyridin]-2-one; |
| 184. | 3-bromo-5'-chloro-2'-(2-isopropylpyrimidin-4-yl)-6-methyl-4-((5-methylthiophen-3-yl)methoxy)-2H-[1,4'-bipyridin]-2-one; |
| 185. | 3,5'-dichloro-2'-(2-isopropylpyrimidin-4-yl)-6-methyl-4-((5-methylthiophen-3-yl)methoxy)-2H-[1,4'-bipyridin]-2-one; |
| 186. | 5'-chloro-2'-(2-isopropylpyrimidin-4-yl)-3,6-dimethyl-4-((5-methylthiophen-3-yl)methoxy)-2H-[1,4'-bipyridin]-2-one; |
| 187. | 3-bromo-2'-(2-isopropylpyrimidin-4-yl)-6-methyl-4-((5-methylthiophen-3-yl)methoxy)-2H-[1,4'-bipyridin]-2-one; |
| 188. | 3-chloro-2'-(2-isopropylpyrimidin-4-yl)-6-methyl-4-((5-methylthiophen-3-yl)methoxy)-2H-[1,4'-bipyridin]-2-one; |
| 189. | 2'-(2-isopropylpyrimidin-4-yl)-3,6-dimethyl-4-((5-methylthiophen-3-yl)methoxy)-2H-[1,4'-bipyridin]-2-one; |
| 190. | 3-bromo-2'-(2-isopropyl-5-methylpyrimidin-4-yl)-5',6-dimethyl-4-((5-methylthiophen-3-yl)methoxy)-2H-[1,4'-bipyridin]-2-one; |
| 191. | 3-chloro-2'-(2-isopropyl-5-methylpyrimidin-4-yl)-5',6-dimethyl-4-((5-methylthiophen-3-yl)methoxy)-2H-[1,4'-bipyridin]-2-one; |
| 192. | 2'-(2-isopropyl-5-methylpyrimidin-4-yl)-3,5',6-trimethyl-4-((5-methylthiophen-3-yl)methoxy)-2H-[1,4'-bipyridin]-2-one; |
| 193. | 3-bromo-5'-chloro-2'-(2-isopropyl-5-methylpyrimidin-4-yl)-6-methyl-4-((5-methylthiophen-3-yl)methoxy)-2H-[1,4'-bipyridin]-2-one; |
| 194. | 3,5'-dichloro-2'-(2-isopropyl-5-methylpyrimidin-4-yl)-6-methyl-4-((5-methylthiophen-3-yl)methoxy)-2H-[1,4'-bipyridin]-2-one; |
| 195. | 5'-chloro-2'-(2-isopropyl-5-methylpyrimidin-4-yl)-3,6-dimethyl-4-((5-methylthiophen-3-yl)methoxy)-2H-[1,4'-bipyridin]-2-one; |
| 196. | 3-bromo-2'-(2-isopropyl-5-methylpyrimidin-4-yl)-6-methyl-4-((5-methylthiophen-3-yl)methoxy)-2H-[1,4'-bipyridin]-2-one; |
| 197. | 3-chloro-2'-(2-isopropyl-5-methylpyrimidin-4-yl)-6-methyl-4-((5-methylthiophen-3-yl)methoxy)-2H-[1,4'-bipyridin]-2-one; |
| 198. | 2'-(2-isopropyl-5-methylpyrimidin-4-yl)-3,6-dimethyl-4-((5-methylthiophen-3-yl)methoxy)-2H-[1,4'-bipyridin]-2-one; |
| 199. | 3-bromo-2'-(2-(2-hydroxypropan-2-yl)pyrimidin-4-yl)-5',6-dimethyl-4-((5-methylthiophen-3-yl)methoxy)-2H-[1,4'-bipyridin]-2-one; |
| 200. | 3-chloro-2'-(2-(2-hydroxypropan-2-yl)pyrimidin-4-yl)-5',6-dimethyl-4-((5-methylthiophen-3-yl)methoxy)-2H-[1,4'-bipyridin]-2-one; |
| 201. | 2'-(2-(2-hydroxypropan-2-yl)pyrimidin-4-yl)-3,5',6-trimethyl-4-((5-methylthiophen-3-yl)methoxy)-2H-[1,4'-bipyridin]-2-one; |
| 202. | 3-bromo-5'-chloro-2'-(2-(2-hydroxypropan-2-yl)pyrimidin-4-yl)-6-methyl-4-((5-methylthiophen-3-yl)methoxy)-2H-[1,4'-bipyridin]-2-one; |
| 203. | 3,5'-dichloro-2'-(2-(2-hydroxypropan-2-yl)pyrimidin-4-yl)-6-methyl-4-((5-methylthiophen-3-yl)methoxy)-2H-[1,4'-bipyridin]-2-one; |
| 204. | 5'-chloro-2'-(2-(2-hydroxypropan-2-yl)pyrimidin-4-yl)-3,6-dimethyl-4-((5-methylthiophen-3-yl)methoxy)-2H-[1,4'-bipyridin]-2-one; |
| 205. | 3-bromo-2'-(2-(2-hydroxypropan-2-yl)pyrimidin-4-yl)-6-methyl-4-((5-methylthiophen-3-yl)methoxy)-2H-[1,4'-bipyridin]-2-one; |
| 206. | 3-chloro-2'-(2-(2-hydroxypropan-2-yl)pyrimidin-4-yl)-6-methyl-4-((5-methylthiophen-3-yl)methoxy)-2H-[1,4'-bipyridin]-2-one; |

| No. | Compound Name |
|---|---|
| 207. | 2'-(2-(2-hydroxypropan-2-yl)pyrimidin-4-yl)-3,6-dimethyl-4-((5-methylthiophen-3-yl)methoxy)-2H-[1,4'-bipyridin]-2-one; |
| 208. | 3-bromo-2'-(2-(2-hydroxypropan-2-yl)-5-methylpyrimidin-4-yl)-5',6-dimethyl-4-((5-methylthiophen-3-yl)methoxy)-2H-[1,4'-bipyridin]-2-one; |
| 209. | 3-chloro-2'-(2-(2-hydroxypropan-2-yl)-5-methylpyrimidin-4-yl)-5',6-dimethyl-4-((5-methylthiophen-3-yl)methoxy)-2H-[1,4'-bipyridin]-2-one; |
| 210. | 2'-(2-(2-hydroxypropan-2-yl)-5-methylpyrimidin-4-yl)-3,5',6-trimethyl-4-((5-methylthiophen-3-yl)methoxy)-2H-[1,4'-bipyridin]-2-one; |
| 211. | 3-bromo-5'-chloro-2'-(2-(2-hydroxypropan-2-yl)-5-methylpyrimidin-4-yl)-6-methyl-4-((5-methylthiophen-3-yl)methoxy)-2H-[1,4'-bipyridin]-2-one; |
| 212. | 3,5'-dichloro-2'-(2-(2-hydroxypropan-2-yl)-5-methylpyrimidin-4-yl)-6-methyl-4-((5-methylthiophen-3-yl)methoxy)-2H-[1,4'-bipyridin]-2-one; |
| 213. | 5'-chloro-2'-(2-(2-hydroxypropan-2-yl)-5-methylpyrimidin-4-yl)-3,6-dimethyl-4-((5-methylthiophen-3-yl)methoxy)-2H-[1,4'-bipyridin]-2-one; |
| 214. | 3-bromo-2'-(2-(2-hydroxypropan-2-yl)-5-methylpyrimidin-4-yl)-6-methyl-4-((5-methylthiophen-3-yl)methoxy)-2H-[1,4'-bipyridin]-2-one; |
| 215. | 3-chloro-2'-(2-(2-hydroxypropan-2-yl)-5-methylpyrimidin-4-yl)-6-methyl-4-((5-methylthiophen-3-yl)methoxy)-2H-[1,4'-bipyridin]-2-one; and |
| 216. | 2'-(2-(2-hydroxypropan-2-yl)-5-methylpyrimidin-4-yl)-3,6-dimethyl-4-((5-methylthiophen-3-yl)methoxy)-2H-[1,4'-bipyridin]-2-one. |

In another embodiment of the compounds of Formula (I), X is N and Y is CH; $R^1$ is selected from the group consisting of $C_1$-$C_3$-alkyl, bromo, chloro and fluoro; $R^2$ is alkoxy, optionally substituted with one or more heterocyclyl substituents optionally substituted with one or more substituents independently selected from the group consisting of $C_1$-$C_3$-alkyl and cyano; $R^3$ and $R^4$ are independently selected from the group consisting of —H and $C_1$-$C_3$-alkyl; and $R^5$ is heterocyclyl optionally substituted with one or more substituents independently selected from the group consisting of alkyl, hydroxyalkyl and aminoalkyl.

In another embodiment of the compounds of Formula (I), X is N and Y is CH; $R^1$ is methyl or chloro; $R^2$ is alkoxy, optionally substituted with five- or six-membered heteroaryl optionally substituted with one or more $C_1$-$C_3$-alkyl groups; $R^3$ is methyl; $R^4$ is —H or methyl; and $R^5$ is five- or six-membered heteroaryl optionally substituted with one or more substituents independently selected from the group consisting of alkyl and hydroxyalkyl.

In still another embodiment of the compounds of Formula (I), X is N and Y is CH; $R^1$ is methyl or chloro; $R^2$ is alkoxy substituted with five-membered heteroaryl optionally substituted with one or more methyl substituents; $R^3$ is methyl; $R^4$ is —H or methyl; and $R^5$ is pyridine or pyrimidine, wherein the pyridine or pyrimidine is optionally substituted with one or more substituents independently selected from the group consisting of alkyl and hydroxyalkyl.

The present invention is also directed to a subclass of compounds, including pharmaceutically acceptable salts of the compounds, wherein the compounds have the structure of Formula (III):

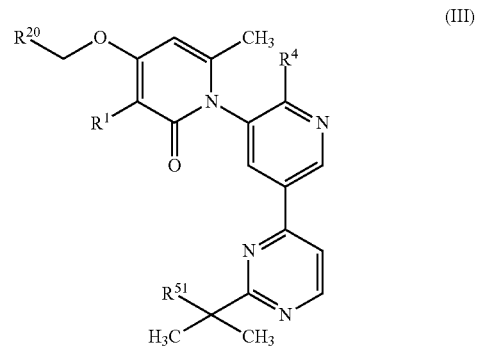

wherein:

$R^1$ is methyl or chloro;

$R^4$ is —H or methyl;

$R^{20}$ is five-membered heteroaryl optionally substituted with one or more methyl groups; and $R^{51}$ is methyl or hydroxy.

Non-limiting examples of Formula (III) compounds include the following compounds and pharmaceutically acceptable salts thereof:

| No. | Compound Name |
|---|---|
| 217. | 5'-(2-(2-hydroxypropan-2-yl)pyrimidin-4-yl)-2',3,6-trimethyl-4-((2-methyloxazol-4-yl)methoxy)-2H-[1,3'-bipyridin]-2-one; |
| 218. | 5'-(2-(2-hydroxypropan-2-yl)pyrimidin-4-yl)-2',3,6-trimethyl-4-((2-methylthiazol-4-yl)methoxy)-2H-[1,3'-bipyridin]-2-one; |
| 219. | 5'-(2-(2-hydroxypropan-2-yl)pyrimidin-4-yl)-2',3,6-trimethyl-4-((1-methyl-1H-pyrazol-3-yl)methoxy)-2H-[1,3'-bipyridin]-2-one; |

| No. | Compound Name |
|---|---|
| 220. | 3-chloro-5'-(2-(2-hydroxypropan-2-yl)pyrimidin-4-yl)-2',6-dimethyl-4-((2-methyloxazol-4-yl)methoxy)-2H-[1,3'-bipyridin]-2-one; |
| 221. | 3-chloro-5'-(2-(2-hydroxypropan-2-yl)pyrimidin-4-yl)-2',6-dimethyl-4-((2-methylthiazol-4-yl)methoxy)-2H-[1,3'-bipyridin]-2-one; |
| 222. | 3-chloro-5'-(2-(2-hydroxypropan-2-yl)pyrimidin-4-yl)-2',6-dimethyl-4-((1-methyl-1H-pyrazol-3-yl)methoxy)-2H-[1,3'-bipyridin]-2-one; |
| 223. | 3-chloro-5'-(2-(2-hydroxypropan-2-yl)pyrimidin-4-yl)-6-methyl-4-((2-methyloxazol-4-yl)methoxy)-2H-[1,3'-bipyridin]-2-one; |
| 224. | 3-chloro-5'-(2-(2-hydroxypropan-2-yl)pyrimidin-4-yl)-6-methyl-4-((2-methylthiazol-4-yl)methoxy)-2H-[1,3'-bipyridin]-2-one; |
| 225. | 3-chloro-5'-(2-(2-hydroxypropan-2-yl)pyrimidin-4-yl)-6-methyl-4-((1-methyl-1H-pyrazol-3-yl)methoxy)-2H-[1,3'-bipyridin]-2-one; |
| 226. | 5'-(2-(tert-butyl)pyrimidin-4-yl)-3-chloro-2',6-dimethyl-4-((2-methyloxazol-4-yl)methoxy)-2H-[1,3'-bipyridin]-2-one; |
| 227. | 5'-(2-(tert-butyl)pyrimidin-4-yl)-3-chloro-2',6-dimethyl-4-((2-methylthiazol-4-yl)methoxy)-2H-[1,3'-bipyridin]-2-one; |
| 228. | 5'-(2-(tert-butyl)pyrimidin-4-yl)-3-chloro-2',6-dimethyl-4-((1-methyl-1H-pyrazol-3-yl)methoxy)-2H-[1,3'-bipyridin]-2-one; |
| 229. | 5'-(2-(tert-butyl)pyrimidin-4-yl)-3-chloro-6-methyl-4-((2-methyloxazol-4-yl)methoxy)-2H-[1,3'-bipyridin]-2-one; |
| 230. | 5'-(2-(tert-butyl)pyrimidin-4-yl)-3-chloro-6-methyl-4-((2-methylthiazol-4-yl)methoxy)-2H-[1,3'-bipyridin]-2-one; and |
| 231. | 5'-(2-(tert-butyl)pyrimidin-4-yl)-3-chloro-6-methyl-4-((1-methyl-1H-pyrazol-3-yl)methoxy)-2H-[1,3'-bipyridin]-2-one. |

In another embodiment of the compounds of Formula (I), X is CH and Y is N; $R^1$ is selected from the group consisting of $C_1$-$C_3$-alkyl, bromo, chloro and fluoro; $R^2$ is alkoxy optionally substituted with one or more substituents selected from the group consisting of cycloalkyl and aryl; wherein the cycloalkyl or aryl is optionally substituted with one or more substituents independently selected from the group consisting of $C_1$-$C_3$-alkyl and halo; $R^3$ and $R^4$ are independently $C_1$-$C_3$-alkyl and —H; and $R^5$ is selected from the group consisting of heterocyclyl optionally substituted with one or more substituents independently selected from the group consisting of alkyl, hydroxyalkyl and aminoalkyl.

In another embodiment of the compounds of Formula (I), X is CH and Y is N; $R^1$ is methyl, bromo or chloro; $R^2$ is alkoxy optionally substituted with phenyl optionally substituted with one or more halo substituents; $R^3$ is methyl; $R^4$ is —H, chloro or methyl; and $R^5$ is five- or six-membered heteroaryl optionally substituted with one or more substituents independently selected from the group consisting of alkyl and hydroxyalkyl.

In another embodiment of the compounds of Formula (I), X is CH and Y is N; $R^1$ is methyl, bromo or chloro; $R^2$ is alkoxy substituted with phenyl optionally substituted with one or more substituents independently selected from the group consisting of chloro and fluoro; $R^3$ is methyl; $R^4$ is —H, chloro or methyl; and $R^5$ is pyridine or pyrimidine, wherein the pyridine and pyrimidine substituents is optionally substituted with one or more substituents independently selected from the group consisting of alkyl and hydroxyalkyl.

The present invention is also directed to a subclass of compounds, including pharmaceutically acceptable salts of the compounds, wherein the compounds have the structure of Formula (IV):

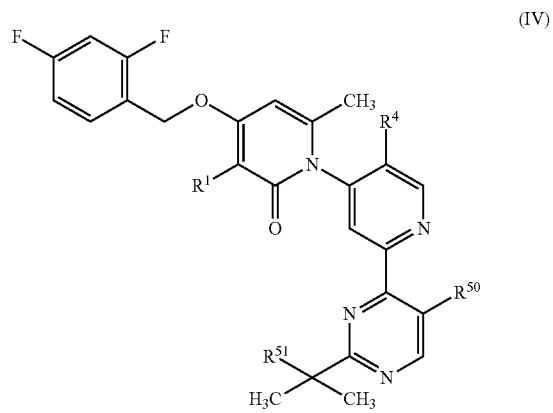

(IV)

wherein:

$R^1$ is methyl, bromo or chloro;

$R^4$ is —H, chloro or methyl;

$R^{50}$ is —H or methyl; and $R^{51}$ is —H, methyl or hydroxy.

Non-limiting examples of Formula (IV) compounds include the following compounds and pharmaceutically acceptable salts thereof:

| No. | Compound Name |
|---|---|
| 232. | 3-bromo-2'-(2-(tert-butyl)pyrimidin-4-yl)-4-((2,4-difluorobenzyl)oxy)-5',6-dimethyl-2H-[1,4'-bipyridin]-2-one; |
| 233. | 2'-(2-(tert-butyl)pyrimidin-4-yl)-4-((2,4-difluorobenzyl)oxy)-3,5',6-trimethyl-2H-[1,4'-bipyridin]-2-one; |
| 234. | 3-bromo-2'-(2-(tert-butyl)pyrimidin-4-yl)-5'-chloro-4-((2,4-difluorobenzyl)oxy)-6-methyl-2H-[1,4'-bipyridin]-2-one; |
| 235. | 2'-(2-(tert-butyl)pyrimidin-4-yl)-3,5'-dichloro-4-((2,4-difluorobenzyl)oxy)-6-methyl-2H-[1,4'-bipyridin]-2-one; |
| 236. | 2'-(2-(tert-butyl)pyrimidin-4-yl)-5'-chloro-4-((2,4-difluorobenzyl)oxy)-3,6-dimethyl-2H-[1,4'-bipyridin]-2-one; |
| 237. | 3-bromo-2'-(2-(tert-butyl)pyrimidin-4-yl)-4-((2,4-difluorobenzyl)oxy)-6-methyl-2H-[1,4'-bipyridin]-2-one; |
| 238. | 2'-(2-(tert-butyl)pyrimidin-4-yl)-3-chloro-4-((2,4-difluorobenzyl)oxy)-6-methyl-2H-[1,4'-bipyridin]-2-one; |
| 239. | 2'-(2-(tert-butyl)pyrimidin-4-yl)-4-((2,4-difluorobenzyl)oxy)-3,6-dimethyl-2H-[1,4'-bipyridin]-2-one; |
| 240. | 3-bromo-2'-(2-(tert-butyl)-5-methylpyrimidin-4-yl)-4-((2,4-difluorobenzyl)oxy)-5',6-dimethyl-2H-[1,4'-bipyridin]-2-one; |
| 241. | 2'-(2-(tert-butyl)-5-methylpyrimidin-4-yl)-3-chloro-4-((2,4-difluorobenzyl)oxy)-5',6-dimethyl-2H-[1,4'-bipyridin]-2-one; |
| 242. | 2'-(2-(tert-butyl)-5-methylpyrimidin-4-yl)-4-((2,4-difluorobenzyl)oxy)-3,5',6-trimethyl-2H-[1,4'-bipyridin]-2-one; |
| 243. | 3-bromo-2'-(2-(tert-butyl)-5-methylpyrimidin-4-yl)-5'-chloro-4-((2,4-difluorobenzyl)oxy)-6-methyl-2H-[1,4'-bipyridin]-2-one; |
| 244. | 2'-(2-(tert-butyl)-5-methylpyrimidin-4-yl)-3,5'-dichloro-4-((2,4-difluorobenzyl)oxy)-6-methyl-2H-[1,4'-bipyridin]-2-one; |
| 245. | 2'-(2-(tert-butyl)-5-methylpyrimidin-4-yl)-5'-chloro-4-((2,4-difluorobenzyl)oxy)-3,6-dimethyl-2H-[1,4'-bipyridin]-2-one; |
| 246. | 3-bromo-2'-(2-(tert-butyl)-5-methylpyrimidin-4-yl)-4-((2,4-difluorobenzyl)oxy)-6-methyl-2H-[1,4'-bipyridin]-2-one; |
| 247. | 2'-(2-(tert-butyl)-5-methylpyrimidin-4-yl)-3-chloro-4-((2,4-difluorobenzyl)oxy)-6-methyl-2H-[1,4'-bipyridin]-2-one; |
| 248. | 2'-(2-(tert-butyl)-5-methylpyrimidin-4-yl)-4-((2,4-difluorobenzyl)oxy)-3,6-dimethyl-2H-[1,4'-bipyridin]-2-one; |
| 249. | 3-bromo-4-((2,4-difluorobenzyl)oxy)-2'-(2-isopropylpyrimidin-4-yl)-5',6-dimethyl-2H-[1,4'-bipyridin]-2-one; |
| 250. | 3-chloro-4-((2,4-difluorobenzyl)oxy)-2'-(2-isopropylpyrimidin-4-yl)-5',6-dimethyl-2H-[1,4'-bipyridin]-2-one; |
| 251. | 4-((2,4-difluorobenzyl)oxy)-2'-(2-isopropylpyrimidin-4-yl)-3,5',6-trimethyl-2H-[1,4'-bipyridin]-2-one; |
| 252. | 3-bromo-5'-chloro-4-((2,4-difluorobenzyl)oxy)-2'-(2-isopropylpyrimidin-4-yl)-6-methyl-2H-[1,4'-bipyridin]-2-one; |
| 253. | 3,5'-dichloro-4-((2,4-difluorobenzyl)oxy)-2'-(2-isopropylpyrimidin-4-yl)-6-methyl-2H-[1,4'-bipyridin]-2-one; |
| 254. | 5'-chloro-4-((2,4-difluorobenzyl)oxy)-2'-(2-isopropylpyrimidin-4-yl)-3,6-dimethyl-2H-[1,4'-bipyridin]-2-one; |
| 255. | 3-bromo-4-((2,4-difluorobenzyl)oxy)-2'-(2-isopropylpyrimidin-4-yl)-6-methyl-2H-[1,4'-bipyridin]-2-one; |
| 256. | 3-chloro-4-((2,4-difluorobenzyl)oxy)-2'-(2-isopropylpyrimidin-4-yl)-6-methyl-2H-[1,4'-bipyridin]-2-one; |
| 257. | 4-((2,4-difluorobenzyl)oxy)-2'-(2-isopropylpyrimidin-4-yl)-3,6-dimethyl-2H-[1,4'-bipyridin]-2-one; |
| 258. | 3-bromo-4-((2,4-difluorobenzyl)oxy)-2'-(2-isopropyl-5-methylpyrimidin-4-yl)-5',6-dimethyl-2H-[1,4'-bipyridin]-2-one; |
| 259. | 3-chloro-4-((2,4-difluorobenzyl)oxy)-2'-(2-isopropyl-5-methylpyrimidin-4-yl)-5',6-dimethyl-2H-[1,4'-bipyridin]-2-one; |
| 260. | 4-((2,4-difluorobenzyl)oxy)-2'-(2-isopropyl-5-methylpyrimidin-4-yl)-3,5',6-trimethyl-2H-[1,4'-bipyridin]-2-one; |
| 261. | 3-bromo-5'-chloro-4-((2,4-difluorobenzyl)oxy)-2'-(2-isopropyl-5-methylpyrimidin-4-yl)-6-methyl-2H-[1,4'-bipyridin]-2-one; |
| 262. | 3,5'-dichloro-4-((2,4-difluorobenzyl)oxy)-2'-(2-isopropyl-5-methylpyrimidin-4-yl)-6-methyl-2H-[1,4'-bipyridin]-2-one; |
| 263. | 5'-chloro-4-((2,4-difluorobenzyl)oxy)-2'-(2-isopropyl-5-methylpyrimidin-4-yl)-3,6-dimethyl-2H-[1,4'-bipyridin]-2-one; |
| 264. | 3-bromo-4-((2,4-difluorobenzyl)oxy)-2'-(2-isopropyl-5-methylpyrimidin-4-yl)-6-methyl-2H-[1,4'-bipyridin]-2-one; |
| 265. | 3-chloro-4-((2,4-difluorobenzyl)oxy)-2'-(2-isopropyl-5-methylpyrimidin-4-yl)-6-methyl-2H-[1,4'-bipyridin]-2-one; |
| 266. | 4-((2,4-difluorobenzyl)oxy)-2'-(2-isopropyl-5-methylpyrimidin-4-yl)-3,6-dimethyl-2H-[1,4'-bipyridin]-2-one; |
| 267. | 3-bromo-4-((2,4-difluorobenzyl)oxy)-2'-(2-(2-hydroxypropan-2-yl)pyrimidin-4-yl)-5',6-dimethyl-2H-[1,4'-bipyridin]-2-one; |
| 268. | 3-bromo-5'-chloro-4-((2,4-difluorobenzyl)oxy)-2'-(2-(2-hydroxypropan-2-yl)pyrimidin-4-yl)-6-methyl-2H-[1,4'-bipyridin]-2-one; |
| 269. | 3,5'-dichloro-4-((2,4-difluorobenzyl)oxy)-2'-(2-(2-hydroxypropan-2-yl)pyrimidin-4-yl)-6-methyl-2H-[1,4'-bipyridin]-2-one; |
| 270. | 5'-chloro-4-((2,4-difluorobenzyl)oxy)-2'-(2-(2-hydroxypropan-2-yl)pyrimidin-4-yl)-3,6-dimethyl-2H-[1,4'-bipyridin]-2-one; |
| 271. | 3-bromo-4-((2,4-difluorobenzyl)oxy)-2'-(2-(2-hydroxypropan-2-yl)pyrimidin-4-yl)-6-methyl-2H-[1,4'-bipyridin]-2-one; |
| 272. | 3-chloro-4-((2,4-difluorobenzyl)oxy)-2'-(2-(2-hydroxypropan-2-yl)pyrimidin-4-yl)-6-methyl-2H-[1,4'-bipyridin]-2-one; |
| 273. | 4-((2,4-difluorobenzyl)oxy)-2'-(2-(2-hydroxypropan-2-yl)pyrimidin-4-yl)-3,6-dimethyl-2H-[1,4'-bipyridin]-2-one; |

| No. | Compound Name |
|---|---|
| 274. | 3-bromo-4-((2,4-difluorobenzyl)oxy)-2'-(2-(2-hydroxypropan-2-yl)-5-methylpyrimidin-4-yl)-5',6-dimethyl-2H-[1,4'-bipyridin]-2-one; |
| 275. | 3-chloro-4-((2,4-difluorobenzyl)oxy)-2'-(2-(2-hydroxypropan-2-yl)-5-methylpyrimidin-4-yl)-5',6-dimethyl-2H-[1,4'-bipyridin]-2-one; |
| 276. | 4-((2,4-difluorobenzyl)oxy)-2'-(2-(2-hydroxypropan-2-yl)-5-methylpyrimidin-4-yl)-3,5',6-trimethyl-2H-[1,4'-bipyridin]-2-one; |
| 277. | 3-bromo-5'-chloro-4-((2,4-difluorobenzyl)oxy)-2'-(2-(2-hydroxypropan-2-yl)-5-methylpyrimidin-4-yl)-6-methyl-2H-[1,4'-bipyridin]-2-one; |
| 278. | 3,5'-dichloro-4-((2,4-difluorobenzyl)oxy)-2'-(2-(2-hydroxypropan-2-yl)-5-methylpyrimidin-4-yl)-6-methyl-2H-[1,4'-bipyridin]-2-one; |
| 279. | 5'-chloro-4-((2,4-difluorobenzyl)oxy)-2'-(2-(2-hydroxypropan-2-yl)-5-methylpyrimidin-4-yl)-3,6-dimethyl-2H-[1,4'-bipyridin]-2-one; |
| 280. | 3-bromo-4-((2,4-difluorobenzyl)oxy)-2'-(2-(2-hydroxypropan-2-yl)-5-methylpyrimidin-4-yl)-6-methyl-2H-[1,4'-bipyridin]-2-one; |
| 281. | 3-chloro-4-((2,4-difluorobenzyl)oxy)-2'-(2-(2-hydroxypropan-2-yl)-5-methylpyrimidin-4-yl)-6-methyl-2H-[1,4'-bipyridin]-2-one; |
| 282. | 4-((2,4-difluorobenzyl)oxy)-2'-(2-(2-hydroxypropan-2-yl)-5-methylpyrimidin-4-yl)-3,6-dimethyl-2H-[1,4'-bipyridin]-2-one; |
| 283. | 4-((2,4-difluorobenzyl)oxy)-2'-(2-(2-hydroxypropan-2-yl)pyrimidin-4-yl)-3,5',6-trimethyl-2H-[1,4'-bipyridin]-2-one; |
| 284. | 3-chloro-4-((2,4-difluorobenzyl)oxy)-2'-(2-(2-hydroxypropan-2-yl)pyrimidin-4-yl)-5',6-dimethyl-2H-[1,4'-bipyridin]-2-one; |
| 285. | 2'-(2-(tert-butyl)pyrimidin-4-yl)-3-chloro-4-((2,4-difluorobenzyl)oxy)-5',6-dimethyl-2H-[1,4'-bipyridin]-2-one; |
| 286. | 3-chloro-4-((2,4-difluorobenzyl)oxy)-2''-(2-hydroxypropan-2-yl)-5',6-dimethyl-2H-[1,4':2',4''-terpyridin]-2-one; and |
| 287. | 2''-(tert-butyl)-3-chloro-4-((2,4-difluorobenzyl)oxy)-6-methyl-2H-[1,4':2',4''-terpyridin]-2-one. |

In another embodiment of the compounds of Formula (I), X is N and Y is CH; $R^1$ is selected from the group consisting of $C_1$-$C_3$-alkyl, bromo, chloro and fluoro; $R^2$ is alkoxy, optionally substituted with one or more substituents selected from the group consisting of cycloalkyl and aryl, wherein the cycloalkyl or aryl is optionally substituted with one or more substituents independently selected from the group consisting of $C_1$-$C_3$-alkyl and halo; $R^3$ and $R^4$ are independently $C_1$-$C_3$-alkyl and —H; and $R^5$ is heterocyclyl optionally substituted with one or more substituents independently selected from the group consisting of alkyl, hydroxyalkyl and aminoalkyl.

In another embodiment of the compounds of Formula (I), X is N and Y is CH; $R^1$ is methyl or chloro; $R^2$ is alkoxy optionally substituted with phenyl optionally substituted with one or more halo substituents; $R^3$ is methyl; $R^4$ is —H or methyl; and $R^5$ is five- or six-membered heteroaryl optionally substituted with one or more substituents independently selected from the group consisting of alkyl and hydroxyalkyl.

In still another embodiment of the compounds of Formula (I), X is N and Y is CH; $R^1$ is methyl or chloro; $R^2$ is alkoxy substituted with phenyl optionally substituted with one or more substituents independently selected from the group consisting of chloro and fluoro; $R^3$ is methyl; $R^4$ is —H or methyl; and $R^5$ is pyridine or pyrimidine which is optionally substituted with one or more substituents independently selected from the group consisting of alkyl and hydroxyalkyl.

The present invention is also directed to a subclass of compounds, including pharmaceutically acceptable salts of the compounds, wherein the compounds have the structure of Formula (V):

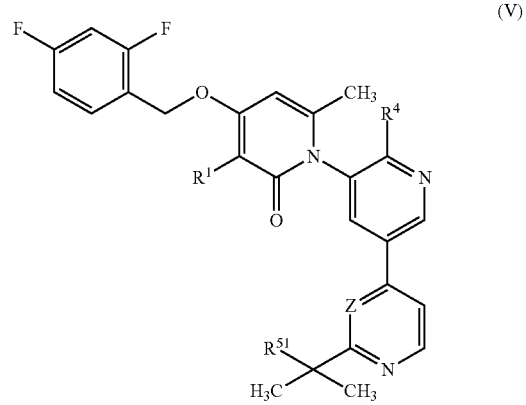

wherein:

Z is CH or N;

$R^1$ is methyl or chloro;

$R^4$ is —H or methyl; and $R^{51}$ is methyl or hydroxy.

Non-limiting examples of Formula (V) compounds include the following compounds and pharmaceutically acceptable salts thereof:

| No. | Compound Name |
|---|---|
| 288. | 4-((2,4-difluorobenzyl)oxy)-5'-(2-(2-hydroxypropan-2-yl)pyrimidin-4-yl)-3,6-dimethyl-2H-[1,3'-bipyridin]-2-one; |

| No. | Compound Name |
|---|---|
| 289. | 4-((2,4-difluorobenzyl)oxy)-5'-(2-(2-hydroxypropan-2-yl)pyrimidin-4-yl)-2',3,6-trimethyl-2H-[1,3'-bipyridin]-2-one; |
| 290. | 3-chloro-4-((2,4-difluorobenzyl)oxy)-5'-(2-(2-hydroxypropan-2-yl)pyrimidin-4-yl)-6-methyl-2H-[1,3'-bipyridin]-2-one; |
| 291. | 3-chloro-4-((2,4-difluorobenzyl)oxy)-5'-(2-(2-hydroxypropan-2-yl)pyrimidin-4-yl)-2',6-dimethyl-2H-[1,3'-bipyridin]-2-one; |
| 292. | 5'-(2-(tert-butyl)pyrimidin-4-yl)-3-chloro-4-((2,4-difluorobenzyl)oxy)-6-methyl-2H-[1,3'-bipyridin]-2-one; |
| 293. | 5'-(2-(tert-butyl)pyrimidin-4-yl)-3-chloro-4-((2,4-difluorobenzyl)oxy)-2',6-dimethyl-2H-[1,3'-bipyridin]-2-one; |
| 294. | 3-chloro-4-((2,4-difluorobenzyl)oxy)-2''-(2-hydroxypropan-2-yl)-6-methyl-2H-[1,3':5',4''-terpyridin]-2-one; |
| 295. | 3-chloro-4-((2,4-difluorobenzyl)oxy)-2''-(2-hydroxypropan-2-yl)-2',6-dimethyl-2H-[1,3':5',4''-terpyridin]-2-one; |
| 296. | 2''-(tert-butyl)-3-chloro-4-((2,4-difluorobenzyl)oxy)-6-methyl-2H-[1,3':5',4''-terpyridin]-2-one; and |
| 297. | 2''-(tert-butyl)-3-chloro-4-((2,4-difluorobenzyl)oxy)-2',6-dimethyl-2H-[1,3':5',4''-terpyridin]-2-one. |

In another embodiment of the compounds of Formula (I), X and Y are independently selected from the group consisting of CH and N, with the proviso that when X is CH, Y is N, and when X is N, Y is CH; $R^1$ is selected from the group consisting of $C_1$-$C_3$-alkyl, bromo, chloro and fluoro; $R^2$ is alkoxy optionally substituted with one or more substituents selected from the group consisting of cycloalkyl and aryl, wherein the cycloalkyl or aryl is optionally substituted with one or more substituents independently selected from the group consisting of $C_1$-$C_3$-alkyl and halo; $R^3$ and $R^4$ are independently $C_1$-$C_3$-alkyl, halo and —H; and $R^5$ is heterocyclyl optionally substituted with one or more substituents independently selected from the group consisting of alkyl, hydroxyalkyl and aminoalkyl.

In another embodiment of the compounds of Formula (I), X and Y are independently selected from the group consisting of CH and N, with the proviso that when X is CH, Y is N, and when X is N, Y is CH; $R^1$ is methyl, bromo or chloro; $R^2$ is alkoxy optionally substituted with phenyl optionally substituted with one or more halo substituents; $R^3$ is methyl; $R^4$ is —H, chloro or methyl; and $R^5$ is five- or six-membered heteroaryl optionally substituted with one or more substituents independently selected from the group consisting of alkyl and hydroxyalkyl.

In another embodiment of the compounds of Formula (I), X and Y are independently selected from the group consisting of CH and N, with the proviso that when X is CH, Y is N, and when X is N, Y is CH; $R^1$ is methyl, bromo or chloro; $R^2$ is alkoxy substituted with phenyl optionally substituted with one or more substituents independently selected from the group consisting of chloro and fluoro; $R^3$ is methyl; $R^4$ is —H, chloro or methyl; and $R^5$ is pyridine or pyrimidine, wherein the pyridine or pyrimidine is optionally substituted with one or more substituents independently selected from the group consisting of alkyl and hydroxyalkyl.

The present invention is also directed to a subclass of compounds, including pharmaceutically acceptable salts of the compounds, wherein the compounds have the structure of Formula (VI):

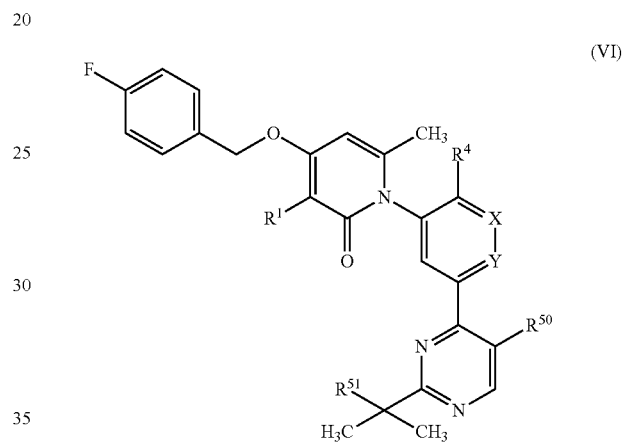

wherein

X and Y are independently selected from the group consisting of CH and N, with the proviso that when X is CH, Y is N, and when X is N, Y is CH;

$R^1$ is methyl, bromo or chloro;

$R^4$ is —H, chloro or methyl;

$R^{50}$ is —H or methyl; and $R^{51}$ is —H, methyl or hydroxy.

Non-limiting examples of Formula (VI) compounds include the following compounds and pharmaceutically acceptable salts thereof:

| No. | Compound Name |
|---|---|
| 298. | 3-bromo-2'-(2-(tert-butyl)pyrimidin-4-yl)-4-((4-fluorobenzyl)oxy)-5',6-dimethyl-2H-[1,4'-bipyridin]-2-one; |
| 299. | 2'-(2-(tert-butyl)pyrimidin-4-yl)-3-chloro-4-((4-fluorobenzyl)oxy)-5',6-dimethyl-2H-[1,4'-bipyridin]-2-one; |
| 300. | 2'-(2-(tert-butyl)pyrimidin-4-yl)-4-((4-fluorobenzyl)oxy)-3,5',6-trimethyl-2H-[1,4'-bipyridin]-2-one; |
| 301. | 3-bromo-2'-(2-(tert-butyl)pyrimidin-4-yl)-5'-chloro-4-((4-fluorobenzyl)oxy)-6-methyl-2H-[1,4'-bipyridin]-2-one; |
| 302. | 2'-(2-(tert-butyl)pyrimidin-4-yl)-3,5'-dichloro-4-((4-fluorobenzyl)oxy)-6-methyl-2H-[1,4'-bipyridin]-2-one; |
| 303. | 2'-(2-(tert-butyl)pyrimidin-4-yl)-5'-chloro-4-((4-fluorobenzyl)oxy)-3,6-dimethyl-2H-[1,4'-bipyridin]-2-one; |
| 304. | 3-bromo-2'-(2-(tert-butyl)pyrimidin-4-yl)-4-((4-fluorobenzyl)oxy)-6-methyl-2H-[1,4'-bipyridin]-2-one; |
| 305. | 2'-(2-(tert-butyl)pyrimidin-4-yl)-3-chloro-4-((4-fluorobenzyl)oxy)-6-methyl-2H-[1,4'-bipyridin]-2-one; |
| 306. | 2'-(2-(tert-butyl)pyrimidin-4-yl)-4-((4-fluorobenzyl)oxy)-3,6-dimethyl-2H-[1,4'-bipyridin]-2-one; |
| 307. | 3-bromo-2'-(2-(tert-butyl)-5-methylpyrimidin-4-yl)-4-((4-fluorobenzyl)oxy)-5',6-dimethyl-2H-[1,4'-bipyridin]-2-one; |
| 308. | 2'-(2-(tert-butyl)-5-methylpyrimidin-4-yl)-3-chloro-4-((4-fluorobenzyl)oxy)-5',6-dimethyl-2H-[1,4'-bipyridin]-2-one; |
| 309. | 2'-(2-(tert-butyl)-5-methylpyrimidin-4-yl)-4-((4-fluorobenzyl)oxy)-3,5',6-trimethyl-2H-[1,4'-bipyridin]-2-one; |
| 310. | 3-bromo-2'-(2-(tert-butyl)-5-methylpyrimidin-4-yl)-5'-chloro-4-((4-fluorobenzyl)oxy)-6-methyl-2H-[1,4'-bipyridin]-2-one; |
| 311. | 2'-(2-(tert-butyl)-5-methylpyrimidin-4-yl)-3,5'-dichloro-4-((4-fluorobenzyl)oxy)-6-methyl-2H-[1,4'-bipyridin]-2-one; |
| 312. | 2'-(2-(tert-butyl)-5-methylpyrimidin-4-yl)-5'-chloro-4-((4-fluorobenzyl)oxy)-3,6-dimethyl-2H-[1,4'-bipyridin]-2-one; |
| 313. | 3-bromo-2'-(2-(tert-butyl)-5-methylpyrimidin-4-yl)-4-((4-fluorobenzyl)oxy)-6-methyl-2H-[1,4'-bipyridin]-2-one; |
| 314. | 2'-(2-(tert-butyl)-5-methylpyrimidin-4-yl)-3-chloro-4-((4-fluorobenzyl)oxy)-6-methyl-2H-[1,4'-bipyridin]-2-one; |
| 315. | 2'-(2-(tert-butyl)-5-methylpyrimidin-4-yl)-4-((4-fluorobenzyl)oxy)-3,6-dimethyl-2H-[1,4'-bipyridin]-2-one; |
| 316. | 3-bromo-4-((4-fluorobenzyl)oxy)-2'-(2-isopropylpyrimidin-4-yl)-5',6-dimethyl-2H-[1,4'-bipyridin]-2-one; |
| 317. | 3-chloro-4-((4-fluorobenzyl)oxy)-2'-(2-isopropylpyrimidin-4-yl)-5',6-dimethyl-2H-[1,4'-bipyridin]-2-one; |
| 318. | 4-((4-fluorobenzyl)oxy)-2'-(2-isopropylpyrimidin-4-yl)-3,5',6-trimethyl-2H-[1,4'-bipyridin]-2-one; |
| 319. | 3-bromo-5'-chloro-4-((4-fluorobenzyl)oxy)-2'-(2-isopropylpyrimidin-4-yl)-6-methyl-2H-[1,4'-bipyridin]-2-one; |
| 320. | 3,5'-dichloro-4-((4-fluorobenzyl)oxy)-2'-(2-isopropylpyrimidin-4-yl)-6-methyl-2H-[1,4'-bipyridin]-2-one; |
| 321. | 5'-chloro-4-((4-fluorobenzyl)oxy)-2'-(2-isopropylpyrimidin-4-yl)-3,6-dimethyl-2H-[1,4'-bipyridin]-2-one; |
| 322. | 3-bromo-4-((4-fluorobenzyl)oxy)-2'-(2-isopropylpyrimidin-4-yl)-6-methyl-2H-[1,4'-bipyridin]-2-one; |
| 323. | 3-chloro-4-((4-fluorobenzyl)oxy)-2'-(2-isopropylpyrimidin-4-yl)-6-methyl-2H-[1,4'-bipyridin]-2-one; |
| 324. | 4-((4-fluorobenzyl)oxy)-2'-(2-isopropylpyrimidin-4-yl)-3,6-dimethyl-2H-[1,4'-bipyridin]-2-one; |
| 325. | 3-bromo-4-((4-fluorobenzyl)oxy)-2'-(2-isopropyl-5-methylpyrimidin-4-yl)-5',6-dimethyl-2H-[1,4'-bipyridin]-2-one; |
| 326. | 3-chloro-4-((4-fluorobenzyl)oxy)-2'-(2-isopropyl-5-methylpyrimidin-4-yl)-5',6-dimethyl-2H-[1,4'-bipyridin]-2-one; |
| 327. | 4-((4-fluorobenzyl)oxy)-2'-(2-isopropyl-5-methylpyrimidin-4-yl)-3,5',6-trimethyl-2H-[1,4'-bipyridin]-2-one; |
| 328. | 3-bromo-5'-chloro-4-((4-fluorobenzyl)oxy)-2'-(2-isopropyl-5-methylpyrimidin-4-yl)-6-methyl-2H-[1,4'-bipyridin]-2-one; |
| 329. | 3,5'-dichloro-4-((4-fluorobenzyl)oxy)-2'-(2-isopropyl-5-methylpyrimidin-4-yl)-6-methyl-2H-[1,4'-bipyridin]-2-one; |
| 330. | 5'-chloro-4-((4-fluorobenzyl)oxy)-2'-(2-isopropyl-5-methylpyrimidin-4-yl)-3,6-dimethyl-2H-[1,4'-bipyridin]-2-one; |
| 331. | 3-bromo-4-((4-fluorobenzyl)oxy)-2'-(2-isopropyl-5-methylpyrimidin-4-yl)-6-methyl-2H-[1,4'-bipyridin]-2-one; |
| 332. | 3-chloro-4-((4-fluorobenzyl)oxy)-2'-(2-isopropyl-5-methylpyrimidin-4-yl)-6-methyl-2H-[1,4'-bipyridin]-2-one; |
| 333. | 4-((4-fluorobenzyl)oxy)-2'-(2-isopropyl-5-methylpyrimidin-4-yl)-3,6-dimethyl-2H-[1,4'-bipyridin]-2-one; |
| 334. | 3-bromo-4-((4-fluorobenzyl)oxy)-2'-(2-(2-hydroxypropan-2-yl)pyrimidin-4-yl)-5',6-dimethyl-2H-[1,4'-bipyridin]-2-one; |
| 335. | 3-chloro-4-((4-fluorobenzyl)oxy)-2'-(2-(2-hydroxypropan-2-yl)pyrimidin-4-yl)-5',6-dimethyl-2H-[1,4'-bipyridin]-2-one; |
| 336. | 4-((4-fluorobenzyl)oxy)-2'-(2-(2-hydroxypropan-2-yl)pyrimidin-4-yl)-3,5',6-trimethyl-2H-[1,4'-bipyridin]-2-one; |
| 337. | 3-bromo-5'-chloro-4-((4-fluorobenzyl)oxy)-2'-(2-(2-hydroxypropan-2-yl)pyrimidin-4-yl)-6-methyl-2H-[1,4'-bipyridin]-2-one; |
| 338. | 3,5'-dichloro-4-((4-fluorobenzyl)oxy)-2'-(2-(2-hydroxypropan-2-yl)pyrimidin-4-yl)-6-methyl-2H-[1,4'-bipyridin]-2-one; |
| 339. | 5'-chloro-4-((4-fluorobenzyl)oxy)-2'-(2-(2-hydroxypropan-2-yl)pyrimidin-4-yl)-3,6-dimethyl-2H-[1,4'-bipyridin]-2-one; |
| 340. | 3-bromo-4-((4-fluorobenzyl)oxy)-2'-(2-(2-hydroxypropan-2-yl)pyrimidin-4-yl)-6-methyl-2H-[1,4'-bipyridin]-2-one; |
| 341. | 3-chloro-4-((4-fluorobenzyl)oxy)-2'-(2-(2-hydroxypropan-2-yl)pyrimidin-4-yl)-6-methyl-2H-[1,4'- |

| No. | Compound Name |
|---|---|
| | bipyridin]-2-one; |
| 342. | 4-((4-fluorobenzyl)oxy)-2'-(2-(2-hydroxypropan-2-yl)pyrimidin-4-yl)-3,6-dimethyl-2H-[1,4'-bipyridin]-2-one; |
| 343. | 3-bromo-4-((4-fluorobenzyl)oxy)-2'-(2-(2-hydroxypropan-2-yl)-5-methylpyrimidin-4-yl)-5',6-dimethyl-2H-[1,4'-bipyridin]-2-one; |
| 344. | 3-chloro-4-((4-fluorobenzyl)oxy)-2'-(2-(2-hydroxypropan-2-yl)-5-methylpyrimidin-4-yl)-5',6-dimethyl-2H-[1,4'-bipyridin]-2-one; |
| 345. | 4-((4-fluorobenzyl)oxy)-2'-(2-(2-hydroxypropan-2-yl)-5-methylpyrimidin-4-yl)-3,5',6-trimethyl-2H-[1,4'-bipyridin]-2-one; |
| 346. | 3-bromo-5'-chloro-4-((4-fluorobenzyl)oxy)-2'-(2-(2-hydroxypropan-2-yl)-5-methylpyrimidin-4-yl)-6-methyl-2H-[1,4'-bipyridin]-2-one; |
| 347. | 3,5'-dichloro-4-((4-fluorobenzyl)oxy)-2'-(2-(2-hydroxypropan-2-yl)-5-methylpyrimidin-4-yl)-6-methyl-2H-[1,4'-bipyridin]-2-one; |
| 348. | 5'-chloro-4-((4-fluorobenzyl)oxy)-2'-(2-(2-hydroxypropan-2-yl)-5-methylpyrimidin-4-yl)-3,6-dimethyl-2H-[1,4'-bipyridin]-2-one; |
| 349. | 3-bromo-4-((4-fluorobenzyl)oxy)-2'-(2-(2-hydroxypropan-2-yl)-5-methylpyrimidin-4-yl)-6-methyl-2H-[1,4'-bipyridin]-2-one; |
| 350. | 3-chloro-4-((4-fluorobenzyl)oxy)-2'-(2-(2-hydroxypropan-2-yl)-5-methylpyrimidin-4-yl)-6-methyl-2H-[1,4'-bipyridin]-2-one; and |
| 351. | 4-((4-fluorobenzyl)oxy)-2'-(2-(2-hydroxypropan-2-yl)-5-methylpyrimidin-4-yl)-3,6-dimethyl-2H-[1,4'-bipyridin]-2-one. |

In another embodiment of the compounds of Formula (I), X and Y are independently selected from the group consisting of CH and N, with the proviso that when X is CH, Y is N, and when X is N, Y is CH; $R^1$ is selected from the group consisting of $C_1$-$C_3$-alkyl, bromo, chloro and fluoro; $R^2$ is alkoxy optionally substituted with one or more substituents selected from the group consisting of cycloalkyl and aryl; wherein the cycloalkyl or aryl is optionally substituted with one or more substituents independently selected from the group consisting of $C_1$-$C_3$-alkyl and $C_1$-$C_3$-alkoxy; $R^3$ and $R^4$ are independently —H, $C_1$-$C_3$-alkyl, and halo; and $R^5$ is heterocyclyl optionally substituted with one or more substituents independently selected from the group consisting of alkyl, hydroxyalkyl and aminoalkyl.

In another embodiment of the compounds of Formula (I), X and Y are independently selected from the group consisting of CH and N, with the proviso that when X is CH, Y is N, and when X is N, Y is CH; $R^1$ is methyl, bromo or chloro; $R^2$ is alkoxy optionally substituted with phenyl optionally substituted with one or more substituents independently selected from the group consisting of $C_1$-$C_3$-alkyl and $C_1$-$C_3$-alkoxy; $R^3$ is methyl; $R^4$ is —H, chloro or methyl; and $R^5$ is five- or six-membered heteroaryl optionally substituted with one or more substituents independently selected from the group consisting of alkyl and hydroxyalkyl.

In another embodiment of the compounds of Formula (I), X and Y are independently selected from the group consisting of CH and N, with the proviso that when X is CH, Y is N, and when X is N, Y is CH; $R^1$ is methyl, bromo or chloro; $R^2$ is alkoxy, substituted with phenyl optionally substituted with one or more substituents independently selected from the group consisting of $C_1$-$C_3$-alkyl and $C_1$-$C_3$-alkoxy; $R^3$ is methyl; $R^4$ is —H, chloro or methyl; and $R^5$ is pyridine or pyrimidine, wherein the pyridine or pyrimidine is optionally substituted with one or more substituents independently selected from the group consisting of alkyl and hydroxyalkyl.

The present invention is also directed to a subclass of compounds, including pharmaceutically acceptable salts of the compounds, wherein the compounds have the structure of Formula (VII):

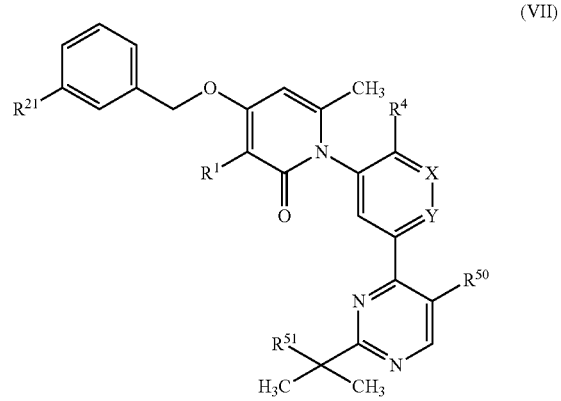

(VII)

wherein:

X and Y are independently selected from the group consisting of CH and N, with the proviso that when X is CH, Y is N, and when X is N, Y is CH;

$R^1$ is methyl, bromo or chloro;

$R^4$ is —H, chloro or methyl;

$R^{21}$ is methyl or methoxy;

$R^{50}$ is —H or methyl; and $R^{51}$ is —H, methyl or hydroxy.

Non-limiting examples of Formula (VII) compounds include the following compounds and pharmaceutically acceptable salts thereof:

| No. | Compound Name |
|---|---|
| 352. | 3-bromo-2'-(2-(tert-butyl)pyrimidin-4-yl)-5',6-dimethyl-4-((3-methylbenzyl)oxy)-2H-[1,4'-bipyridin]-2-one; |
| 353. | 2'-(2-(tert-butyl)pyrimidin-4-yl)-3-chloro-5',6-dimethyl-4-((3-methylbenzyl)oxy)-2H-[1,4'-bipyridin]-2-one; |
| 354. | 2'-(2-(tert-butyl)pyrimidin-4-yl)-3,5',6-trimethyl-4-((3-methylbenzyl)oxy)-2H-[1,4'-bipyridin]-2-one; |

| No. | Compound Name |
|---|---|
| 355. | 3-bromo-2'-(2-(tert-butyl)pyrimidin-4-yl)-5'-chloro-6-methyl-4-((3-methylbenzyl)oxy)-2H-[1,4'-bipyridin]-2-one; |
| 356. | 2'-(2-(tert-butyl)pyrimidin-4-yl)-3,5'-dichloro-6-methyl-4-((3-methylbenzyl)oxy)-2H-[1,4'-bipyridin]-2-one; |
| 357. | 2'-(2-(tert-butyl)pyrimidin-4-yl)-5'-chloro-3,6-dimethyl-4-((3-methylbenzyl)oxy)-2H-[1,4'-bipyridin]-2-one; |
| 358. | 3-bromo-2'-(2-(tert-butyl)pyrimidin-4-yl)-6-methyl-4-((3-methylbenzyl)oxy)-2H-[1,4'-bipyridin]-2-one; |
| 359. | 2'-(2-(tert-butyl)pyrimidin-4-yl)-3-chloro-6-methyl-4-((3-methylbenzyl)oxy)-2H-[1,4'-bipyridin]-2-one; |
| 360. | 2'-(2-(tert-butyl)pyrimidin-4-yl)-3,6-dimethyl-4-((3-methylbenzyl)oxy)-2H-[1,4'-bipyridin]-2-one; |
| 361. | 3-bromo-2'-(2-(tert-butyl)-5-methylpyrimidin-4-yl)-5',6-dimethyl-4-((3-methylbenzyl)oxy)-2H-[1,4'-bipyridin]-2-one; |
| 362. | 2'-(2-(tert-butyl)-5-methylpyrimidin-4-yl)-3-chloro-5',6-dimethyl-4-((3-methylbenzyl)oxy)-2H-[1,4'-bipyridin]-2-one; |
| 363. | 2'-(2-(tert-butyl)-5-methylpyrimidin-4-yl)-3,5',6-trimethyl-4-((3-methylbenzyl)oxy)-2H-[1,4'-bipyridin]-2-one; |
| 364. | 3-bromo-2'-(2-(tert-butyl)-5-methylpyrimidin-4-yl)-5'-chloro-6-methyl-4-((3-methylbenzyl)oxy)-2H-[1,4'-bipyridin]-2-one; |
| 365. | 2'-(2-(tert-butyl)-5-methylpyrimidin-4-yl)-3,5'-dichloro-6-methyl-4-((3-methylbenzyl)oxy)-2H-[1,4'-bipyridin]-2-one; |
| 366. | 2'-(2-(tert-butyl)-5-methylpyrimidin-4-yl)-5'-chloro-3,6-dimethyl-4-((3-methylbenzyl)oxy)-2H-[1,4'-bipyridin]-2-one; |
| 367. | 3-bromo-2'-(2-(tert-butyl)-5-methylpyrimidin-4-yl)-6-methyl-4-((3-methylbenzyl)oxy)-2H-[1,4'-bipyridin]-2-one; |
| 368. | 2'-(2-(tert-butyl)-5-methylpyrimidin-4-yl)-3-chloro-6-methyl-4-((3-methylbenzyl)oxy)-2H-[1,4'-bipyridin]-2-one; |
| 369. | 2'-(2-(tert-butyl)-5-methylpyrimidin-4-yl)-3,6-dimethyl-4-((3-methylbenzyl)oxy)-2H-[1,4'-bipyridin]-2-one; |
| 370. | 3-bromo-2'-(2-isopropylpyrimidin-4-yl)-5',6-dimethyl-4-((3-methylbenzyl)oxy)-2H-[1,4'-bipyridin]-2-one; |
| 371. | 3-chloro-2'-(2-isopropylpyrimidin-4-yl)-5',6-dimethyl-4-((3-methylbenzyl)oxy)-2H-[1,4'-bipyridin]-2-one; |
| 372. | 2'-(2-isopropylpyrimidin-4-yl)-3,5',6-trimethyl-4-((3-methylbenzyl)oxy)-2H-[1,4'-bipyridin]-2-one; |
| 373. | 3-bromo-5'-chloro-2'-(2-isopropylpyrimidin-4-yl)-6-methyl-4-((3-methylbenzyl)oxy)-2H-[1,4'-bipyridin]-2-one; |
| 374. | 3,5'-dichloro-2'-(2-isopropylpyrimidin-4-yl)-6-methyl-4-((3-methylbenzyl)oxy)-2H-[1,4'-bipyridin]-2-one; |
| 375. | 5'-chloro-2'-(2-isopropylpyrimidin-4-yl)-3,6-dimethyl-4-((3-methylbenzyl)oxy)-2H-[1,4'-bipyridin]-2-one; |
| 376. | 3-bromo-2'-(2-isopropylpyrimidin-4-yl)-6-methyl-4-((3-methylbenzyl)oxy)-2H-[1,4'-bipyridin]-2-one; |
| 377. | 3-chloro-2'-(2-isopropylpyrimidin-4-yl)-6-methyl-4-((3-methylbenzyl)oxy)-2H-[1,4'-bipyridin]-2-one; |
| 378. | 2'-(2-isopropylpyrimidin-4-yl)-3,6-dimethyl-4-((3-methylbenzyl)oxy)-2H-[1,4'-bipyridin]-2-one; |
| 379. | 3-bromo-2'-(2-isopropyl-5-methylpyrimidin-4-yl)-5',6-dimethyl-4-((3-methylbenzyl)oxy)-2H-[1,4'-bipyridin]-2-one; |
| 380. | 3-chloro-2'-(2-isopropyl-5-methylpyrimidin-4-yl)-5',6-dimethyl-4-((3-methylbenzyl)oxy)-2H-[1,4'-bipyridin]-2-one; |
| 381. | 2'-(2-isopropyl-5-methylpyrimidin-4-yl)-3,5',6-trimethyl-4-((3-methylbenzyl)oxy)-2H-[1,4'-bipyridin]-2-one; |
| 382. | 3-bromo-5'-chloro-2'-(2-isopropyl-5-methylpyrimidin-4-yl)-6-methyl-4-((3-methylbenzyl)oxy)-2H-[1,4'-bipyridin]-2-one; |
| 383. | 3,5'-dichloro-2'-(2-isopropyl-5-methylpyrimidin-4-yl)-6-methyl-4-((3-methylbenzyl)oxy)-2H-[1,4'-bipyridin]-2-one; |
| 384. | 5'-chloro-2'-(2-isopropyl-5-methylpyrimidin-4-yl)-3,6-dimethyl-4-((3-methylbenzyl)oxy)-2H-[1,4'-bipyridin]-2-one; |
| 385. | 3-bromo-2'-(2-isopropyl-5-methylpyrimidin-4-yl)-6-methyl-4-((3-methylbenzyl)oxy)-2H-[1,4'-bipyridin]-2-one; |
| 386. | 3-chloro-2'-(2-isopropyl-5-methylpyrimidin-4-yl)-6-methyl-4-((3-methylbenzyl)oxy)-2H-[1,4'-bipyridin]-2-one; |
| 387. | 2'-(2-isopropyl-5-methylpyrimidin-4-yl)-3,6-dimethyl-4-((3-methylbenzyl)oxy)-2H-[1,4'-bipyridin]-2-one; |
| 388. | 3-bromo-2'-(2-(2-hydroxypropan-2-yl)pyrimidin-4-yl)-5',6-dimethyl-4-((3-methylbenzyl)oxy)-2H-[1,4'-bipyridin]-2-one; |
| 389. | 3-chloro-2'-(2-(2-hydroxypropan-2-yl)pyrimidin-4-yl)-5',6-dimethyl-4-((3-methylbenzyl)oxy)-2H-[1,4'-bipyridin]-2-one; |
| 390. | 2'-(2-(2-hydroxypropan-2-yl)pyrimidin-4-yl)-3,5',6-trimethyl-4-((3-methylbenzyl)oxy)-2H-[1,4'-bipyridin]-2-one; |
| 391. | 3-bromo-5'-chloro-2'-(2-(2-hydroxypropan-2-yl)pyrimidin-4-yl)-6-methyl-4-((3-methylbenzyl)oxy)-2H-[1,4'-bipyridin]-2-one; |
| 392. | 3,5'-dichloro-2'-(2-(2-hydroxypropan-2-yl)pyrimidin-4-yl)-6-methyl-4-((3-methylbenzyl)oxy)-2H-[1,4'-bipyridin]-2-one; |
| 393. | 5'-chloro-2'-(2-(2-hydroxypropan-2-yl)pyrimidin-4-yl)-3,6-dimethyl-4-((3-methylbenzyl)oxy)-2H-[1,4'-bipyridin]-2-one; |
| 394. | 3-bromo-2'-(2-(2-hydroxypropan-2-yl)pyrimidin-4-yl)-6-methyl-4-((3-methylbenzyl)oxy)-2H-[1,4'-bipyridin]-2-one; |
| 395. | 3-chloro-2'-(2-(2-hydroxypropan-2-yl)pyrimidin-4-yl)-6-methyl-4-((3-methylbenzyl)oxy)-2H-[1,4'-bipyridin]-2-one; |
| 396. | 2'-(2-(2-hydroxypropan-2-yl)pyrimidin-4-yl)-3,6-dimethyl-4-((3-methylbenzyl)oxy)-2H-[1,4'-bipyridin]-2-one; |

| No. | Compound Name |
|---|---|
| 397. | 3-bromo-2'-(2-(2-hydroxypropan-2-yl)-5-methylpyrimidin-4-yl)-5',6-dimethyl-4-((3-methylbenzyl)oxy)-2H-[1,4'-bipyridin]-2-one; |
| 398. | 3-chloro-2'-(2-(2-hydroxypropan-2-yl)-5-methylpyrimidin-4-yl)-5',6-dimethyl-4-((3-methylbenzyl)oxy)-2H-[1,4'-bipyridin]-2-one; |
| 399. | 2'-(2-(2-hydroxypropan-2-yl)-5-methylpyrimidin-4-yl)-3,5',6-trimethyl-4-((3-methylbenzyl)oxy)-2H-[1,4'-bipyridin]-2-one; |
| 400. | 3-bromo-5'-chloro-2'-(2-(2-hydroxypropan-2-yl)-5-methylpyrimidin-4-yl)-6-methyl-4-((3-methylbenzyl)oxy)-2H-[1,4'-bipyridin]-2-one; |
| 401. | 3,5'-dichloro-2'-(2-(2-hydroxypropan-2-yl)-5-methylpyrimidin-4-yl)-6-methyl-4-((3-methylbenzyl)oxy)-2H-[1,4'-bipyridin]-2-one; |
| 402. | 5'-chloro-2'-(2-(2-hydroxypropan-2-yl)-5-methylpyrimidin-4-yl)-3,6-dimethyl-4-((3-methylbenzyl)oxy)-2H-[1,4'-bipyridin]-2-one; |
| 403. | 3-bromo-2'-(2-(2-hydroxypropan-2-yl)-5-methylpyrimidin-4-yl)-6-methyl-4-((3-methylbenzyl)oxy)-2H-[1,4'-bipyridin]-2-one; |
| 404. | 3-chloro-2'-(2-(2-hydroxypropan-2-yl)-5-methylpyrimidin-4-yl)-6-methyl-4-((3-methylbenzyl)oxy)-2H-[1,4'-bipyridin]-2-one; and |
| 405. | 2'-(2-(2-hydroxypropan-2-yl)-5-methylpyrimidin-4-yl)-3,6-dimethyl-4-((3-methylbenzyl)oxy)-2H-[1,4'-bipyridin]-2-one. |
| 406. | 3-bromo-2'-(2-(tert-butyl)pyrimidin-4-yl)-4-((3-methoxybenzyl)oxy)-5',6-dimethyl-2H-[1,4'-bipyridin]-2-one; |
| 407. | 2'-(2-(tert-butyl)pyrimidin-4-yl)-3-chloro-4-((3-methoxybenzyl)oxy)-5',6-dimethyl-2H-[1,4'-bipyridin]-2-one; |
| 408. | 2'-(2-(tert-butyl)pyrimidin-4-yl)-4-((3-methoxybenzyl)oxy)-3,5',6-trimethyl-2H-[1,4'-bipyridin]-2-one; |
| 409. | 3-bromo-2'-(2-(tert-butyl)pyrimidin-4-yl)-5'-chloro-4-((3-methoxybenzyl)oxy)-6-methyl-2H-[1,4'-bipyridin]-2-one; |
| 410. | 2'-(2-(tert-butyl)pyrimidin-4-yl)-3,5'-dichloro-4-((3-methoxybenzyl)oxy)-6-methyl-2H-[1,4'-bipyridin]-2-one; |
| 411. | 2'-(2-(tert-butyl)pyrimidin-4-yl)-5'-chloro-4-((3-methoxybenzyl)oxy)-3,6-dimethyl-2H-[1,4'-bipyridin]-2-one; |
| 412. | 3-bromo-2'-(2-(tert-butyl)pyrimidin-4-yl)-4-((3-methoxybenzyl)oxy)-6-methyl-2H-[1,4'-bipyridin]-2-one; |
| 413. | 2'-(2-(tert-butyl)pyrimidin-4-yl)-3-chloro-4-((3-methoxybenzyl)oxy)-6-methyl-2H-[1,4'-bipyridin]-2-one; |
| 414. | 2'-(2-(tert-butyl)pyrimidin-4-yl)-4-((3-methoxybenzyl)oxy)-3,6-dimethyl-2H-[1,4'-bipyridin]-2-one; |
| 415. | 3-bromo-2'-(2-(tert-butyl)-5-methylpyrimidin-4-yl)-4-((3-methoxybenzyl)oxy)-5',6-dimethyl-2H-[1,4'-bipyridin]-2-one; |
| 416. | 2'-(2-(tert-butyl)-5-methylpyrimidin-4-yl)-3-chloro-4-((3-methoxybenzyl)oxy)-5',6-dimethyl-2H-[1,4'-bipyridin]-2-one; |
| 417. | 2'-(2-(tert-butyl)-5-methylpyrimidin-4-yl)-4-((3-methoxybenzyl)oxy)-3,5',6-trimethyl-2H-[1,4'-bipyridin]-2-one; |
| 418. | 3-bromo-2'-(2-(tert-butyl)-5-methylpyrimidin-4-yl)-5'-chloro-4-((3-methoxybenzyl)oxy)-6-methyl-2H-[1,4'-bipyridin]-2-one; |
| 419. | 2'-(2-(tert-butyl)-5-methylpyrimidin-4-yl)-3,5'-dichloro-4-((3-methoxybenzyl)oxy)-6-methyl-2H-[1,4'-bipyridin]-2-one; |
| 420. | 2'-(2-(tert-butyl)-5-methylpyrimidin-4-yl)-5'-chloro-4-((3-methoxybenzyl)oxy)-3,6-dimethyl-2H-[1,4'-bipyridin]-2-one; |
| 421. | 3-bromo-2'-(2-(tert-butyl)-5-methylpyrimidin-4-yl)-4-((3-methoxybenzyl)oxy)-6-methyl-2H-[1,4'-bipyridin]-2-one; |
| 422. | 2'-(2-(tert-butyl)-5-methylpyrimidin-4-yl)-3-chloro-4-((3-methoxybenzyl)oxy)-6-methyl-2H-[1,4'-bipyridin]-2-one; |
| 423. | 2'-(2-(tert-butyl)-5-methylpyrimidin-4-yl)-4-((3-methoxybenzyl)oxy)-3,6-dimethyl-2H-[1,4'-bipyridin]-2-one; |
| 424. | 3-bromo-2'-(2-isopropylpyrimidin-4-yl)-4-((3-methoxybenzyl)oxy)-5',6-dimethyl-2H-[1,4'-bipyridin]-2-one; |
| 425. | 3-chloro-2'-(2-isopropylpyrimidin-4-yl)-4-((3-methoxybenzyl)oxy)-5',6-dimethyl-2H-[1,4'-bipyridin]-2-one; |
| 426. | 2'-(2-isopropylpyrimidin-4-yl)-4-((3-methoxybenzyl)oxy)-3,5',6-trimethyl-2H-[1,4'-bipyridin]-2-one; |
| 427. | 3-bromo-5'-chloro-2'-(2-isopropylpyrimidin-4-yl)-4-((3-methoxybenzyl)oxy)-6-methyl-2H-[1,4'-bipyridin]-2-one; |
| 428. | 3,5'-dichloro-2'-(2-isopropylpyrimidin-4-yl)-4-((3-methoxybenzyl)oxy)-6-methyl-2H-[1,4'-bipyridin]-2-one; |
| 429. | 5'-chloro-2'-(2-isopropylpyrimidin-4-yl)-4-((3-methoxybenzyl)oxy)-3,6-dimethyl-2H-[1,4'-bipyridin]-2-one; |
| 430. | 3-bromo-2'-(2-isopropylpyrimidin-4-yl)-4-((3-methoxybenzyl)oxy)-6-methyl-2H-[1,4'-bipyridin]-2-one; |
| 431. | 3-chloro-2'-(2-isopropylpyrimidin-4-yl)-4-((3-methoxybenzyl)oxy)-6-methyl-2H-[1,4'-bipyridin]-2-one; |
| 432. | 2'-(2-isopropylpyrimidin-4-yl)-4-((3-methoxybenzyl)oxy)-3,6-dimethyl-2H-[1,4'-bipyridin]-2-one; |
| 433. | 3-bromo-2'-(2-isopropyl-5-methylpyrimidin-4-yl)-4-((3-methoxybenzyl)oxy)-5',6-dimethyl-2H-[1,4'-bipyridin]-2-one; |
| 434. | 3-chloro-2'-(2-isopropyl-5-methylpyrimidin-4-yl)-4-((3-methoxybenzyl)oxy)-5',6-dimethyl-2H-[1,4'-bipyridin]-2-one; |
| 435. | 2'-(2-isopropyl-5-methylpyrimidin-4-yl)-4-((3-methoxybenzyl)oxy)-3,5',6-trimethyl-2H-[1,4'-bipyridin]-2-one; |
| 436. | 3-bromo-5'-chloro-2'-(2-isopropyl-5-methylpyrimidin-4-yl)-4-((3-methoxybenzyl)oxy)-6-methyl-2H-[1,4'-bipyridin]-2-one; |
| 437. | 3,5'-dichloro-2'-(2-isopropyl-5-methylpyrimidin-4-yl)-4-((3-methoxybenzyl)oxy)-6-methyl-2H-[1,4'- |

| No. | Compound Name |
|---|---|
| | bipyridin]-2-one; |
| 438. | 5'-chloro-2'-(2-isopropyl-5-methylpyrimidin-4-yl)-4-((3-methoxybenzyl)oxy)-3,6-dimethyl-2H-[1,4'-bipyridin]-2-one; |
| 439. | 3-bromo-2'-(2-isopropyl-5-methylpyrimidin-4-yl)-4-((3-methoxybenzyl)oxy)-6-methyl-2H-[1,4'-bipyridin]-2-one; |
| 440. | 3-chloro-2'-(2-isopropyl-5-methylpyrimidin-4-yl)-4-((3-methoxybenzyl)oxy)-6-methyl-2H-[1,4'-bipyridin]-2-one; |
| 441. | 2'-(2-isopropyl-5-methylpyrimidin-4-yl)-4-((3-methoxybenzyl)oxy)-3,6-dimethyl-2H-[1,4'-bipyridin]-2-one; |
| 442. | 3-bromo-2'-(2-(2-hydroxypropan-2-yl)pyrimidin-4-yl)-4-((3-methoxybenzyl)oxy)-5',6-dimethyl-2H-[1,4'-bipyridin]-2-one; |
| 443. | 3-chloro-2'-(2-(2-hydroxypropan-2-yl)pyrimidin-4-yl)-4-((3-methoxybenzyl)oxy)-5',6-dimethyl-2H-[1,4'-bipyridin]-2-one; |
| 444. | 2'-(2-(2-hydroxypropan-2-yl)pyrimidin-4-yl)-4-((3-methoxybenzyl)oxy)-3,5',6-trimethyl-2H-[1,4'-bipyridin]-2-one; |
| 445. | 3-bromo-5'-chloro-2'-(2-(2-hydroxypropan-2-yl)pyrimidin-4-yl)-4-((3-methoxybenzyl)oxy)-6-methyl-2H-[1,4'-bipyridin]-2-one; |
| 446. | 3,5'-dichloro-2'-(2-(2-hydroxypropan-2-yl)pyrimidin-4-yl)-4-((3-methoxybenzyl)oxy)-6-methyl-2H-[1,4'-bipyridin]-2-one; |
| 447. | 5'-chloro-2'-(2-(2-hydroxypropan-2-yl)pyrimidin-4-yl)-4-((3-methoxybenzyl)oxy)-3,6-dimethyl-2H-[1,4'-bipyridin]-2-one; |
| 448. | 3-bromo-2'-(2-(2-hydroxypropan-2-yl)pyrimidin-4-yl)-4-((3-methoxybenzyl)oxy)-6-methyl-2H-[1,4'-bipyridin]-2-one; |
| 449. | 3-chloro-2'-(2-(2-hydroxypropan-2-yl)pyrimidin-4-yl)-4-((3-methoxybenzyl)oxy)-6-methyl-2H-[1,4'-bipyridin]-2-one; |
| 450. | 2'-(2-(2-hydroxypropan-2-yl)pyrimidin-4-yl)-4-((3-methoxybenzyl)oxy)-3,6-dimethyl-2H-[1,4'-bipyridin]-2-one; |
| 451. | 3-bromo-2'-(2-(2-hydroxypropan-2-yl)-5-methylpyrimidin-4-yl)-4-((3-methoxybenzyl)oxy)-5',6-dimethyl-2H-[1,4'-bipyridin]-2-one; |
| 452. | 3-chloro-2'-(2-(2-hydroxypropan-2-yl)-5-methylpyrimidin-4-yl)-4-((3-methoxybenzyl)oxy)-5',6-dimethyl-2H-[1,4'-bipyridin]-2-one; |
| 453. | 2'-(2-(2-hydroxypropan-2-yl)-5-methylpyrimidin-4-yl)-4-((3-methoxybenzyl)oxy)-3,5',6-trimethyl-2H-[1,4'-bipyridin]-2-one; |
| 454. | 3-bromo-5'-chloro-2'-(2-(2-hydroxypropan-2-yl)-5-methylpyrimidin-4-yl)-4-((3-methoxybenzyl)oxy)-6-methyl-2H-[1,4'-bipyridin]-2-one; |
| 455. | 3,5'-dichloro-2'-(2-(2-hydroxypropan-2-yl)-5-methylpyrimidin-4-yl)-4-((3-methoxybenzyl)oxy)-6-methyl-2H-[1,4'-bipyridin]-2-one; |
| 456. | 5'-chloro-2'-(2-(2-hydroxypropan-2-yl)-5-methylpyrimidin-4-yl)-4-((3-methoxybenzyl)oxy)-3,6-dimethyl-2H-[1,4'-bipyridin]-2-one; |
| 457. | 3-chloro-2'-(2-(2-hydroxypropan-2-yl)-5-methylpyrimidin-4-yl)-4-((3-methoxybenzyl)oxy)-6-methyl-2H-[1,4'-bipyridin]-2-one; |
| 458. | 3-chloro-2'-(2-(2-hydroxypropan-2-yl)-5-methylpyrimidin-4-yl)-4-((3-methoxybenzyl)oxy)-6-methyl-2H-[1,4'-bipyridin]-2-one; and |
| 459. | 2'-(2-(2-hydroxypropan-2-yl)-5-methylpyrimidin-4-yl)-4-((3-methoxybenzyl)oxy)-3,6-dimethyl-2H-[1,4'-bipyridin]-2-one. |

In another embodiment of the compounds of Formula (I), X and Y are independently selected from the group consisting of CH and N, with the proviso that when X is CH, Y is N, and when X is N, Y is CH; $R^1$ is selected from the group consisting of $C_1$-$C_3$-alkyl, bromo, chloro and fluoro; $R^2$ is alkoxy, optionally substituted with one or more heterocyclyl substituents optionally substituted with one or more substituents independently selected from the group consisting of $C_1$-$C_3$-alkyl, $C_1$-$C_3$-alkoxy and cyano; $R^3$ is $C_1$-$C_3$-alkyl; $R^4$ is selected from the group consisting of —H, $C_1$-$C_3$-alkyl, bromo, chloro and fluoro; and $R^5$ is heterocyclyl optionally substituted with one or more substituents independently selected from the group consisting of alkyl, hydroxyalkyl and aminoalkyl.

In another embodiment of the compounds of Formula (I), X and Y are independently selected from the group consisting of CH and N, with the proviso that when X is CH, Y is N, and when X is N, Y is CH; $R^1$ is methyl, bromo or chloro; $R^2$ is alkoxy optionally substituted with five- or six-membered heteroaryl optionally substituted with one or more substituents independently selected from the group consisting of $C_1$-$C_3$-alkyl and $C_1$-$C_3$-alkoxy; $R^3$ is methyl; $R^4$ is —H, methyl or chloro; and $R^5$ is five- or six-membered heteroaryl optionally substituted with one or more substituents independently selected from the group consisting of alkyl and hydroxyalkyl.

In another embodiment of the compounds of Formula (I), X and Y are independently selected from the group consisting of CH and N, with the proviso that when X is CH, Y is N, and when X is N, Y is CH; $R^1$ is methyl, bromo or chloro; $R^2$ is alkoxy substituted with six-membered heteroaryl optionally substituted with one or more methyl substituents independently selected from the group consisting of $C_1$-$C_3$-alkyl and $C_1$-$C_3$-alkoxy; $R^3$ is methyl; $R^4$ is —H, methyl or chloro; and $R^5$ is pyridine or pyrimidine, wherein the pyridine or pyrimidine is optionally substituted with one or more substituents independently selected from the group consisting of alkyl and hydroxyalkyl.

The present invention is also directed to a subclass of compounds, including pharmaceutically acceptable salts of the compounds, wherein the compounds have the structure of Formula (VIII):

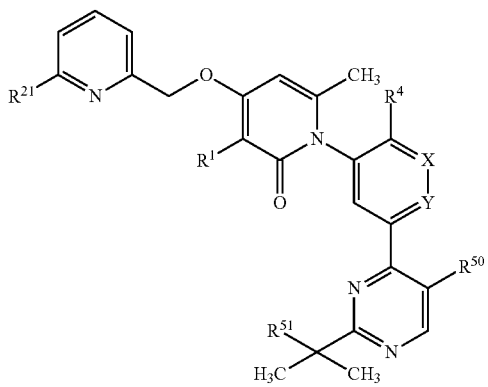

(VIII)

wherein:

X and Y are independently selected from the group consisting of CH and N, with the proviso that when X is CH, Y is N, and when X is N, Y is CH;

$R^1$ is methyl, bromo or chloro;

$R^4$ is —H, methyl or chloro;

$R^{21}$ is methyl or methoxy;

$R^{50}$ is —H or methyl; and $R^{51}$ is —H, methyl or hydroxy.

Non-limiting examples of Formula (VIII) compounds include the following compounds and pharmaceutically acceptable salts thereof:

| No. | Compound Name |
|---|---|
| 460. | 3-bromo-2'-(2-(tert-butyl)pyrimidin-4-yl)-5',6-dimethyl-4-((6-methylpyridin-2-yl)methoxy)-2H-[1,4'-bipyridin]-2-one; |
| 461. | 2'-(2-(tert-butyl)pyrimidin-4-yl)-3-chloro-5',6-dimethyl-4-((6-methylpyridin-2-yl)methoxy)-2H-[1,4'-bipyridin]-2-one; |
| 462. | 2'-(2-(tert-butyl)pyrimidin-4-yl)-3,5',6-trimethyl-4-((6-methylpyridin-2-yl)methoxy)-2H-[1,4'-bipyridin]-2-one; |
| 463. | 3-bromo-2'-(2-(tert-butyl)pyrimidin-4-yl)-5'-chloro-6-methyl-4-((6-methylpyridin-2-yl)methoxy)-2H-[1,4'-bipyridin]-2-one; |
| 464. | 2'-(2-(tert-butyl)pyrimidin-4-yl)-3,5'-dichloro-6-methyl-4-((6-methylpyridin-2-yl)methoxy)-2H-[1,4'-bipyridin]-2-one; |
| 465. | 2'-(2-(tert-butyl)pyrimidin-4-yl)-5'-chloro-3,6-dimethyl-4-((6-methylpyridin-2-yl)methoxy)-2H-[1,4'-bipyridin]-2-one; |
| 466. | 3-bromo-2'-(2-(tert-butyl)pyrimidin-4-yl)-6-methyl-4-((6-methylpyridin-2-yl)methoxy)-2H-[1,4'-bipyridin]-2-one; |
| 467. | 2'-(2-(tert-butyl)pyrimidin-4-yl)-3-chloro-6-methyl-4-((6-methylpyridin-2-yl)methoxy)-2H-[1,4'-bipyridin]-2-one; |
| 468. | 2'-(2-(tert-butyl)pyrimidin-4-yl)-3,6-dimethyl-4-((6-methylpyridin-2-yl)methoxy)-2H-[1,4'-bipyridin]-2-one; |
| 469. | 3-bromo-2'-(2-(tert-butyl)-5-methylpyrimidin-4-yl)-5',6-dimethyl-4-((6-methylpyridin-2-yl)methoxy)-2H-[1,4'-bipyridin]-2-one; |
| 470. | 2'-(2-(tert-butyl)-5-methylpyrimidin-4-yl)-3-chloro-5',6-dimethyl-4-((6-methylpyridin-2-yl)methoxy)-2H-[1,4'-bipyridin]-2-one; |
| 471. | 2'-(2-(tert-butyl)-5-methylpyrimidin-4-yl)-3,5',6-trimethyl-4-((6-methylpyridin-2-yl)methoxy)-2H-[1,4'-bipyridin]-2-one; |
| 472. | 3-bromo-2'-(2-(tert-butyl)-5-methylpyrimidin-4-yl)-5'-chloro-6-methyl-4-((6-methylpyridin-2-yl)methoxy)-2H-[1,4'-bipyridin]-2-one; |
| 473. | 2'-(2-(tert-butyl)-5-methylpyrimidin-4-yl)-3,5'-dichloro-6-methyl-4-((6-methylpyridin-2-yl)methoxy)-2H-[1,4'-bipyridin]-2-one; |
| 474. | 2'-(2-(tert-butyl)-5-methylpyrimidin-4-yl)-5'-chloro-3,6-dimethyl-4-((6-methylpyridin-2-yl)methoxy)-2H-[1,4'-bipyridin]-2-one; |
| 475. | 3-bromo-2'-(2-(tert-butyl)-5-methylpyrimidin-4-yl)-6-methyl-4-((6-methylpyridin-2-yl)methoxy)-2H-[1,4'-bipyridin]-2-one; |
| 476. | 2'-(2-(tert-butyl)-5-methylpyrimidin-4-yl)-3-chloro-6-methyl-4-((6-methylpyridin-2-yl)methoxy)-2H-[1,4'-bipyridin]-2-one; |
| 477. | 2'-(2-(tert-butyl)-5-methylpyrimidin-4-yl)-3,6-dimethyl-4-((6-methylpyridin-2-yl)methoxy)-2H-[1,4'-bipyridin]-2-one; |
| 478. | 3-bromo-2'-(2-isopropylpyrimidin-4-yl)-5',6-dimethyl-4-((6-methylpyridin-2-yl)methoxy)-2H-[1,4'-bipyridin]-2-one; |
| 479. | 3-chloro-2'-(2-isopropylpyrimidin-4-yl)-5',6-dimethyl-4-((6-methylpyridin-2-yl)methoxy)-2H-[1,4'-bipyridin]-2-one; |
| 480. | 2'-(2-isopropylpyrimidin-4-yl)-3,5',6-trimethyl-4-((6-methylpyridin-2-yl)methoxy)-2H-[1,4'-bipyridin]-2-one; |
| 481. | 3-bromo-5'-chloro-2'-(2-isopropylpyrimidin-4-yl)-6-methyl-4-((6-methylpyridin-2-yl)methoxy)-2H-[1,4'-bipyridin]-2-one; |
| 482. | 3,5'-dichloro-2'-(2-isopropylpyrimidin-4-yl)-6-methyl-4-((6-methylpyridin-2-yl)methoxy)-2H-[1,4'-bipyridin]-2-one; |
| 483. | 5'-chloro-2'-(2-isopropylpyrimidin-4-yl)-3,6-dimethyl-4-((6-methylpyridin-2-yl)methoxy)-2H-[1,4'-bipyridin]-2-one; |
| 484. | 3-bromo-2'-(2-isopropylpyrimidin-4-yl)-6-methyl-4-((6-methylpyridin-2-yl)methoxy)-2H-[1,4'-bipyridin]-2-one; |
| 485. | 3-chloro-2'-(2-isopropylpyrimidin-4-yl)-6-methyl-4-((6-methylpyridin-2-yl)methoxy)-2H-[1,4'-bipyridin]-2-one; |
| 486. | 2'-(2-isopropylpyrimidin-4-yl)-3,6-dimethyl-4-((6-methylpyridin-2-yl)methoxy)-2H-[1,4'-bipyridin]-2-one; |
| 487. | 3-bromo-2'-(2-isopropyl-5-methylpyrimidin-4-yl)-5',6-dimethyl-4-((6-methylpyridin-2-yl)methoxy)-2H-[1,4'-bipyridin]-2-one; |

| No. | Compound Name |
|---|---|
| 488. | 3-chloro-2'-(2-isopropyl-5-methylpyrimidin-4-yl)-5',6-dimethyl-4-((6-methylpyridin-2-yl)methoxy)-2H-[1,4'-bipyridin]-2-one; |
| 489. | 2'-(2-isopropyl-5-methylpyrimidin-4-yl)-3,5',6-trimethyl-4-((6-methylpyridin-2-yl)methoxy)-2H-[1,4'-bipyridin]-2-one; |
| 490. | 3-bromo-5'-chloro-2'-(2-isopropyl-5-methylpyrimidin-4-yl)-6-methyl-4-((6-methylpyridin-2-yl)methoxy)-2H-[1,4'-bipyridin]-2-one; |
| 491. | 3,5'-dichloro-2'-(2-isopropyl-5-methylpyrimidin-4-yl)-6-methyl-4-((6-methylpyridin-2-yl)methoxy)-2H-[1,4'-bipyridin]-2-one; |
| 492. | 5'-chloro-2'-(2-isopropyl-5-methylpyrimidin-4-yl)-3,6-dimethyl-4-((6-methylpyridin-2-yl)methoxy)-2H-[1,4'-bipyridin]-2-one; |
| 493. | 3-bromo-2'-(2-isopropyl-5-methylpyrimidin-4-yl)-6-methyl-4-((6-methylpyridin-2-yl)methoxy)-2H-[1,4'-bipyridin]-2-one; |
| 494. | 3-chloro-2'-(2-isopropyl-5-methylpyrimidin-4-yl)-6-methyl-4-((6-methylpyridin-2-yl)methoxy)-2H-[1,4'-bipyridin]-2-one; |
| 495. | 2'-(2-isopropyl-5-methylpyrimidin-4-yl)-3,6-dimethyl-4-((6-methylpyridin-2-yl)methoxy)-2H-[1,4'-bipyridin]-2-one; |
| 496. | 3-bromo-2'-(2-(2-hydroxypropan-2-yl)pyrimidin-4-yl)-5',6-dimethyl-4-((6-methylpyridin-2-yl)methoxy)-2H-[1,4'-bipyridin]-2-one; |
| 497. | 3-chloro-2'-(2-(2-hydroxypropan-2-yl)pyrimidin-4-yl)-5',6-dimethyl-4-((6-methylpyridin-2-yl)methoxy)-2H-[1,4'-bipyridin]-2-one; |
| 498. | 2'-(2-(2-hydroxypropan-2-yl)pyrimidin-4-yl)-3,5',6-trimethyl-4-((6-methylpyridin-2-yl)methoxy)-2H-[1,4'-bipyridin]-2-one; |
| 499. | 3-bromo-5'-chloro-2'-(2-(2-hydroxypropan-2-yl)pyrimidin-4-yl)-6-methyl-4-((6-methylpyridin-2-yl)methoxy)-2H-[1,4'-bipyridin]-2-one; |
| 500. | 3,5'-dichloro-2'-(2-(2-hydroxypropan-2-yl)pyrimidin-4-yl)-6-methyl-4-((6-methylpyridin-2-yl)methoxy)-2H-[1,4'-bipyridin]-2-one; |
| 501. | 5'-chloro-2'-(2-(2-hydroxypropan-2-yl)pyrimidin-4-yl)-3,6-dimethyl-4-((6-methylpyridin-2-yl)methoxy)-2H-[1,4'-bipyridin]-2-one; |
| 502. | 3-bromo-2'-(2-(2-hydroxypropan-2-yl)pyrimidin-4-yl)-6-methyl-4-((6-methylpyridin-2-yl)methoxy)-2H-[1,4'-bipyridin]-2-one; |
| 503. | 3-chloro-2'-(2-(2-hydroxypropan-2-yl)pyrimidin-4-yl)-6-methyl-4-((6-methylpyridin-2-yl)methoxy)-2H-[1,4'-bipyridin]-2-one; |
| 504. | 2'-(2-(2-hydroxypropan-2-yl)pyrimidin-4-yl)-3,6-dimethyl-4-((6-methylpyridin-2-yl)methoxy)-2H-[1,4'-bipyridin]-2-one; |
| 505. | 3-bromo-2'-(2-(2-hydroxypropan-2-yl)-5-methylpyrimidin-4-yl)-5',6-dimethyl-4-((6-methylpyridin-2-yl)methoxy)-2H-[1,4'-bipyridin]-2-one; |
| 506. | 3-chloro-2'-(2-(2-hydroxypropan-2-yl)-5-methylpyrimidin-4-yl)-5',6-dimethyl-4-((6-methylpyridin-2-yl)methoxy)-2H-[1,4'-bipyridin]-2-one; |
| 507. | 2'-(2-(2-hydroxypropan-2-yl)-5-methylpyrimidin-4-yl)-3,5',6-trimethyl-4-((6-methylpyridin-2-yl)methoxy)-2H-[1,4'-bipyridin]-2-one; |
| 508. | 3-bromo-5'-chloro-2'-(2-(2-hydroxypropan-2-yl)-5-methylpyrimidin-4-yl)-6-methyl-4-((6-methylpyridin-2-yl)methoxy)-2H-[1,4'-bipyridin]-2-one; |
| 509. | 3,5'-dichloro-2'-(2-(2-hydroxypropan-2-yl)-5-methylpyrimidin-4-yl)-6-methyl-4-((6-methylpyridin-2-yl)methoxy)-2H-[1,4'-bipyridin]-2-one; |
| 510. | 5'-chloro-2'-(2-(2-hydroxypropan-2-yl)-5-methylpyrimidin-4-yl)-3,6-dimethyl-4-((6-methylpyridin-2-yl)methoxy)-2H-[1,4'-bipyridin]-2-one; |
| 511. | 3-bromo-2'-(2-(2-hydroxypropan-2-yl)-5-methylpyrimidin-4-yl)-6-methyl-4-((6-methylpyridin-2-yl)methoxy)-2H-[1,4'-bipyridin]-2-one; |
| 512. | 3-chloro-2'-(2-(2-hydroxypropan-2-yl)-5-methylpyrimidin-4-yl)-6-methyl-4-((6-methylpyridin-2-yl)methoxy)-2H-[1,4'-bipyridin]-2-one; and |
| 513. | 2'-(2-(2-hydroxypropan-2-yl)-5-methylpyrimidin-4-yl)-3,6-dimethyl-4-((6-methylpyridin-2-yl)methoxy)-2H-[1,4'-bipyridin]-2-one. |
| 514. | 3-bromo-2'-(2-(tert-butyl)pyrimidin-4-yl)-4-((6-methoxypyridin-2-yl)methoxy)-5',6-dimethyl-2H-[1,4'-bipyridin]-2-one; |
| 515. | 2'-(2-(tert-butyl)pyrimidin-4-yl)-3-chloro-4-((6-methoxypyridin-2-yl)methoxy)-5',6-dimethyl-2H-[1,4'-bipyridin]-2-one; |
| 516. | 2'-(2-(tert-butyl)pyrimidin-4-yl)-4-((6-methoxypyridin-2-yl)methoxy)-3,5',6-trimethyl-2H-[1,4'-bipyridin]-2-one; |
| 517. | 3-bromo-2'-(2-(tert-butyl)pyrimidin-4-yl)-5'-chloro-4-((6-methoxypyridin-2-yl)methoxy)-6-methyl-2H-[1,4'-bipyridin]-2-one; |
| 518. | 2'-(2-(tert-butyl)pyrimidin-4-yl)-3,5'-dichloro-4-((6-methoxypyridin-2-yl)methoxy)-6-methyl-2H-[1,4'-bipyridin]-2-one; |
| 519. | 2'-(2-(tert-butyl)pyrimidin-4-yl)-5'-chloro-4-((6-methoxypyridin-2-yl)methoxy)-3,6-dimethyl-2H-[1,4'-bipyridin]-2-one; |
| 520. | 3-bromo-2'-(2-(tert-butyl)pyrimidin-4-yl)-4-((6-methoxypyridin-2-yl)methoxy)-6-methyl-2H-[1,4'-bipyridin]-2-one; |
| 521. | 2'-(2-(tert-butyl)pyrimidin-4-yl)-3-chloro-4-((6-methoxypyridin-2-yl)methoxy)-6-methyl-2H-[1,4'-bipyridin]-2-one; |
| 522. | 2'-(2-(tert-butyl)pyrimidin-4-yl)-4-((6-methoxypyridin-2-yl)methoxy)-3,6-dimethyl-2H-[1,4'-bipyridin]-2-one; |
| 523. | 3-bromo-2'-(2-(tert-butyl)-5-methylpyrimidin-4-yl)-4-((6-methoxypyridin-2-yl)methoxy)-5',6-dimethyl-2H-[1,4'-bipyridin]-2-one; |
| 524. | 2'-(2-(tert-butyl)-5-methylpyrimidin-4-yl)-3-chloro-4-((6-methoxypyridin-2-yl)methoxy)-5',6-dimethyl-2H-[1,4'-bipyridin]-2-one; |
| 525. | 2'-(2-(tert-butyl)-5-methylpyrimidin-4-yl)-4-((6-methoxypyridin-2-yl)methoxy)-3,5',6-trimethyl-2H-[1,4'-bipyridin]-2-one; |
| 526. | 3-bromo-2'-(2-(tert-butyl)-5-methylpyrimidin-4-yl)-5'-chloro-4-((6-methoxypyridin-2-yl)methoxy)-6- |

| No. | Compound Name |
|---|---|
| | methyl-2H-[1,4'-bipyridin]-2-one; |
| 527. | 2'-(2-(tert-butyl)-5-methylpyrimidin-4-yl)-3,5'-dichloro-4-((6-methoxypyridin-2-yl)methoxy)-6-methyl-2H-[1,4'-bipyridin]-2-one; |
| 528. | 2'-(2-(tert-butyl)-5-methylpyrimidin-4-yl)-5'-chloro-4-((6-methoxypyridin-2-yl)methoxy)-3,6-dimethyl-2H-[1,4'-bipyridin]-2-one; |
| 529. | 3-bromo-2'-(2-(tert-butyl)-5-methylpyrimidin-4-yl)-4-((6-methoxypyridin-2-yl)methoxy)-6-methyl-2H-[1,4'-bipyridin]-2-one; |
| 530. | 2'-(2-(tert-butyl)-5-methylpyrimidin-4-yl)-3-chloro-4-((6-methoxypyridin-2-yl)methoxy)-6-methyl-2H-[1,4'-bipyridin]-2-one; |
| 531. | 2'-(2-(tert-butyl)-5-methylpyrimidin-4-yl)-4-((6-methoxypyridin-2-yl)methoxy)-3,6-dimethyl-2H-[1,4'-bipyridin]-2-one; |
| 532. | 3-bromo-2'-(2-isopropylpyrimidin-4-yl)-4-((6-methoxypyridin-2-yl)methoxy)-5',6-dimethyl-2H-[1,4'-bipyridin]-2-one; |
| 533. | 3-chloro-2'-(2-isopropylpyrimidin-4-yl)-4-((6-methoxypyridin-2-yl)methoxy)-5',6-dimethyl-2H-[1,4'-bipyridin]-2-one; |
| 534. | 2'-(2-isopropylpyrimidin-4-yl)-4-((6-methoxypyridin-2-yl)methoxy)-3,5',6-trimethyl-2H-[1,4'-bipyridin]-2-one; |
| 535. | 3-bromo-5'-chloro-2'-(2-isopropylpyrimidin-4-yl)-4-((6-methoxypyridin-2-yl)methoxy)-6-methyl-2H-[1,4'-bipyridin]-2-one; |
| 536. | 3,5'-dichloro-2'-(2-isopropylpyrimidin-4-yl)-4-((6-methoxypyridin-2-yl)methoxy)-6-methyl-2H-[1,4'-bipyridin]-2-one; |
| 537. | 5'-chloro-2'-(2-isopropylpyrimidin-4-yl)-4-((6-methoxypyridin-2-yl)methoxy)-3,6-dimethyl-2H-[1,4'-bipyridin]-2-one; |
| 538. | 3-bromo-2'-(2-isopropylpyrimidin-4-yl)-4-((6-methoxypyridin-2-yl)methoxy)-6-methyl-2H-[1,4'-bipyridin]-2-one; |
| 539. | 3-chloro-2'-(2-isopropylpyrimidin-4-yl)-4-((6-methoxypyridin-2-yl)methoxy)-6-methyl-2H-[1,4'-bipyridin]-2-one; |
| 540. | 2'-(2-isopropylpyrimidin-4-yl)-4-((6-methoxypyridin-2-yl)methoxy)-3,6-dimethyl-2H-[1,4'-bipyridin]-2-one; |
| 541. | 3-bromo-2'-(2-isopropyl-5-methylpyrimidin-4-yl)-4-((6-methoxypyridin-2-yl)methoxy)-5',6-dimethyl-2H-[1,4'-bipyridin]-2-one; |
| 542. | 3-chloro-2'-(2-isopropyl-5-methylpyrimidin-4-yl)-4-((6-methoxypyridin-2-yl)methoxy)-5',6-dimethyl-2H-[1,4'-bipyridin]-2-one; |
| 543. | 2'-(2-isopropyl-5-methylpyrimidin-4-yl)-4-((6-methoxypyridin-2-yl)methoxy)-3,5',6-trimethyl-2H-[1,4'-bipyridin]-2-one; |
| 544. | 3-bromo-5'-chloro-2'-(2-isopropyl-5-methylpyrimidin-4-yl)-4-((6-methoxypyridin-2-yl)methoxy)-6-methyl-2H-[1,4'-bipyridin]-2-one; |
| 545. | 3,5'-dichloro-2'-(2-isopropyl-5-methylpyrimidin-4-yl)-4-((6-methoxypyridin-2-yl)methoxy)-6-methyl-2H-[1,4'-bipyridin]-2-one; |
| 546. | 5'-chloro-2'-(2-isopropyl-5-methylpyrimidin-4-yl)-4-((6-methoxypyridin-2-yl)methoxy)-3,6-dimethyl-2H-[1,4'-bipyridin]-2-one; |
| 547. | 3-bromo-2'-(2-isopropyl-5-methylpyrimidin-4-yl)-4-((6-methoxypyridin-2-yl)methoxy)-6-methyl-2H-[1,4'-bipyridin]-2-one; |
| 548. | 3-chloro-2'-(2-isopropyl-5-methylpyrimidin-4-yl)-4-((6-methoxypyridin-2-yl)methoxy)-6-methyl-2H-[1,4'-bipyridin]-2-one; |
| 549. | 2'-(2-isopropyl-5-methylpyrimidin-4-yl)-4-((6-methoxypyridin-2-yl)methoxy)-3,6-dimethyl-2H-[1,4'-bipyridin]-2-one; |
| 550. | 3-bromo-2'-(2-(2-hydroxypropan-2-yl)pyrimidin-4-yl)-4-((6-methoxypyridin-2-yl)methoxy)-5',6-dimethyl-2H-[1,4'-bipyridin]-2-one; |
| 551. | 3-chloro-2'-(2-(2-hydroxypropan-2-yl)pyrimidin-4-yl)-4-((6-methoxypyridin-2-yl)methoxy)-5',6-dimethyl-2H-[1,4'-bipyridin]-2-one; |
| 552. | 2'-(2-(2-hydroxypropan-2-yl)pyrimidin-4-yl)-4-((6-methoxypyridin-2-yl)methoxy)-3,5',6-trimethyl-2H-[1,4'-bipyridin]-2-one; |
| 553. | 3-bromo-5'-chloro-2'-(2-(2-hydroxypropan-2-yl)pyrimidin-4-yl)-4-((6-methoxypyridin-2-yl)methoxy)-6-methyl-2H-[1,4'-bipyridin]-2-one; |
| 554. | 3,5'-dichloro-2'-(2-(2-hydroxypropan-2-yl)pyrimidin-4-yl)-4-((6-methoxypyridin-2-yl)methoxy)-6-methyl-2H-[1,4'-bipyridin]-2-one; |
| 555. | 5'-chloro-2'-(2-(2-hydroxypropan-2-yl)pyrimidin-4-yl)-4-((6-methoxypyridin-2-yl)methoxy)-3,6-dimethyl-2H-[1,4'-bipyridin]-2-one; |
| 556. | 3-bromo-2'-(2-(2-hydroxypropan-2-yl)pyrimidin-4-yl)-4-((6-methoxypyridin-2-yl)methoxy)-6-methyl-2H-[1,4'-bipyridin]-2-one; |
| 557. | 3-chloro-2'-(2-(2-hydroxypropan-2-yl)pyrimidin-4-yl)-4-((6-methoxypyridin-2-yl)methoxy)-6-methyl-2H-[1,4'-bipyridin]-2-one; |
| 558. | 2'-(2-(2-hydroxypropan-2-yl)pyrimidin-4-yl)-4-((6-methoxypyridin-2-yl)methoxy)-3,6-dimethyl-2H-[1,4'-bipyridin]-2-one; |
| 559. | 3-bromo-2'-(2-(2-hydroxypropan-2-yl)-5-methylpyrimidin-4-yl)-4-((6-methoxypyridin-2-yl)methoxy)-5',6-dimethyl-2H-[1,4'-bipyridin]-2-one; |
| 560. | 3-chloro-2'-(2-(2-hydroxypropan-2-yl)-5-methylpyrimidin-4-yl)-4-((6-methoxypyridin-2-yl)methoxy)-5',6-dimethyl-2H-[1,4'-bipyridin]-2-one; |
| 561. | 2'-(2-(2-hydroxypropan-2-yl)-5-methylpyrimidin-4-yl)-4-((6-methoxypyridin-2-yl)methoxy)-3,5',6-trimethyl-2H-[1,4'-bipyridin]-2-one; |
| 562. | 3-bromo-5'-chloro-2'-(2-(2-hydroxypropan-2-yl)-5-methylpyrimidin-4-yl)-4-((6-methoxypyridin-2-yl)methoxy)-6-methyl-2H-[1,4'-bipyridin]-2-one; |
| 563. | 3,5'-dichloro-2'-(2-(2-hydroxypropan-2-yl)-5-methylpyrimidin-4-yl)-4-((6-methoxypyridin-2-yl)methoxy)-6-methyl-2H-[1,4'-bipyridin]-2-one; |
| 564. | 5'-chloro-2'-(2-(2-hydroxypropan-2-yl)-5-methylpyrimidin-4-yl)-4-((6-methoxypyridin-2-yl)methoxy)-3,6-dimethyl-2H-[1,4'-bipyridin]-2-one; |

| No. | Compound Name |
|---|---|
| 565. | 3-bromo-2'-(2-(2-hydroxypropan-2-yl)-5-methylpyrimidin-4-yl)-4-((6-methoxypyridin-2-yl)methoxy)-6-methyl-2H-[1,4'-bipyridin]-2-one; |
| 566. | 3-chloro-2'-(2-(2-hydroxypropan-2-yl)-5-methylpyrimidin-4-yl)-4-((6-methoxypyridin-2-yl)methoxy)-6-methyl-2H-[1,4'-bipyridin]-2-one; and |
| 567. | 2'-(2-(2-hydroxypropan-2-yl)-5-methylpyrimidin-4-yl)-4-((6-methoxypyridin-2-yl)methoxy)-3,6-dimethyl-2H-[1,4'-bipyridin]-2-one. |

C. Methods of Treatment

The present disclosure further provides methods for treating a condition in a subject having or susceptible to having such a condition, by administering to the subject a therapeutically-effective amount of one or more compounds as described above. In one embodiment, the treatment is preventative treatment. In another embodiment, the treatment is palliative treatment. In another embodiment, the treatment is restorative treatment.

1. Conditions

The conditions that can be treated in accordance with the present invention include, but are not limited to, autoimmune disorders, chronic inflammatory disorders, acute inflammatory disorders, auto-inflammatory disorders, pain, atherosclerosis, diabetes, fibrotic diseases, metabolic disorders, cancer, neoplasia, leukemia, lymphoma and the like.

In some embodiments the methods described herein are used to treat patients with disorders arising from dysregulated cytokine, enzymes and/or inflammatory mediator production, stability, secretion, posttranslational processing. Examples of cytokines that may be dysregulated include interleukins 1, 2, 6, 8, 10, 12, 17, 22 and 23 along with tumor necrosis factor alpha and interferons alpha, beta and gamma. Examples of inflammatory mediators that may be dysregulated include nitric oxide, prostaglandins and leukotrienes. Examples of enzymes include cyclo-oxygenase, nitric oxide synthase and matrixmetalloprotease.

In some embodiments the methods described herein are used to treat patients with dysregulated p38 activity, activation, biosynthesis or pathway function.

In some embodiments, the methods described herein are used to treat a patient in need thereof suffering from an autoimmune disorder, chronic and/or acute inflammatory disorder and/or auto-inflammatory disorder. Examples of disorders include, but are not limited to colitis, multiple sclerosis, arthritis, rheumatoid arthritis, osteoarthritis, juvenile arthritis, psoriatic arthritis, cryopyrin associated periodic syndromes, Muckle-Wells Syndrome, Familial Cold Auto-inflammatory Syndrome, neonatal-onset multisystem inflammatory disease, TNF receptor associated periodic syndrome, acute pancreatitis, chronic pancreatitis, atherosclerosis, inflammatory bowel disease, Crohn's disease, ulcerative colitis, Diabetes mellitus type 1, Diabetes mellitus type 2, diabetic retinopathy, Still's disease, multiple sclerosis, vasculitis, sarcoidosis, pulmonary inflammation, acute respiratory distress syndrome, wet and dry age-related macular degeneration, autoimmune hemolytic syndromes, autoimmune hepatitis, autoimmune neuropathy, autoimmune ovarian failure, autoimmune orchitis, autoimmune thrombocytopenia, reactive arthritis, ankylosing spondylitis, silicone implant associated autoimmune disease, Sjogren's syndrome, Familial Mediterranean Fever, systemic lupus erythematosus, vasculitis syndromes (such as, for example, giant cell arteritis, Behcet's disease & Wegener's granulomatosis), Vitiligo, secondary hematologic manifestation of autoimmune diseases (such as, for example, anemias), drug-induced autoimmunity, Hashimoto's thyroiditis, hypophysitis, idiopathic thrombocytic pupura, metal-induced autoimmunity, myasthenia gravis, pemphigus, autoimmune deafness (including, for example, Meniere's disease), Goodpasture's syndrome, Graves' disease, HW-related autoimmune syndromes and Gullain-Barre disease; Examples of inflammatory conditions include, but are not limited to sepsis, septic shock, endotoxic shock, exotoxin-induced toxic shock, gram negative sepsis, toxic shock syndrome, glomerulonephritis, peritonitis, interstitial cystitis, psoriasis, atopic dermatitis, hyperoxia-induced inflammations, asthma, chronic obstructive pulmonary disease (COPD), vasculitis, graft vs. host reaction (i.e., graft vs. host disease), allograft rejections (e.g., acute allograft rejection, and chronic allograft rejection), early transplantation rejection (e.g., acute allograft rejection), reperfusion injury, acute pain, chronic pain, neuropathic pain, Fibromyalgia, pancreatitis, chronic infections, meningitis, encephalitis, myocarditis, gingivitis, post surgical trauma, tissue injury, traumatic brain injury, hepatitis, enterocolitis, sinusitis, uveitis, ocular inflammation, optic neuritis, gastric ulcers, esophagitis, peritonitis, periodontitis, dermatomyositis, gastritis, myositis, polymyalgia, pneumonia and bronchitis. Fibrotic diseases; Metabolic disorders, including but not limited Obesity, steroid-resistance, glucose intolerance, metabolic syndrome. In some embodiments, the methods described herein can be used to treat a patient in need thereof and suffering from neoplasia. Examples of these conditions include but not limited to angiogenesis, multiple myeloma, leukemia, B cell lymphoma, T cell lymphoma, mast cell tumors, lymphoma, Hodgkin's disease, cancer of the bone, mouth/pharynx, oesophagus, larynx, stomach, intestine, colon, rectum, lung, liver, pancreas, nerve, brain, head and neck, throat, ovary, uterus, prostate, testis, bladder, kidney, breast non-small cell lung carcinoma, melanoma, skin cancer, teratoma, rhabdomyosarcoma, glioma, metastatic and bone disorders. In some embodiments, the disease associated with dysregulated p38 include Cardiovascular and Cerebrovascular diseases, including but not limited to Atherosclerosis, restenosis of an atherosclerotic coronary artery, Acute coronary syndrome, myocardial infarction, cardiac-allograft vasculopathy and stroke; central nervous system disorders with an inflammatory or apoptotic component, Alzheimer's disease, Parkinson's disease, Huntington's disease, amyotrophic lateral sclerosis, spinal cord injury, neuronal ischemia and peripheral neuropathy. The term patient refers to both humans and nonhuman animals with the abovementioned conditions. Nonhuman animals could be companion animals such as, but not limited to canine and feline species.

2. Subjects

Suitable subjects to be treated according to the present invention include mammalian subjects. Mammals according to the present invention include, but are not limited to, human, canine, feline, bovine, caprine, equine, ovine, porcine, rodents, lagomorphs, primates, and the like, and encompass mammals in utero. Subjects may be of either gender and at any stage of development.

3. Administration and Dosing

The compounds of the present invention are generally administered in a therapeutically effective amount.

The compounds of the present invention can be administered by any suitable route in the form of a pharmaceutical composition adapted to such a route, and in a dose effective for the treatment intended. An effective dosage is typically in the range of about 0.001 to about 100 mg per kg body weight per day, preferably about 0.01 to about 30 mg/kg/day, in single or divided doses. Depending on age, species and condition being treated, dosage levels below the lower limit of this range may be suitable. In other cases, still larger doses may be used without harmful side effects. Larger doses may also be divided into several smaller doses, for administration throughout the day.

D. Phatmaceutical Compositions

For the treatment of the conditions referred to above, the compounds of described herein can be administered as follows:

Oral Administration

The compounds of the present invention may be administered orally, including by swallowing, so that the compound enters the gastrointestinal tract, or absorbed into the blood stream directly from the mouth (e.g., buccal or sublingual administration).

Suitable compositions for oral administration include solid formulations such as tablets, lozenges and capsules, which can contain liquids, gels, or powders.

Compositions for oral administration may be formulated as immediate or modified release, including delayed or sustained release, optionally with enteric coating.

Liquid formulations can include solutions, syrups and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

In a tablet dosage form the amount of drug present may be from about 0.05% to about 95% by weight, more typically from about 2% to about 50% by weight of the dosage form. In addition, tablets may contain a disintegrant, comprising from about 0.5% to about 35% by weight, more typically from about 2% to about 25% of the dosage form. Examples of disintegrants include methyl cellulose, sodium or calcium carboxymethyl cellulose, croscarmellose sodium, polyvinylpyrrolidone, hydroxypropyl cellulose, starch and the like.

Suitable lubricants, for use in a tablet, may be present in amounts from about 0.1% to about 5% by weight, and include calcium, zinc or magnesium stearate, sodium stearyl fumarate and the like.

Suitable binders, for use in a tablet, include gelatin, polyethylene glycol, sugars, gums, starch, hydroxypropyl cellulose and the like. Suitable diluents, for use in a tablet, include mannitol, xylitol, lactose, dextrose, sucrose, sorbitol and starch.

Suitable surface active agents and glidants, for use in a tablet, may be present in amounts from about 0.1% to about 3% by weight, and include polysorbate 80, sodium dodecyl sulfate, talc and silicon dioxide.

Parenteral Administration

Compounds of the present invention may be administered directly into the blood stream, muscle, or internal organs.

Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods.

Compositions for parenteral administration may be formulated as immediate or modified release, including delayed or sustained release.

Most parenteral formulations are aqueous solutions containing excipients, including salts, buffering agents and carbohydrates.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions.

Topical Administration

Compounds of the present invention may be administered topically to the skin or transdermally. Formulations for this topical administration can include lotions, solutions, creams, gels, hydrogels, ointments, foams, implants, patches and the like. Pharmaceutically acceptable carriers for topical administration formulations can include water, alcohol, mineral oil, glycerin, polyethylene glycol and the like. Topical administration can also be performed by electroporation, iontophoresis, phonophoresis and the like.

Compositions for topical administration may be formulated as immediate or modified release, including delayed or sustained release.

E. Combinations and Combination Therapy

The compounds of the present invention can be used, alone or in combination with other pharmaceutically active compounds, to treat conditions such as those previously described above. The compound(s) of the present invention and other pharmaceutically active compound(s) can be administered simultaneously (either in the same dosage form or in separate dosage forms) or sequentially. Accordingly, in one embodiment, the present invention comprises methods for treating a condition by administering to the subject a therapeutically-effective amount of one or more compounds of the present invention and one or more additional pharmaceutically active compounds.

In another embodiment, there is provided a pharmaceutical composition comprising one or more compounds of the present invention, one or more additional pharmaceutically active compounds, and a pharmaceutically acceptable carrier.

In another embodiment, the one or more additional pharmaceutically active compounds is selected from the group consisting of anti-inflammatory drugs, anti-atherosclerotic drugs, immunosuppressive drugs, immunomodulatory drugs, cytostatic drugs, anti-proliferative agents, angiogenesis inhibitors, kinase inhibitors, cytokine blockers and inhibitors of cell adhesion molecules.

p38 inhibitor compositions described herein are also optionally used in combination with other therapeutic reagents that are selected for their therapeutic value for the condition to be treated In general, the compositions described herein and, in embodiments where combinational therapy is employed, other agents do not have to be administered in the same pharmaceutical composition, and, because of different physical and chemical characteristics, are optionally administered by different routes. The initial administration is generally made according to established protocols, and then, based upon the observed effects, the dosage, modes of administration and times of administration subsequently modified.

In certain instances, it is appropriate to administer a p38 inhibitor composition as described herein in combination with another therapeutic agent. By way of example only, if one of the side effects experienced by a patient upon receiving a p38 inhibitor composition as described herein is rash, then it is appropriate to administer an anti-histamine agent in combination with the initial therapeutic agent. Or, by way of example only, the therapeutic effectiveness of a p38 inhibitor is enhanced by administration of another therapeutic agent (which also includes a therapeutic regimen) that also has therapeutic benefit. In any case, regardless of the disease, disorder or condition being treated, the overall benefit experienced by the patient is either simply additive of the two therapeutic agents or the patient experiences a synergistic benefit.

Therapeutically effective dosages vary when the drugs are used in treatment combinations. Methods for experimentally determining therapeutically effective dosages of drugs and other agents for use in combination treatment regimens are documented methodologies. Combination treatment further includes periodic treatments that start and stop at various times to assist with the clinical management of the patient. In any case, the multiple therapeutic agents (one of which is a p38 inhibitor as described herein) are administered in any order, or even simultaneously. If simultaneously, the multiple therapeutic agents are optionally provided in a single, unified form, or in multiple forms (by way of example only, either as a single pill or as two separate pills).

In some embodiments, one of the therapeutic agents is given in multiple doses, or both are given as multiple doses. If not simultaneous, the timing between the multiple doses optionally varies from more than zero weeks to less than twelve weeks.

In addition, the combination methods, compositions and formulations are not to be limited to the use of only two agents, the use of multiple therapeutic combinations are also envisioned. It is understood that the dosage regimen to treat, prevent, or ameliorate the condition(s) for which relief is sought, is optionally modified in accordance with a variety of factors. These factors include the disorder from which the subject suffers, as well as the age, weight, sex, diet, and medical condition of the subject. Thus, the dosage regimen actually employed varies widely, in some embodiments, and therefore deviates from the dosage regimens set forth herein.

The pharmaceutical agents which make up the combination therapy disclosed herein are optionally a combined dosage form or in separate dosage forms intended for substantially simultaneous administration. The pharmaceutical agents that make up the combination therapy are optionally also administered sequentially, with either agent being administered by a regimen calling for two-step administration. The two-step administration regimen optionally calls for sequential administration of the active agents or spaced-apart administration of the separate active agents. The time period between the multiple administration steps ranges from, a few minutes to several hours, depending upon the properties of each pharmaceutical agent, such as potency, solubility, bioavailability, plasma half-life and kinetic profile of the pharmaceutical agent. Circadian variation of the target molecule concentration is optionally used to determine the optimal dose interval.

In another embodiment, a p38 inhibitor is optionally used in combination with procedures that provide additional or synergistic benefit to the patient. A p38 inhibitor and the additional therapy(ies) are optionally administered before, during or after the occurrence of a disease or condition, and the timing of administering the composition containing a p38 inhibitor varies in some embodiments. Thus, for example, a p38 inhibitor is used as a prophylactic and is administered continuously to subjects with a propensity to develop conditions or diseases in order to prevent the occurrence of the disease or condition. A p38 inhibitor and compositions are optionally administered to a subject during or as soon as possible after the onset of the symptoms. While embodiments of the present invention have been shown and described herein, it will be obvious to those skilled in the art that such embodiments are provided by way of example only. Numerous variations, changes, and substitutions will now occur to those skilled in the art without departing from the invention. It should be understood that in some embodiments of the invention various alternatives to the embodiments described herein are employed in practicing the invention.

A p38 inhibitor can be used in combination with drugs from the following classes: NSAIDs, immunosuppressive drugs, immunomodulatory drugs, cytostatic drugs, anti-proliferative agents, angiogenesis inhibitors, biological agents, steroids, vitamin D3 analogs, retinoids, other kinase inhibitors, cytokine blockers, corticosteroids and inhibitors of cell adhesion molecules. Where a subject is suffering from or at risk of suffering from atherosclerosis or a condition that is associated with atherosclerosis, a p38 inhibitor composition described herein is optionally used together with one or more agents or methods for treating atherosclerosis or a condition that is associated with atherosclerosis in any combination. Examples of therapeutic agents/treatments for treating atherosclerosis or a condition that is associated with atherosclerosis include, but are not limited to any of the following: torcetrapib, aspirin, niacin, HMG CoA reductase inhibitors (e.g., atorvastatin, fluvastatin, lovastatin, pravastatin, rosuvastatin and simvastatin), colesevelam, cholestyramine, colestipol, gemfibrozil, probucol and clofibrate.

Where a subject is suffering from or at risk of suffering from an inflammatory condition, a p38 inhibitor composition described herein is optionally used together with one or more agents or methods for treating an inflammatory condition in any combination. Examples of therapeutic agents/treatments for treating an autoimmune and/or inflammatory condition include, but are not limited to any of the following: corticosteroids, nonsteroidal antiinflammatory drugs (NSAID) (e.g. ibuprofen, naproxen, acetaminophen, aspirin, Fenoprofen (Nalfon), Flurbiprofen (Ansaid), Ketoprofen, Oxaprozin (Daypro), Diclofenac sodium (Voltaren), Diclofenac potassium (Cataflam), Etodolac (Lodine), Indomethacin (Indocin), Ketorolac (Toradol), Sulindac (Clinoril), Tolmetin (Tolectin), Meclofenamate (Meclomen), Mefenamic acid (Ponstel), Nabumetone (Relafen), Piroxicam (Feldene), cox-2 inhibitors (e.g., celecoxib (Celebrex))), immunosuppressants (e.g., methotrexate (Rheumatrex), leflunomide (Arava), azathioprine (Imuran), cyclosporine (Neoral, Sandimmune), tacrolimus and cyclophosphamide (Cytoxan), CD20 blockers (Rituximab), Tumor Necrosis Factor (TNF) blockers (e.g., etanercept (Enbrel), infliximab (Remicade) and adalimumab (Humira)), Abatacept (CTLA4-Ig) and interleukin-1 receptor antagonists (e.g. Anakinra (Kineret), interleukin 6 inhibitors (e.g., Actemra), interleukin 17 inhibitors (e.g., AIN457), Janus kinase inhibitors (e.g., Tasocitinib), syk inhibitors (e.g. R788), chloroquine and its derivatives.

For use in cancer and neoplastic diseases a p38 inhibitor is optimally used together with one or more of the following classes of drugs: wherein the anti-cancer agent is an EGFR kinase inhibitor, MEK inhibitor, VEGFR inhibitor, anti-VEGFR2 antibody, KDR antibody, AKT inhibitor, PDK-1 inhibitor, PI3K inhibitor, c-kit/Kdr tyrosine kinase inhibitor, Bcr-Abl tyrosine kinase inhibitor, VEGFR2 inhibitor, PDGFR-beta inhibitor, KIT inhibitor, Flt3 tyrosine kinase inhibitor, PDGF receptor family inhibitor, Flt3 tyrosine kinase inhibitor, RET tyrosine kinase receptor family inhibitor, VEGF-3 receptor antagonist, Raf protein kinase family inhibitor, angiogenesis inhibitor, Erb2 inhibitor, mTOR inhibitor, IGF-1R antibody, NFkB inhibitor, proteosome inhibitor, chemotherapy agent, or glucose reduction agent.

F. Kits

The present invention further comprises kits that are suitable for use in performing the methods of treatment or prevention described above. In one embodiment, the kit contains a first dosage form comprising one or more of the compounds of the present invention and a container for the dosage, in quantities sufficient to carry out the methods of the present invention.

G. Intermediates

In another embodiment, the invention relates to the novel intermediates useful for preparing the compounds of the present invention.

H. General Synthetic Schemes

The compounds of the present invention can be prepared using the methods illustrated in the general synthetic schemes and experimental procedures detailed below. These general synthetic schemes and experimental procedures are presented for purposes of illustration and are not intended to be limiting. The starting materials used to prepare the compounds of the present invention are commercially available or can be prepared using routine methods known in the art.

Representative procedures for the preparation of compounds of invention are outlined below in Schemes 1-3. The substituted pyridine starting materials can be purchased or prepared using methods known in the art. The synthesis of pyridinone intermediate 1c, can be accomplished by the reaction of 4-hydroxypyrone 1a with the amino-heteroaryl ester 1b. Halogenation of 1c using N-bromo or N-chlorosuccinimide in isopropanol or dichloroethane in the presence of acetic acid or dichloroacetic acid can furnish halogenated pyridinone 1d. Benzylation of 1d with p-methoxybenzyl chloride can provide the p-methoxybenzyl ether represented by 1f.

Scheme 1

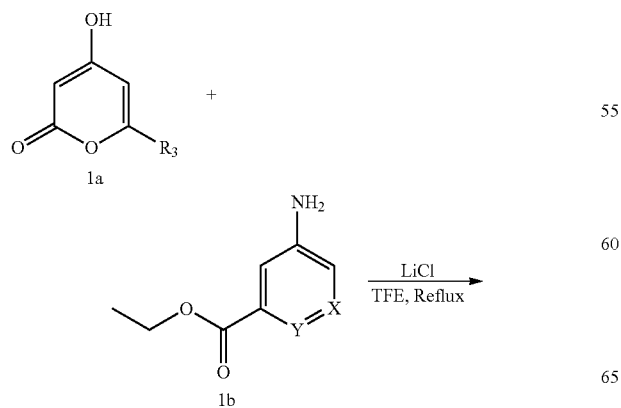

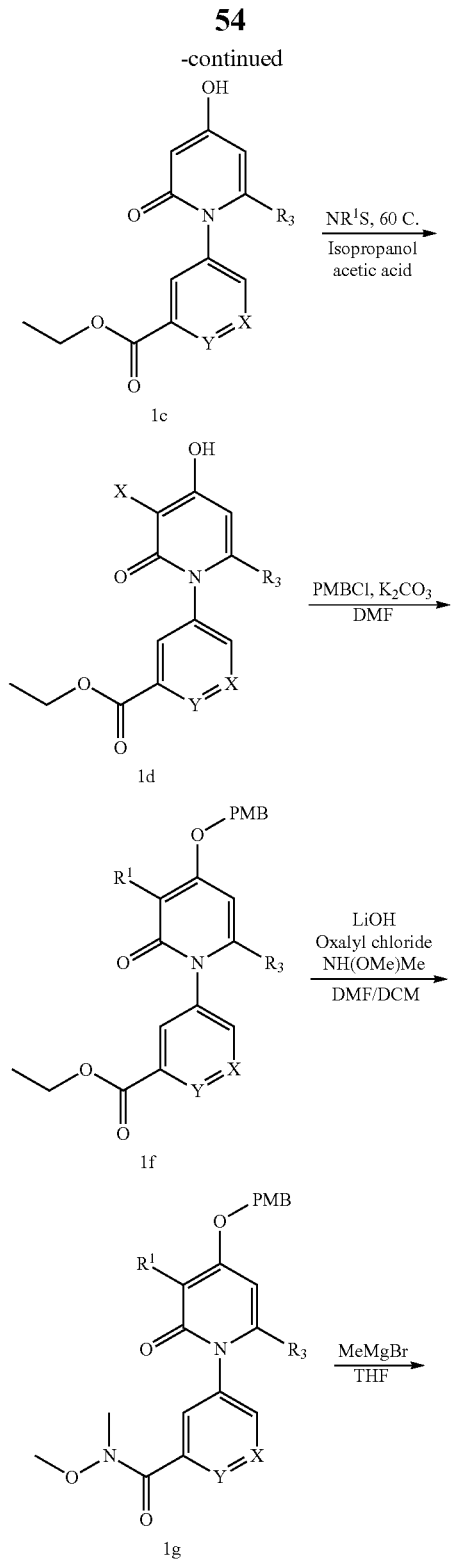

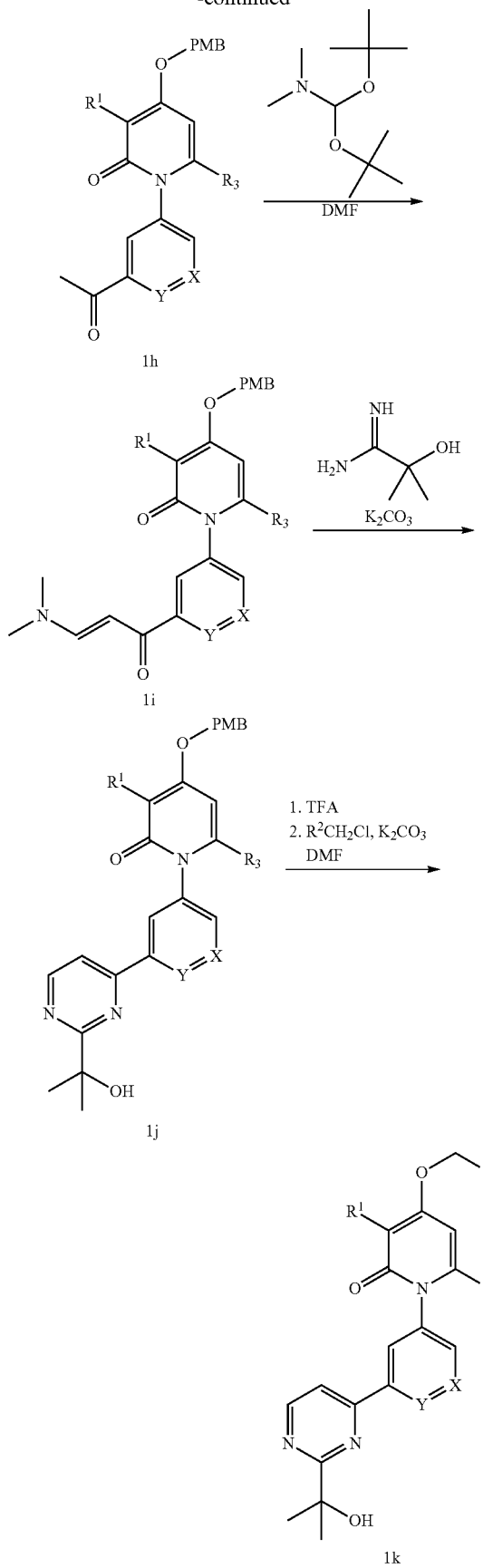

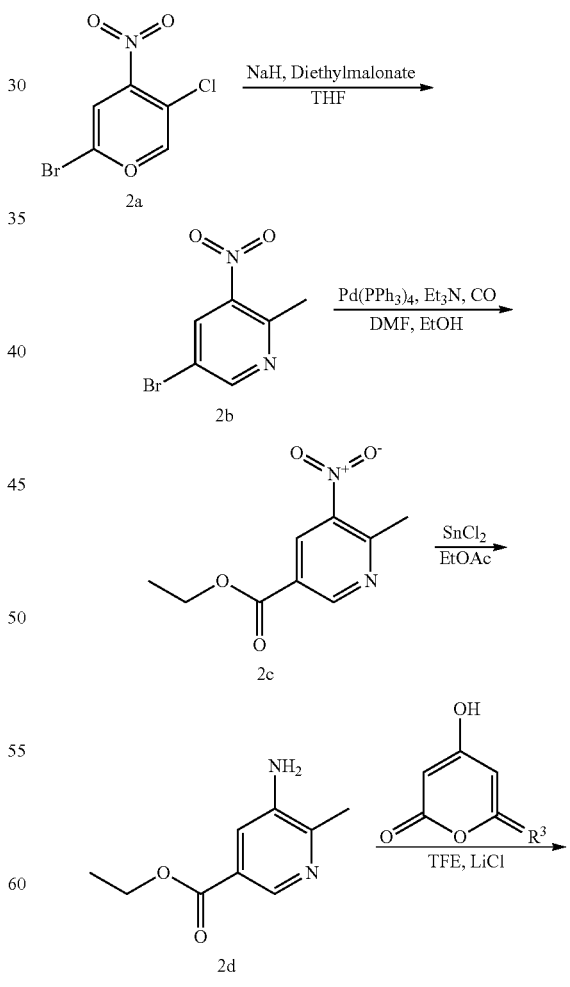

$R^1$ = Cl or Br

Conventional hydrolysis of the ethyl ester 1f to the corresponding acid followed by acid chloride formation and reaction with N-methoxy-N-methylamine can provide the amide intermediate 1g. Methyl ketone 1h formation, using methylmagnesium bromide followed by condensation with di-t-butoxy-N,N-dimethyl would furnish the eneamine product represented by 1i. Condensation of the eneamine 1i with the amidine reagent in the presence of a base can provide the pyrimidine product 1j. Removal of the p-methoxybenzyl group under standard reaction conditions followed by alkylation with the appropriate heterocyclicmethyl halide can furnish the desired final products represented by the formula 1k.

Compound 1k where $R^1$ is bromo or iodo, can also be used to obtain compounds with $R^1$ having methyl or ethyl groups using bis-(triphenylphosphine)palladium(II) chloride and triethylamine and hexamethylditin or trimethylsilylacetylene.

Scheme 2

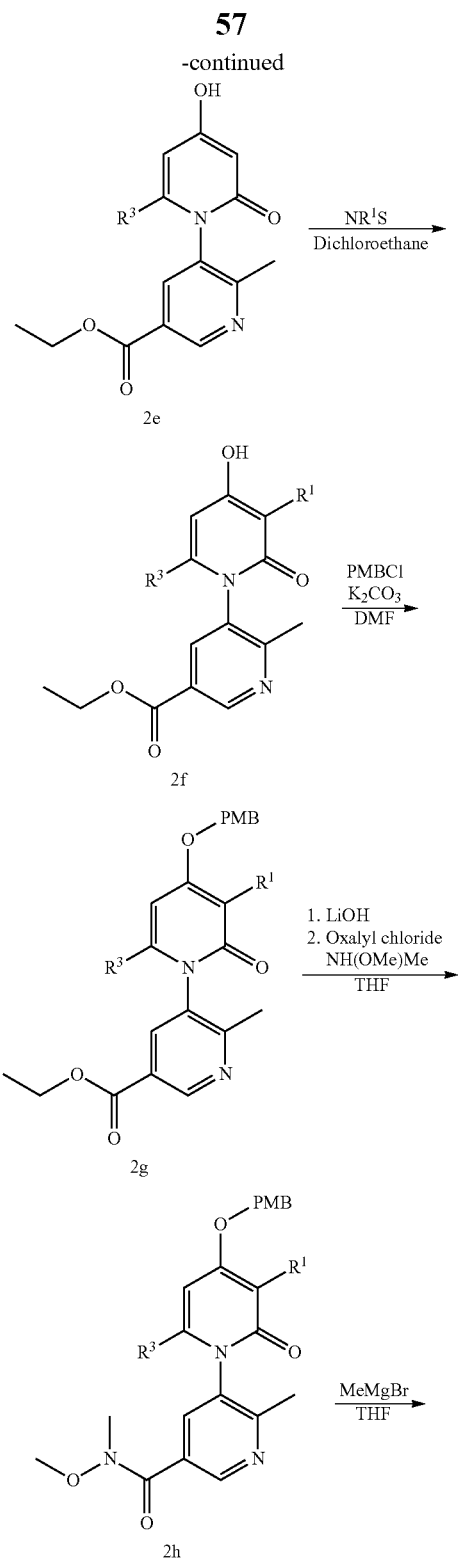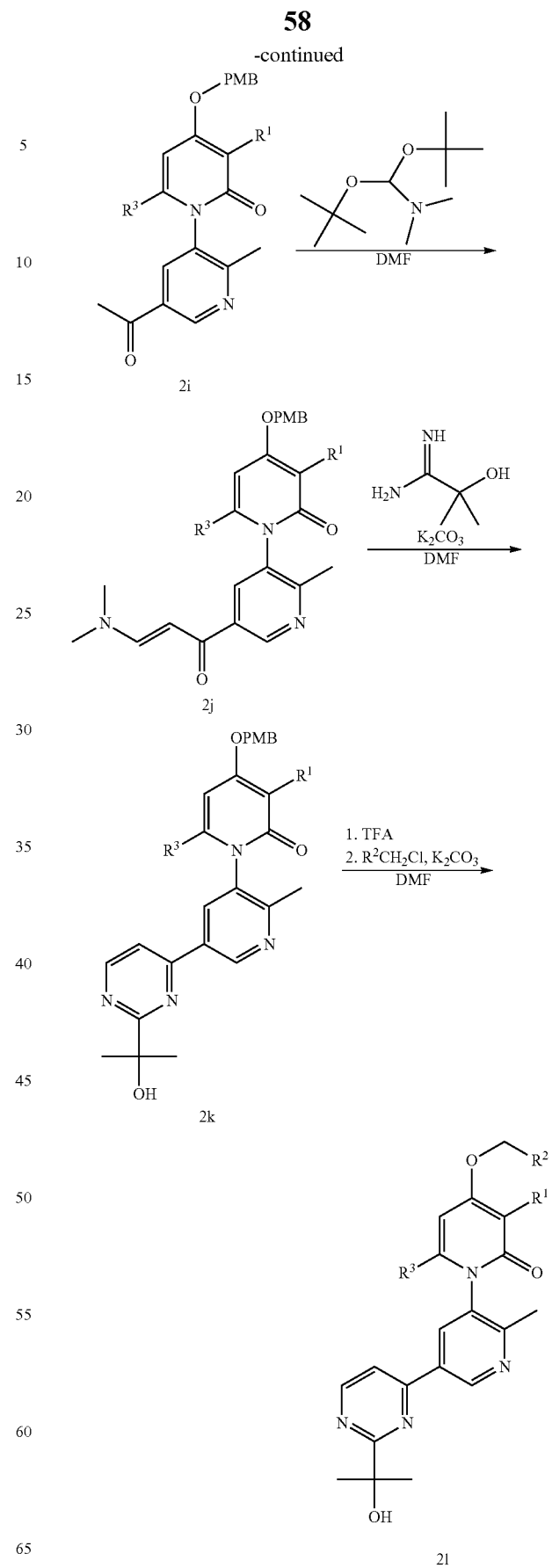

$R^1$ = chloro or bromo

An alternative procedure for preparing the compounds of invention is outlined in Scheme 2. The key amino-pyridine starting material 2d can be obtained from the appropriately substituted nitropyridine precursor by methylation, followed by carbonylation and reduction using stannous chloride. The pyridinone product 2e can be obtained by the reaction of 2d with the appropriately substituted 4-hydroxy pyrone derivative in solvents such as trifluroethanol or dichlorobenzene in the presence of lithium chloride.

Halogenations of 2d using reagents such as N-bromosuccinimide or N-chlorosuccinimide would generate the desired products represented by 2f. Elaboration of 2f to the final products represented by 2l can be achieved as described previously in scheme 1. The bromo intermediate represented by 2h ($R^1$=Br) can be used to introduce methyl or ethyl groups using bis-(triphenylphosphine)palladium (II) chloride and triethylamine (US 2005/0176775) in solvents such as DMF, DMA or acetonitrile.

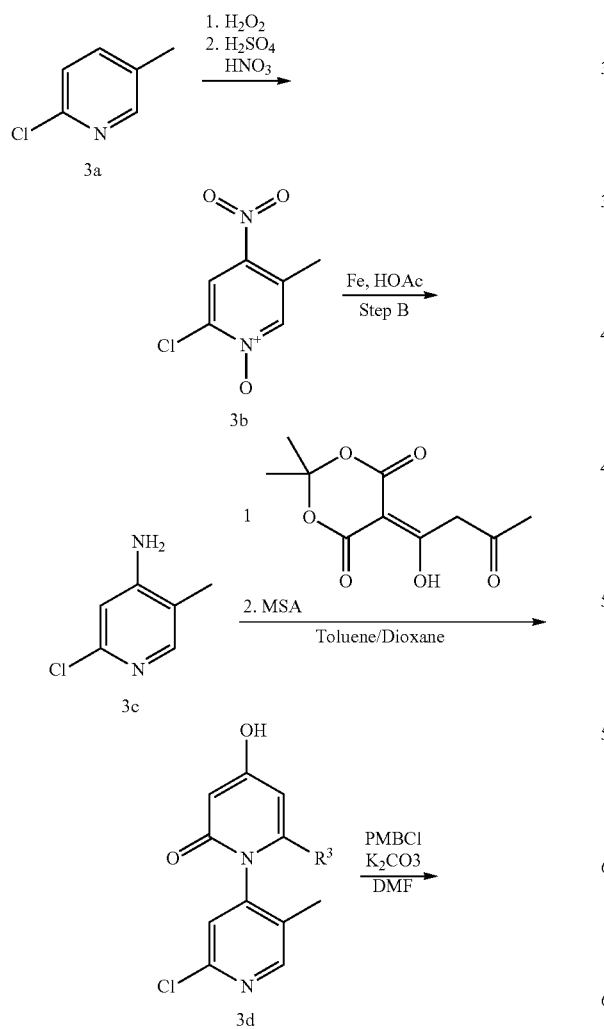

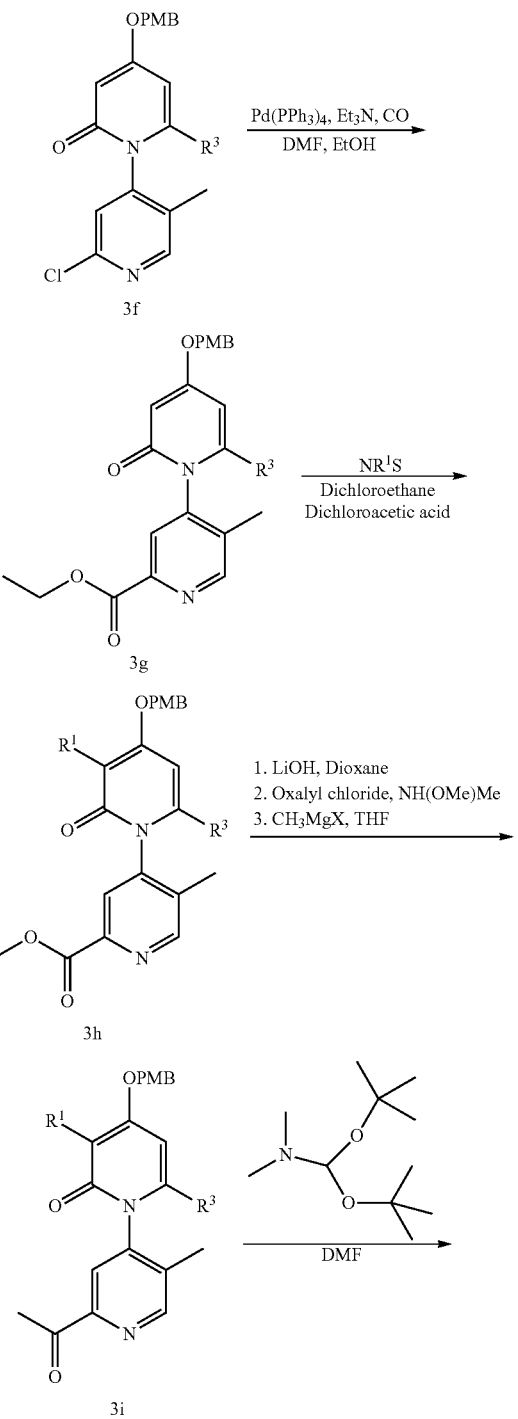

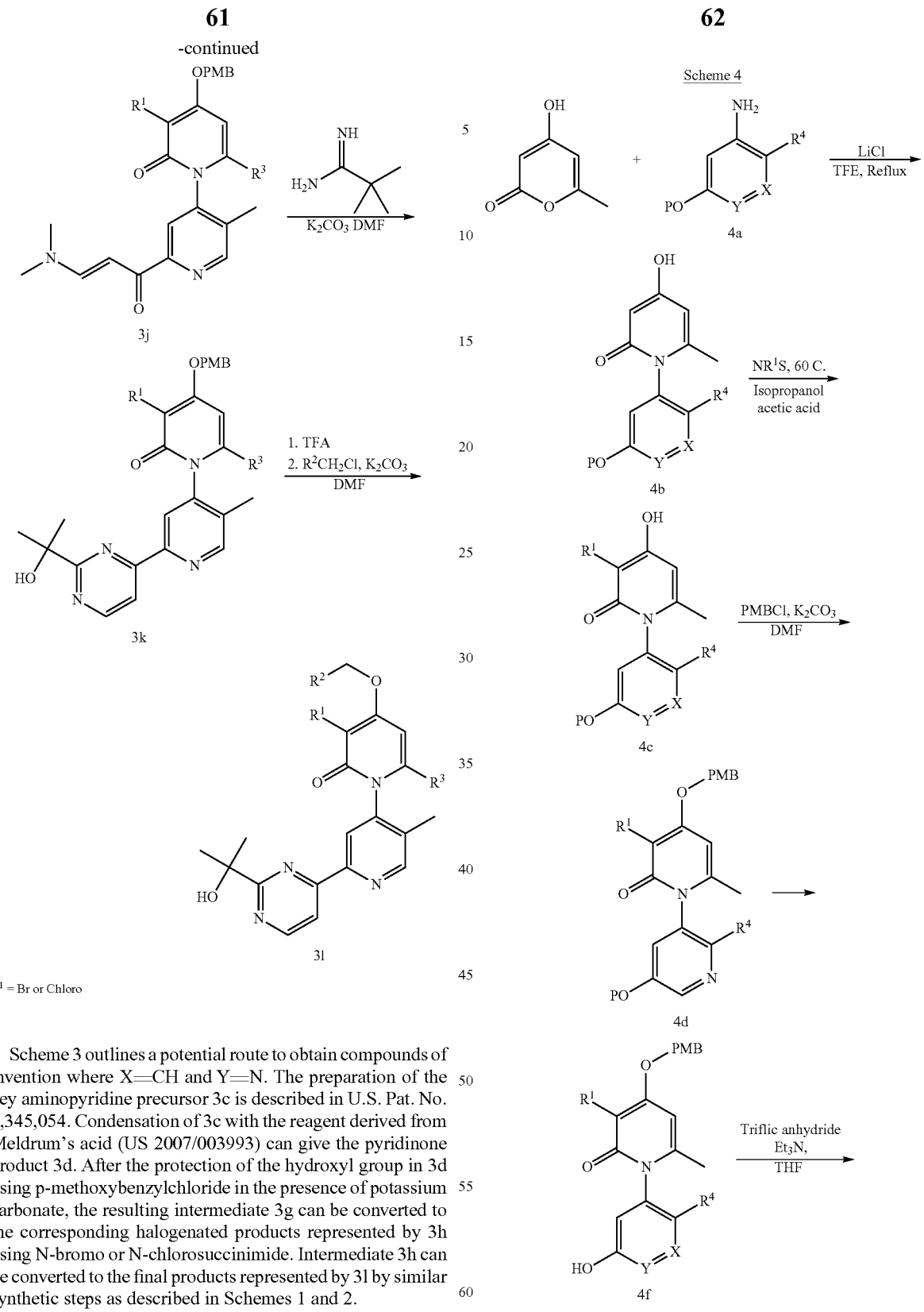

Scheme 3 outlines a potential route to obtain compounds of invention where X=CH and Y=N. The preparation of the key aminopyridine precursor 3c is described in U.S. Pat. No. 7,345,054. Condensation of 3c with the reagent derived from Meldrum's acid (US 2007/003993) can give the pyridinone product 3d. After the protection of the hydroxyl group in 3d using p-methoxybenzylchloride in the presence of potassium carbonate, the resulting intermediate 3g can be converted to the corresponding halogenated products represented by 3h using N-bromo or N-chlorosuccinimide. Intermediate 3h can be converted to the final products represented by 3l by similar synthetic steps as described in Schemes 1 and 2.

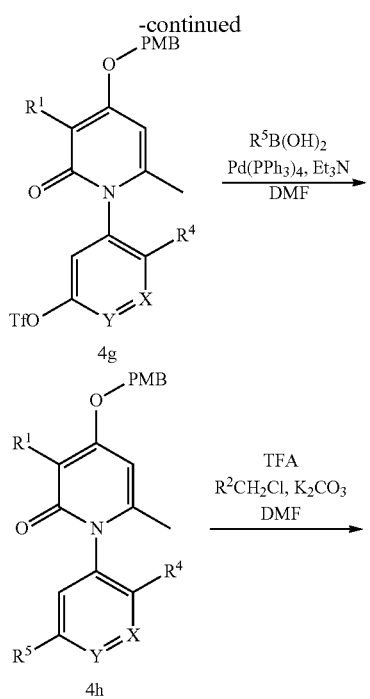

R⁴ = Me or H
R⁵ = Aryl OR Heteroaryl (Five & six membered)

Other appropriately substituted compounds of invention represented by 4i, with R⁵ as aryl or five/six-membered heterocyclic groups can be obtained as shown in Scheme 4, starting from 4-hydroxypyrone and a hydroxyl-protected (silyl, i.e., SEM or THP) aminopyridine 4a. Halogenation to give 4c can be achieved as described in earlier schemes, using N-chloro or N-bromosuccinimide. Benzyl ether formation followed by deprotection can generate the hydroxyl intermediate 4f. Triflate formation employing standard conditions can give 4g which upon palladium catalyzed cross-coupling reactions (Palladium in Heterocyclic chemistry by Jie Jack Li and Gordon W. Gribble) with a variety of aryl or heteroarylboronic acids, can give products represented by 4h. The final compounds of invention represented by 4i can be obtained by the removal p-methoxybenzyl followed by alkylation with appropriate heterocyclic methyl halides.

The racemic product may be separated using a chiral chromatography column such as Chiralcel OJ™ or Chiralpak® AD™ in a mobile phase of ethanol or methanol.

EXAMPLES

The following examples are merely illustrative, and do not limit this disclosure in any way.

Examples 1-567

Compounds 1-567, each corresponding to Examples 1-567, are prepared in accordance with Schemes I to IV above.

Examples 284 and 285

Preparation of Compound 284 (i.e., 3-chloro-4-((2,4-difluorobenzyl)oxy)-2'-(2-(2-hydroxypropan-2-yl)pyrimidin-4-yl)-5',6-dimethyl-2H-[1,4'-bipyridin]-2-one) and Compound 285 (i.e., 2'-[2-(tert-butyl)pyrimidin-4-yl]-3-chloro-4-((2,4-difluorobenzyl)oxy)-5',6-dimethyl-2H-[1,4'-bipyridin]-2-one) is described in the examples.

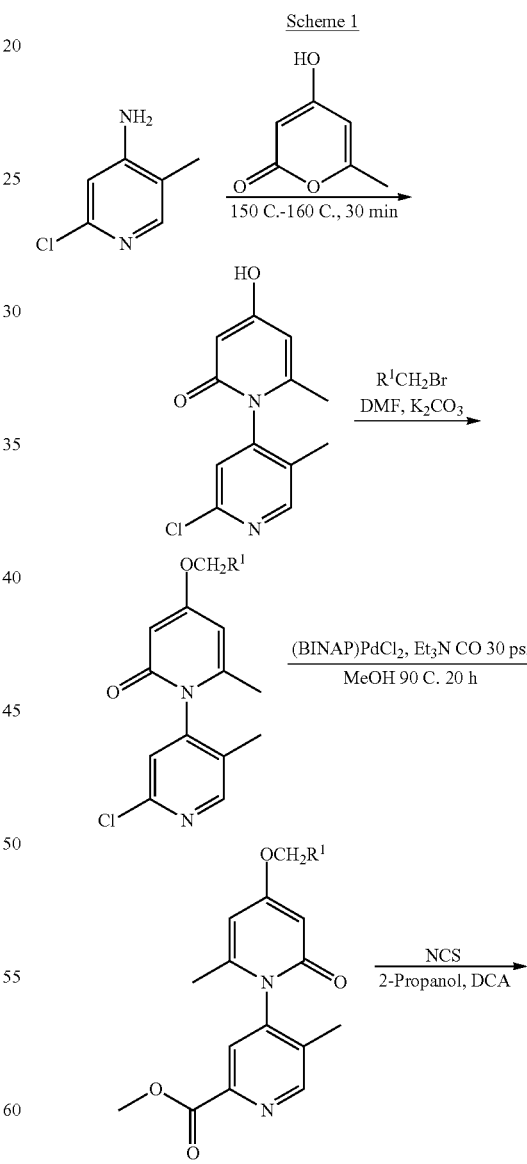

Scheme 1

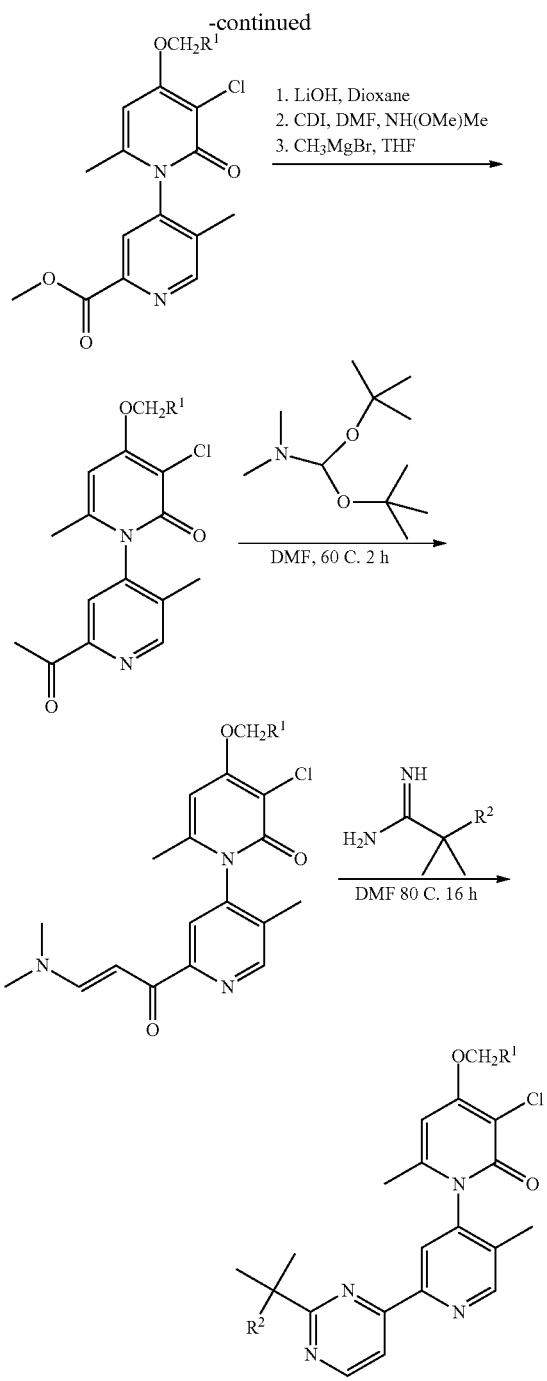

$R^1$ = 2,4-difluorophenyl
a. $R^2$ = OH
b. $R^2$ = Me

Step 1: Preparation of 2'-chloro-4-hydroxy-5',6-dimethyl-2H-1,4'-bipyridin-2-one. A well-powdered mixture of 4-amino-5-methyl-2-chloropyridine (0.5 g, 3.5 mmol), 4-hydroxy-6-methyl-pyrone (0.665 g, 5.3 mmol), and lithium chloride (0.025 g, 0.6 mmol) was heated at 160° C. for 20 min in a sealed tube. The resulting melt was cooled and the product was isolated by silica gel flash chromatography using 3% methanol in dichloromethane. Appropriate fractions were combined, concentrated under reduced pressure and the resulting solid was triturated with ethyl acetate, cooled and filtered. The solid was washed with ethyl acetate and dried to give 0.053 g of the title compound as a yellow powder. ES-MS: m/z=251 (M+H).

NMR $^1$H (300 MHz), CDCl$_3$ δ: 10.80 (br 1H), 8.47 (s, 1H), 7.56 (s, 1H), 5.97 (br, 1H), 5.57 (d, 1H, J=2.4 Hz), 1.96 (s, 3H), and 1.83 (s, 3H).

Step 2: Preparation of 2'-chloro-4-[(2,4-difluorobenzyl)oxy]-5',6-dimethyl-2H-1,4'-bipyridin-2-one. To a mixture of 2-choloro-4-hydroxy-5',6-dimethyl-2H-1-1,4-bipyridine-2-one (0.5 g, 0.6 mmol) and 2,4-diflurobenzyl bromide (0.14 g, 0.67 mmol) in dimethylformamide (3.0 mL), was added potassium carbonate (0.09 g, 0.65 mmol) and stirred at room temperature for 4 h. The reaction mixture was diluted with water and extracted with ethyl acetate (3×10 mL). The combined organic extracts were washed with water, dried (magnesium sulfate) and concentrated to dryness. The resulting material was purified by silica-gel flash chromatography using 35% heptane in ethyl acetate. Appropriate fractions were combined, and concentrated under reduced pressure to give 0.17 g of the title compound as an amorphous substance. ES-Ms, m/z=377 (M+H), 399 (M+Na).

NMR $^1$H (300 MHz), CDCl$_3$ δ: 8.43 (s, 1H), 7.41 (m, 1H), 7.16 (s, 1H), 6.95 (m, 2H), 5.96 (m, 2H), 5.04 (s, 2H), 2.11 (s, 3H), and 1.89 (s, 3H).

Step 3: Preparation of methyl 4-[(2,4-difluorobenzyl)oxy]-5',6-dimethyl-2-oxo-2H-1,4'-bipyridine-2'-carboxylate. To a solution of 2'-chloro-4-[(2,4-difluorobenzyl)oxy]-5',6-dimethyl-2H-1,4'-bipyridin-2-one (0.2 g, 0.53 mmol) in methanol (10.0 mL) in an autoclave vessel purged with nitrogen, was added (BINAP)PdCl$_2$ (0.021 g), followed by the addition of triethyl amine (0.079 g, 0.78 mmol). The vessel was pressurized with carbon monoxide up to 30 psi and heated at 100° C. for 16 h. The reaction mixture was cooled to room temperature, filtered through a celite pad and concentrated the filtrate to dryness. The residue was triturated with ethyl acetate and filtered. The filtrate was concentrated and the residue was purified by silica-gel flash chromatography using 3% methanol in ethyl acetate. Appropriate fractions were combined and concentrated under reduced pressure to give 0.15 g of the title compound. ES-MS, m/z=401 (M+H).

NMR $^1$H (300 MHz), CDCl$_3$ δ: 8.77 (s, 1H), 7.94 (s, 1H), 7.43 (m, 1H), 6.98 (m, 2H), 5.98 (2 s, 2H), 5.05 (s, 2H), 4.02 (s, 3H), 2.23 (s, 3H), and 1.86 (s, 3H).

Step 4: Preparation of methyl 3-chloro-4-[(2,4-difluorobenzyl)oxy]-5',6-dimethyl-2-oxo-2H-1,4'-bipyridine-2'-carboxylate. A mixture of methyl 4-[(2,4-difluorobenzyl)oxy]-5',6-dimethyl-2-oxo-2H-1,4'-bipyridine-2'-carboxylate (0.15 g, 0.375 mmol), N-chlorosuccinimide (0.06 g, 0.43 mmol) in 2-propanol (3.0 mL) containing dichloroacetic acid (0.05 mL) was heated at 60° C. under nitrogen for 2 h. The reaction mixture was concentrated, and the residue was purified by silica-gel flash chromatography using 4% methanol in ethyl acetate. Appropriate fractions were combined and concentrated under reduced pressure to give 0.15 g of the title compound. ES-MS, m/z=435 (M+H).

NMR $^1$H (300 MHz), CDCl$_3$ δ: 8.82 (s, 1H), 7.94 (s, 1H), 7.61 (m, 1H), 7.01 (m, 1H), 6.98 (m, 1H), 6.23 (s, 1H), 5.31 (s, 2H), 4.04 (s, 3H), 2.23 (s, 3H), and 1.97 (s, 3H).

Step 5: Preparation of 3-chloro-4-[(2,4-difluorobenzyl)oxy]-5',6-dimethyl-2-oxo-2H-1,4'-bipyridine-2'-carboxylic acid. A mixture of methyl 3-chloro-4-[(2,4-difluorobenzyl)oxy]-5',6-dimethyl-2-oxo-2H-1,4'-bipyridine-2'-carboxylate (0.13 g, 0.3 mmol) and 1.5 N NaOH (0.25 mL, 0.375 mmol) in dioxane (0.25 mL) was heated at 60° C. for 1 h and stirred at room temperature for an additional hr. The reaction mixture was acidified with acetic acid, and extracted with ethyl acetate (2×15 mL). The combined organic extract were washed with water and concentrated under reduced pressure to give the title compound as a white powder (0.08 g) which was used without purification in the next step. ES-MS, m/z=421 (M+H).

Step 6: Preparation of 3-chloro-4-[(2,4-difluorobenzyl)oxy]-5',6-dimethyl-2-oxo-2H-1,4'-bipyridine-2'-N-methoxymethyl amide. To a solution of 3-chloro-4-[(2,4-difluorobenzyl)oxy]-5',6-dimethyl-2-oxo-2H-1,4'-bipyridine-2'-carboxylic acid (0.08 g, 0.19 mmol) in dimethylformamide (1.0 mL) was added cabonyldiimidazole (0.05 g, 0.31 mmol) and stirred at room temperature. After 1.5 h, the mixture was cooled in an ice-bath, added N,O-dimethylhydroxylamine hydrochloride (0.03 g, 0.31 mmol), followed by the addition of triethyl amine (0.045 mL, 0.32 mmol). The resulting mixture was stirred at 5° C. for 30 min, and at room temperature for 2 h. At this stage, an additional 0.015 g of, N, O-dimethylhydroxylamine hydrochloride and triethyl amine (0.02 mL) were added and stirred overnight at room temperature. The reaction was quenched by the addition of ice-water (10 mL) and extracted with ethyl acetate (2×10 mL). The combined organic extracts were washed with water, and concentrated under reduced pressure to give the title compound as a white amorphous material (0.09 g) which was used without purification in the next step. ES-MS, m/z=464 (M+H).

Step 7: Preparation of 2'-acetyl-3-chloro-4-[(2,4-difluorobenzyl)oxy]-5',6-dimethyl-2H-1,4'-bipyridin-2-one. To a solution of 3-chloro-4-[(2,4-difluorobenzyl)oxy]-5',6-dimethyl-2-oxo-2H-1,4'-bipyridine-2'-N-methoxymethyl amide (0.09 g, 0.194 mmol) in tetrahydrofuran (2.0 mL) was added methylmagnesium bromide (0.08 mL, 3M, 0.24 mmol) and stirred at 0° C. After 1 h, added an additional 0.04 mL of methylmagnesium bromide and stirring was continued for an additional hr. The reaction was then quenched by the addition of cold saturated ammonium chloride (5 mL) and extracted with ethyl acetate (2×10 mL). The combined organic extracts was washed with water, dried with magnesium sulfate and concentrated. The resulting residue was purified by silica-gel flash chromatography using 5% heptane in ethyl acetate. Appropriate fractions were combined and concentrated under reduced pressure to give 0.055 g of the title compound. ES-MS, m/z=419 (M+H) and 441 (M+Na).

NMR $^1$H (300 MHz), CDCl$_3$ δ: 8.72 (s, 1H), 7.80 (s, 1H), 7.61 (m, 1H), 7.01 (m, 1H), 6.95 (m, 1H), 6.20 (s, 1H), 5.29 (s, 2H), 2.74 (s, 3H), 2.21 (s, 3H), and 1.94 (s, 3H).

Step 8: Preparation of 3-chloro-4-((2,4-difluorobenzyl)oxy)-2'-(2-(2-hydroxypropan-2-yl)pyrimidin-4-yl)-5',6-dimethyl-2H-[1,4'-bipyridin]-2-one (Example 284). To a solution of 2'-acetyl-3-chloro-4-[(2,4-difluorobenzyl)oxy]-5',6-dimethyl-2H-1,4'-bipyridin-2-one (0.045 g, 0.11 mmol) in DMF (0.5 mL) was added N, N dimethylformamide di-tert-butyl acetal (0.04 g, 0.2 mmol) and heated at 60° C. for 2 h. The reaction mixture was concentrated in vacuo, the residue was treated with toluene (1 mL) and concentrated in vacuo. The resulting residue was dried in vacuo for 2 h, dissolved in DMF (1 mL), and potassium carbonate (0.03 g, 0.22 mmol) and 2-hydroxy-2-methylpropiamidine hydrochloride (0.02 g, 0.14 mmol) were added. This mixture was heated at 80° C. for 12 h under nitrogen and concentrated in vacuo. The residue was partitioned between water (5 mL) and ethyl acetate (15 mL). The organic phase was washed with water, dried with magnesium sulfate, and concentrated. The resulting residue was purified by silica-gel flash chromatography using 3% methanol in ethyl acetate. Appropriate fractions were combined and concentrated under reduced pressure to give 0.022 g of the title compound. ES-MS, m/z=513 (M+H) and 535 (M+Na).

NMR $^1$H (300 MHz), CDCl$_3$ δ: 8.88 (d, 1H, J=5.1 Hz), 8.77 (s, 1H), 8.28 (d, 1H, J=5.1 Hz), 8.27 (s, 1H), 7.59 (m, 1H), 7.1 (m, 1H), 6.90 (m, 1H), 6.25 (s, 1H), 5.31 (s, 2H), 4.75 (s, 1H), 2.21 (s, 3H), 2.01 (s, 3H), 1.65 (s, 3H), and 1.64 (s, 3H).

Preparation of 2'-[2-(tert-butyl)pyrimidin-4-yl]-3-chloro-4-((2,4-difluorobenzyl)oxy)-5',6-dimethyl-2H-[1,4'-bipyridin]-2-one (Example 285). To a solution of 2'-acetyl-3-chloro-4-[(2,4-difluorobenzyl)oxy]-5',6-dimethyl-2H-1,4'-bipyridin-2-one (from step 7) (0.024 g, 0.057 mmol) in dimethylformamide (0.5 mL) was added N, N dimethylformamide di-tert-butyl acetal (0.02 g, 0.1 mmol) and heated at 60° C. for 2 h. The reaction mixture was concentrated in vacuo, the residue was dissolved in toluene (1 mL) and the solvent was removed in vacuo. The resulting residue was dried in vacuo for 2 h. It was dissolved in DMF (1 mL) and potassium carbonate (0.025 g, 0.18 mmol) and 2,2,2-trimethylacetamidine hydrochloride (0.02 g, 0.14 mmol) were added. This mixture was heated at 80 C. for 12 h under nitrogen. DMF was removed in vacuo and the residue was partitioned between water (5 mL) and ethyl acetate (15 mL). The organic phase was washed with water, dried with magnesium sulfate, and concentrated. The resulting residue was purified by silica-gel flash chromatography using 3% methanol in ethyl acetate. Appropriate fractions were combined and concentrated under reduced pressure to give 0.011 g of the title compound. ES-MS, m/z=511 (M+H).

Example 568

Biological Assays

P38 Inhibitory Potency and P38/MK2 Substrate Selectivity:

The novel, MK2 substrate-selective inhibitory mechanism of compounds is evaluated in enzyme assays comparing inhibitor potency in blocking p38/MK2 versus p38/PRAK induced phosphorylation of an HSP-27 derived peptide substrate. The ability of compounds to inhibit activated phospho-p38α is evaluated using a p38α/MK2 and a p38α/PRAK cascade assay format. The kinase activity of p38α is determined by its ability to phosphorylate GST-MK2 or GST-PRAK. Activation of MK2 or PRAK by p38α is quantitated by measuring the phosphorylation of a fluorescently-labeled, MK2 specific peptide substrate, Hsp27 peptide (FITC-KKKALSRQLSVAA). The phosphorylation of the Hsp27 peptide is quantified using the Caliper LabChip 3000. Kinase reactions is carried out in a 384-well plate (Matrical, MP101-1-PP) in 20 mM HEPES pH 7.5, 10 mM MgCl2, 0.0005% Tween-20, 0.01% BSA, 1 mM DTT, and 2% DMSO. The inhibitor concentration is varied between 0.02-30,000 nM, while the Hsp27 peptide substrate and MgATP are held constant at 1 µM and 10 µM, respectively. Activated p38α is added to a final concentration of 20 pM for reactions with nonphosphorylated 1 nM His6-MK2 in the cascade reaction. For the p38α/PRAK cascade, unactivated GST-PRAK is held constant at 1 nM while p38α is added in to a final concentration of 20 pM. Kinase reactions are incubated at room temperature and quenched after 30 minutes by the addition of stop buffer (180 mM HEPES, 30 mM EDTA, and 0.2% Coating Reagent-3). Under these conditions, approximately 20% of the substrate Hsp27 peptide is phosphorylated. Reactions are initiated by the addition of activated p38α except for preincubation experiments, where reactions are initiated by the addition of Hsp27 peptide and MgATP. Preincubation of p38α with inhibitor or p38α with unactivated His6-MK2 or unactivated GST-PRAK and inhibitor are performed at 2X final assay concentrations at room temperature 240 minutes prior to adding ATP and Hsp27 peptide to initiate catalysis. The p38α compound inhibitory potency is quantitated from dose-response IC50 values or Ki values from p38α/MK2 cascade assays while the substrate selectivity is calculated as a ratio of p38α/PRAK:p38α/MK2 IC50 values. Species compounds of Formula (I), described hereinabove, evaluated in this assay, are expected to provide a therapeutic benefit in the treatment of p38 kinase mediated diseases, such as autoimmune diseases and lymphoma.

Compounds were tested in accordance with the above described assay, yielding the IC50 values described below:

| Example | Structure | Name | MW | p38/MK2 IC$_{50}$ (µM) | p38/PRAK IC$_{50}$ (µM) |
|---------|-----------|------|----|------------------------|--------------------------|
| 284 | 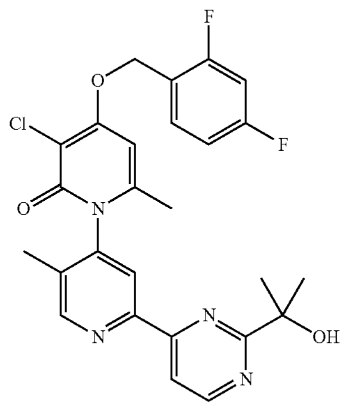 [SMILES: Cc1cnc(-c2ccnc(C(C)(C)O)n2)cc1-n1c(C)cc(OCc2ccc(F)cc2F)c(Cl)c1=O] | 3-chloro-4-((2,4-difluorobenzyl)oxy)-2'-(2-(2-hydroxypropan-2-yl)pyrimidin-4-yl)-5',6-dimethyl-2H-[1,4'-bipyridin]-2-one | 512 | 0.0064/ 0.0073 | 0.138/0.144 |
| 285 | 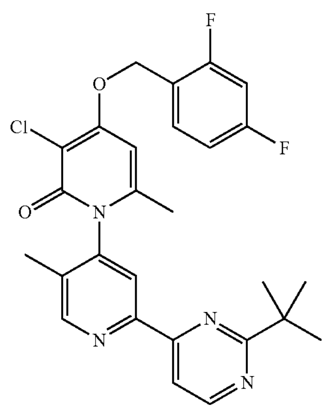 [SMILES: Cc1cnc(-c2ccnc(C(C)(C)C)n2)cc1-n1c(C)cc(OCc2ccc(F)cc2F)c(Cl)c1=O] | 2'-(2-(tert-butyl)pyrimidin-4-yl)-3-chloro-4-((2,4-difluorobenzyl)oxy)-5',6-dimethyl-2H-[1,4'-bipyridin]-2-one | 510 | 0.018/ 0.026 | 0.121/0.210 |

Cytokine Regulation in Human Monocytes:

The p38 pathway has been shown to be critical for the biosynthesis of a number of proinflammatory cytokines including TNFα, IL-1β and IL-6. Evaluation of the potency and efficacy of p38 inhibitors to block cytokine production is carried out using the human U937 cell line. The U937 human pre-monocytic cell line is obtained from the American Type Culture Collection (Rockville, Md.). These cells are differentiated to a monocytic/macrophage phenotype as described by Burnette (Burnette et al, (2009). SD0006: a potent, selective and orally available inhibitor of p38 kinase, *Pharmacology* 84(1):42-60). Differentiated U937 cells are seeded into 96-well tissue culture plates (200,000 cells/well) in complete media. After 24 hours, the cells are pretreated for 60 minutes in the presence or absence of compound and then stimulated with LPS (0.1 µg/mL) for 4 hours. Culture media are then collected for determination of TNFα, IL-6 or IL-1β levels by ELISA. Cytokine concentrations are extrapolated from recombinant protein standard curves using a four-parameter logistic model and solving for IC$_{50}$ after iterating to the best least-squares fit. Species compounds of Formula (I), described hereinabove, evaluated in this assay, are expected to provide a therapeutic benefit in the treatment of p38 kinase mediated diseases, such as lymphoma or inflammation.

IL1β Induced Prostaglandin Production in Rheumatoid Arthritis Synovial Fibroblasts (RASF):

Rheumatoid arthritis synovial fibroblasts (RASF) are derived from the inflamed synovium of a female RA patient who was undergoing total knee replacement. Synovial tissue is teased away from adjacent cartilage and dispersed into single cells with collagenase. Cells are expanded and banked. RASF cells are further cultured as described by Burnette supra. RASF cells are seeded into 96-well tissue culture plates (5×10$^4$ cells/well) in complete growth medium. After 24 hours, the medium is replaced with fresh growth medium containing 1% FBS. Cells are treated with serial concentrations (30,000-0.01 nM) of compound or dimethyl-sulfoxide (DMSO) vehicle control for 1 hour then stimulated with 1 ng/mL IL-1β (R&D Systems, Minneapolis, Minn.) for 18-20 hours at 37° C. and conditioned media collected. PGE$_2$ levels the in cultured media are quantitated by ELISA (Cayman Chemical, Ann Arbor, Mich.). Species compounds of Formula (I), described hereinabove, evaluated in this assay, are expected to provide a therapeutic benefit in the treatment of p38 kinase mediated diseases, such as lymphoma or rheumatoid arthritis.

Substrate Selectivity in HUVEC Cells:

When a compound is identified from the biochemical characterization step with selective inhibition of p38/MK2, it is next placed into a cell-based assay to verify enzyme to cell translatability. These assays utilize human umbilical vein endothelial cells (HUVEC) to demonstrate inhibition of Hsp27 phosphorylation (a biomarker of p38/MK2 activation) while sparing production of tissue factor (TF), which is linked to another downstream substrate of p38, MSK. In a 96-well format, adherent HUVEC (at 5 passages or less) are treated for 1 hour with serially-diluted compounds, including a non-selective p38 inhibitor as a reference, or vehicle for controls. For Hsp27 phosphorylation, cells are then stimulated with 500 pg/mL IL-1β for 0.5 hours, media is removed, cells are lysed, and phospho-Hsp27 in the lysate is quantitated by enzyme-linked immunosorbent assay (ELISA)(Life Technologies, Carlsbad, Calif.). The procedure for TF release is a similar ELISA-based assay (American Diagnostica, Stanford, Conn.), except that IL-1β stimulation proceeds for 5 hours. The ratio of TF inhibition IC50:HSP27 phosphorylation inhibition IC50 is defined as the substrate selectivity index in these cells. Species compounds of Formula (I), described hereinabove, evaluated in this assay, are expected to provide a therapeutic benefit in the treatment of p38 kinase mediated diseases, such as lymphoma and autoinflammatory disease.

Canine B Cell Growth Regulation:

p38 inhibitors have been shown to uniquely inhibit canine B cell proliferation and survival. This selective effect on canine B cells may be exploited in therapeutic treatment for canine B cell lymphoma, a fatal disease that impacts >40,000 companion animals in the United States. Quantitation of impact of p38 inhibitors on B cell growth is a cellular indicator of efficacy in B cell lymphoma. Species compounds of Formula (I), described hereinabove, evaluated in this assay, are expected to provide a therapeutic benefit in the treatment of p38 kinase mediated diseases, such as lymphoma. These assays utilize beagle dog spleens obtained with protocols approved by the Saint Louis University Animal Care and Use Committee in collaboration with Seventh Wave Laboratories. Leukocytes are isolated from splenocytes by centrifugation through Histopaque 1077. To evaluate effect on proliferation, leukocytes are then cultured for 48 hours in 96-well plates in the presence of vehicle or test compounds. Cells are stimulated with LPS for TLR4 stimulation, *Staphylococcus aureus* B cell mitogen, or concanavalin-A T cell mitogen, then proliferation is quantitated with a BRDU incorporation ELISA (Roche, Mannheim, Germany). For apoptosis experiments, leukocytes are plated on 96-well polypropylene U bottom plates and treated with p38 MAPK inhibitors or staurosporine (as a positive control) for up to 24 hours in the absence or presence of actinomycin D or cycloheximide (if needed to increase apoptosis rate). Apoptosis is determined using Caspase-Glo 3/7 luminescent assay (Promega, Madison, Wis.). In both assays, values generated after incubation with increasing concentrations of the inhibitors are compared to a negative control without inhibitors.

LPS Induced TNFα Production in Rats:

Rats are fasted eighteen hours prior to oral dosing, and allowed free access to water throughout the experiment. Each treatment group consists of five animals. Compounds are prepared as a suspension in a vehicle consisting of 0.5% methylcellulose, (Sigma Aldrich, St. Louis, Mo.), 0.025% Tween 20 (Sigma Aldrich). The compound or vehicle is administered by oral gavage in a volume of 1 mL. Two vehicle groups are used per experiment to control for intra-experiment variability. LPS (*E. coli* serotype 0111:B4, Sigma Aldrich) is administered four hours after compound intravenous injection at a dose of 1 mg/kg in 0.5 mL sterile saline (Baxter Healthcare, Deerfield, Ill.). Blood is collected in serum separator tubes via cardiac puncture ninety minutes after LPS injection, a time point corresponding to maximal TNFα and IL-1β production. After clotting, serum is withdrawn and stored at −20° C. and IL-1β and TNFα levels quantitated by ELISA (Burnette supra). Species compounds of Formula (I), described hereinabove, evaluated in this assay, are expected to provide a therapeutic benefit in the treatment of p38 kinase mediated diseases, such as lymphoma or inflammation.

All mentioned documents are incorporated by reference as if herein written. When introducing elements of the present invention or the exemplary embodiment(s) thereof, the articles "a," "an," "the" and "said" are intended to mean that there are one or more of the elements. The terms "comprising," "including" and "having" are intended to be inclusive and mean that there may be additional elements other than the listed elements. Although this invention has been described with respect to specific embodiments, the details of these embodiments are not to be construed as limitations.

What is claimed is:

1. A compound having the structure of Formula (I):

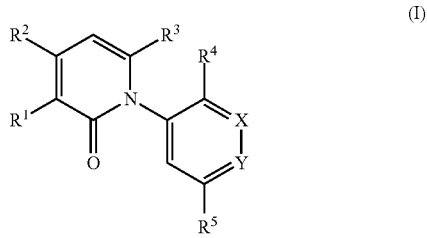

or a pharmaceutically acceptable salt thereof, wherein:
X and Y are independently selected from the group consisting of CH and N, with the proviso that when X is CH, Y is N, and when X is N, Y is CH;
$R^1$ is selected from the group consisting of $C_1$-$C_6$-alkyl, halo and —H;
$R^2$ is selected from the group consisting of alkyl and alkoxy; wherein the alkyl or alkoxy is optionally substituted with one or more substituents independently selected from the group consisting of cycloalkyl and aryl; and wherein the cycloalkyl or aryl is optionally substituted with one or more substituents independently selected from the group consisting of alkyl, alkoxy and halo;
$R^3$ and $R^4$ are independently selected from the group consisting of alkyl, halo and —H; and
$R^5$ is selected from the group consisting of cycloalkyl, aryl, and five- or six-membered heterocyclyl; wherein the cycloalkyl or aryl is optionally substituted with one or more substituents independently selected from the group consisting of halo, cyano, alkyl, hydroxyalkyl, alkoxyalkyl and aminoalkyl; and wherein the five- or six-membered heterocyclyl is optionally substituted with one or more substituents independently selected from the group consisting of cyano, alkyl, hydroxyalkyl, alkoxyalkyl and aminoalkyl.

2. The compound according to claim 1, wherein:
$R^1$ is selected from the group consisting of $C_1$-$C_3$-alkyl, bromo, chloro and fluoro;
$R^2$ is alkoxy, optionally substituted with one or more substituents selected from the group consisting of cycloalkyl and aryl; wherein the cycloalkyl or aryl is optionally substituted with one or more substituents independently selected from the group consisting of $C_1$-$C_3$-alkyl and halo;

$R^3$ and $R^4$ are independently $C_1$-$C_3$-alkyl, halo or —H; and $R^5$ is five- or six-membered heterocyclyl optionally substituted with one or more substituents independently selected from the group consisting of alkyl, hydroxyalkyl and aminoalkyl.

3. The compound according to claim 2, wherein:
$R^1$ is methyl, bromo or chloro;
$R^2$ is alkoxy optionally substituted with phenyl optionally substituted with one or more halo substituents;
$R^3$ is methyl;
$R^4$ is —H, chloro or methyl; and
$R^5$ is five- or six-membered heteroaryl optionally substituted with one or more substituents independently selected from the group consisting of alkyl and hydroxyalkyl.

4. The compound according to claim 3, wherein:
$R^2$ is alkoxy substituted with phenyl optionally substituted with one or more substituents independently selected from the group consisting of chloro and fluoro; and
$R^5$ is pyridinyl or pyrimidinyl, wherein the pyridinyl or pyrimidinyl is optionally substituted with one or more substituents independently selected from the group consisting of alkyl and hydroxyalkyl.

5. The compound according to claim 4, wherein the compound has the structure of Formula (IV):

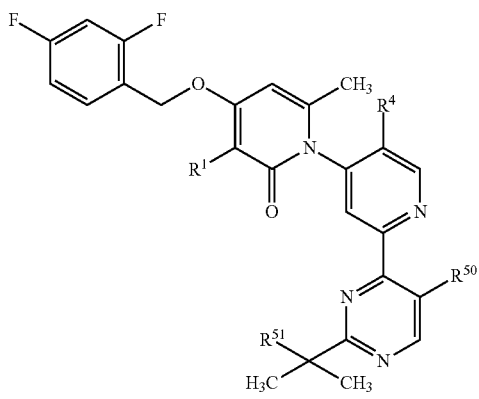

(IV)

wherein:
$R^1$ is methyl, bromo or chloro;
$R^4$ is —H, chloro or methyl;
$R^{50}$ is —H or methyl; and
$R^{51}$ is —H, methyl or hydroxy.

6. The compound according to claim 5, selected from the group consisting of:
 4-((2,4-difluorobenzyl)oxy)-2'-(2-(2-hydroxypropan-2-yl)pyrimidin-4-yl)-3',5',6-trimethyl-2H-[1,4'-bipyridin]-2-one;
 3-chloro-4-((2,4-difluorobenzyl)oxy)-2'-(2-(2-hydroxypropan-2-yl)pyrimidin-4-yl)-5',6-dimethyl-2H-[1,4'-bipyridin]-2-one;
 2'-(2-(tert-butyl)pyrimidin-4-yl)-3-chloro-4-((2,4-difluorobenzyl)oxy)-5',6-dimethyl-2H-[1,4'-bipyridin]-2-one;
 3-chloro-4-((2,4-difluorobenzyl)oxy)-2''-(2-hydroxypropan-2-yl)-5',6-dimethyl-2H-[1,4':2',4''-terpyridin]-2-one; and
 2''-(tert-butyl)-3-chloro-4-((2,4-difluorobenzyl)oxy)-6-methyl-2H-[1,4':2',4''-terpyridin]-2-one.

7. The compound according to claim 5, selected from the group consisting of:
 3-bromo-2'-(2-(tert-butyl)pyrimidin-4-yl)-4-((2,4-difluorobenzyl)oxy)-5',6-di methyl-2H-[1,4'-bipyridin]-2-one;
 2'-(2-(tert-butyl)pyrimidin-4-yl)-4-((2,4-difluorobenzyl)oxy)-3,5',6-trimethyl-2H-[1,4'-bipyridin]-2-one;
 3-bromo-2'-(2-(tert-butyl)pyrimidin-4-yl)-5'-chloro-4-((2,4-difluorobenzyl)oxy)-6-methyl-2H-[1,4'-bipyridin]-2-one;
 2'-(2-(tert-butyl)pyrimidin-4-yl)-3,5'-dichloro-4-((2,4-difluorobenzyl)oxy)-6-methyl-2H-[1,4'-bipyridin]-2-one;
 2'-(2-(tert-butyl)pyrimidin-4-yl)-5'-chloro-4-((2,4-difluorobenzyl)oxy)-3,6-dimethyl-2H-[1,4'-bipyridin]-2-one;
 3-bromo-2'-(2-(tert-butyl)pyrimidin-4-yl)-4-((2,4-difluorobenzyl)oxy)-6-methyl-2H-[1,4'-bipyridin]-2-one;
 2'-(2-(tert-butyl)pyrimidin-4-yl)-3-chloro-4-((2,4-difluorobenzyl)oxy)-6-methyl-2H-[1,4'-bipyridin]-2-one;
 2'-(2-(tert-butyl)pyrimidin-4-yl)-4-((2,4-difluorobenzyl)oxy)-3,6-dimethyl-2H-[1,4'-bipyridin]-2-one;
 3-bromo-2'-(2-(tert-butyl)-5-methylpyrimidin-4-yl)-4-((2,4-difluorobenzyl)oxy)-5',6-dimethyl-2H-[1,4'-bipyridin]-2-one;
 2'-(2-(tert-butyl)-5-methylpyrimidin-4-yl)-3-chloro-4-((2,4-difluorobenzyl)oxy)-5',6-dimethyl-2H-[1,4'-bipyridin]-2-one;
 2'-(2-(tert-butyl)-5-methylpyrimidin-4-yl)-4-((2,4-difluorobenzyl)oxy)-3',5',6-trimethyl-2H-[1,4'-bipyridin]-2-one;
 3-bromo-2'-(2-(tert-butyl)-5-methylpyrimidin-4-yl)-5'-chloro-4-((2,4-difluorobenzyl)oxy)-6-methyl-2H-[1,4'-bipyridin]-2-one;
 2'-(2-(tert-butyl)-5-methylpyrimidin-4-yl)-3,5'-dichloro-4-((2,4-difluorobenzyl)oxy)-6-methyl-2H-[1,4'-bipyridin]-2-one;
 2'-(2-(tert-butyl)-5-methylpyrimidin-4-yl)-5'-chloro-4-((2,4-difluorobenzyl)oxy)-3,6-dimethyl-2H-[1,4'-bipyridin]-2-one;
 3-bromo-2'-(2-(tert-butyl)-5-methylpyrimidin-4-yl)-4-((2,4-difluorobenzyl)oxy)-6-methyl-2H-[1,4'-bipyridin]-2-one;
 2'-(2-(tert-butyl)-5-methylpyrimidin-4-yl)-3-chloro-4-((2,4-difluorobenzyl)oxy)-6-methyl-2H-[1,4'-bipyridin]-2-one;
 2'-(2-(tert-butyl)-5-methylpyrimidin-4-yl)-4-((2,4-difluorobenzyl)oxy)-3,6-dimethyl-2H-[1,4'-bipyridin]-2-one;
 3-bromo-4-((2,4-difluorobenzyl)oxy)-2'-(2-isopropylpyrimidin-4-yl)-5',6-dimethyl-2H-[1,4'-bipyridin]-2-one;
 3-chloro-4-((2,4-difluorobenzyl)oxy)-2'-(2-isopropylpyrimidin-4-yl)-5',6-dimethyl-2H-[1,4'-bipyridin]-2-one;
 4-((2,4-difluorobenzyl)oxy)-2'-(2-isopropylpyrimidin-4-yl)-3,5',6-trimethyl-2H-[1,4'-bipyridin]-2-one;
 3-bromo-5'-chloro-4-((2,4-difluorobenzyl)oxy)-2'-(2-isopropylpyrimidin-4-yl)-6-methyl-2H-[1,4'-bipyridin]-2-one;
 3,5'-dichloro-4-((2,4-difluorobenzyl)oxy)-2'-(2-isopropylpyrimidin-4-yl)-6-methyl-2H-[1,4'-bipyridin]-2-one;
 5'-chloro-4-((2,4-difluorobenzyl)oxy)-2'-(2-isopropylpyrimidin-4-yl)-3,6-dimethyl-2H-[1,4'-bipyridin]-2-one;
 3-bromo-4-((2,4-difluorobenzyl)oxy)-2'-(2-isopropylpyrimidin-4-yl)-6-methyl-2H-[1,4'-bipyridin]-2-one;
 3-chloro-4-((2,4-difluorobenzyl)oxy)-2'-(2-isopropylpyrimidin-4-yl)-6-methyl-2H-[1,4'-bipyridin]-2-one;

4-((2,4-difluorobenzyl)oxy)-2'-(2-isopropylpyrimidin-4-yl)-3,6-dimethyl-2H-[1,4'-bipyridin]-2-one;

3-bromo-4-((2,4-difluorobenzyl)oxy)-2'-(2-isopropyl-5-methylpyrimidin-4-yl)-5',6-dimethyl-2H-[1,4'-bipyridin]-2-one;

3-chloro-4-((2,4-difluorobenzyl)oxy)-2'-(2-isopropyl-5-methylpyrimidin-4-yl)-5',6-dimethyl-2H-[1,4'-bipyridin]-2-one;

4-((2,4-difluorobenzyl)oxy)-2'-(2-isopropyl-5-methylpyrimidin-4-yl)-3,5',6-trimethyl-2H-[1,4'-bipyridin]-2-one;

3-bromo-5'-chloro-4-((2,4-difluorobenzyl)oxy)-2'-(2-isopropyl-5-methylpyrimidin-4-yl)-6-methyl-2H-[1,4'-bipyridin]-2-one;

3,5'-dichloro-4-((2,4-difluorobenzyl)oxy)-2'-(2-isopropyl-5-methylpyrimidin-4-yl)-6-methyl-2H-[1,4'-bipyridin]-2-one;

5'-chloro-4-((2,4-difluorobenzyl)oxy)-2'-(2-isopropyl-5-methylpyrimidin-4-yl)-3,6-dimethyl-2H-[1,4'-bipyridin]-2-one;

3-bromo-4-((2,4-difluorobenzyl)oxy)-2'-(2-isopropyl-5-methylpyrimidin-4-yl)-6-methyl-2H-[1,4'-bipyridin]-2-one;

3-chloro-4-((2,4-difluorobenzyl)oxy)-2'-(2-isopropyl-5-methylpyrimidin-4-yl)-6-methyl-2H-[1,4'-bipyridin]-2-one;

4-((2,4-difluorobenzyl)oxy)-2'-(2-isopropyl-5-methylpyrimidin-4-yl)-3,6-dimethyl-2H-[1,4'-bipyridin]-2-one;

3-bromo-4-((2,4-difluorobenzyl)oxy)-2'-(2-(2-hydroxypropan-2-yl)pyrimidin-4-yl)-5',6-dimethyl-2H-[1,4'-bipyridin]-2-one;

3-bromo-5'-chloro-4-((2,4-difluorobenzyl)oxy)-2'-(2-(2-hydroxypropan-2-yl)pyrimidin-4-yl)-6-methyl-2H-[1,4'-bipyridin]-2-one;

3,5'-dichloro-4-((2,4-difluorobenzyl)oxy)-2'-(2-(2-hydroxypropan-2-yl)pyrimidin-4-yl)-6-methyl-2H-[1,4'-bipyridin]-2-one;

5'-chloro-4-((2,4-difluorobenzyl)oxy)-2'-(2-(2-hydroxypropan-2-yl)pyrimidin-4-yl)-3,6-dimethyl-2H-[1,4'-bipyridin]-2-one;

3-bromo-4-((2,4-difluorobenzyl)oxy)-2'-(2-(2-hydroxypropan-2-yl)pyrimidin-4-yl)-6-methyl-2H-[1,4'-bipyridin]-2-one;

3-chloro-4-((2,4-difluorobenzyl)oxy)-2'-(2-(2-hydroxypropan-2-yl)pyrimidin-4-yl)-6-methyl-2H-[1,4'-bipyridin]-2-one;

4-((2,4-difluorobenzyl)oxy)-2'-(2-(2-hydroxypropan-2-yl)pyrimidin-4-yl)-3,6-dimethyl-2H-[1,4'-bipyridin]-2-one;

3-bromo-4-((2,4-difluorobenzyl)oxy)-2'-(2-(2-hydroxypropan-2-yl)-5-methylpyrimidin-4-yl)-5',6-dimethyl-2H-[1,4'-bipyridin]-2-one;

3-chloro-4-((2,4-difluorobenzyl)oxy)-2'-(2-(2-hydroxypropan-2-yl)-5-methylpyrimidin-4-yl)-5',6-dimethyl-2H-[1,4'-bipyridin]-2-one;

4-((2,4-difluorobenzyl)oxy)-2'-(2-(2-hydroxypropan-2-yl)-5-methylpyrimidin-4-yl)-3,5',6-trimethyl-2H-[1,4'-bipyridin]-2-one;

3-bromo-5'-chloro-4-((2,4-difluorobenzyl)oxy)-2'-(2-(2-hydroxypropan-2-yl)-5-methylpyrimidin-4-yl)-6-methyl-2H-[1,4'-bipyridin]-2-one;

3,5'-dichloro-4-((2,4-difluorobenzyl)oxy)-2'-(2-(2-hydroxypropan-2-yl)-5-methylpyrimidin-4-yl)-6-methyl-2H-[1,4'-bipyridin]-2-one;

5'-chloro-4-((2,4-difluorobenzyl)oxy)-2'-(2-(2-hydroxypropan-2-yl)-5-methylpyrimidin-4-yl)-3,6-dimethyl-2H-[1,4'-bipyridin]-2-one;

3-bromo-4-((2,4-difluorobenzyl)oxy)-2'-(2-(2-hydroxypropan-2-yl)-5-methylpyrimidin-4-yl)-6-methyl-2H-[1,4'-bipyridin]-2-one;

3-chloro-4-((2,4-difluorobenzyl)oxy)-2'-(2-(2-hydroxypropan-2-yl)-5-methylpyrimidin-4-yl)-6-methyl-2H-[1,4'-bipyridin]-2-one; and 4-((2,4-difluorobenzyl)oxy)-2'-(2-(2-hydroxypropan-2-yl)-5-methylpyrimidin-4-yl)-3,6-dimethyl-2H-[1,4'-bipyridin]-2-one.

8. The compound according to claim 1, wherein X is N and Y is CH.

9. The compound according to claim 8, wherein:
$R^1$ is selected from the group consisting of $C_1$-$C_3$-alkyl, bromo, chloro and fluoro;
$R^2$ is alkoxy optionally substituted with one or more substituents selected from the group consisting of cycloalkyl and aryl; wherein the cycloalkyl or aryl is optionally substituted with one or more substituents independently selected from the group consisting of $C_1$-$C_3$-alkyl and halo;
$R^3$ and $R^4$ are independently $C_1$-$C_3$-alkyl or —H; and
$R^5$ is five- or six-membered heterocyclyl optionally substituted with one or more substituents independently selected from the group consisting of alkyl, hydroxyalkyl and aminoalkyl.

10. The compound according to claim 9, wherein:
$R^1$ is methyl or chloro;
$R^2$ is alkoxy optionally substituted with phenyl optionally substituted with one or more halo substituents;
$R^3$ is methyl;
$R^4$ is —H or methyl; and
$R^5$ is five- or six-membered heteroaryl optionally substituted with one or more substituents independently selected from the group consisting of alkyl and hydroxyalkyl.

11. The compound according to claim 10, wherein:
$R^2$ is alkoxy substituted with phenyl optionally substituted with one or more substituents independently selected from the group consisting of chloro and fluoro; and
$R^5$ is pyridinyl or pyrimidinyl, wherein the pyridinyl or pyrimidinyl is optionally substituted with one or more substituents independently selected from the group consisting of alkyl and hydroxyalkyl.

12. The compound according to claim 11, wherein the compound has the structure of Formula (V):

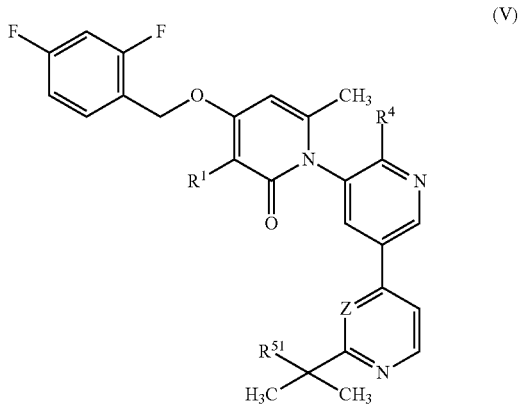

wherein:
Z is selected from the group consisting of CH and N;
$R^1$ is methyl or chloro;

R⁴ is —H or methyl; and
R⁵¹ is methyl or hydroxy.

13. The compound according to claim 12, selected from the group consisting of:
- 4-((2,4-difluorobenzyl)oxy)-5'-(2-(2-hydroxypropan-2-yl)pyrimidin-4-yl)-3,6-dimethyl-2H-[1,3'-bipyridin]-2-one;
- 4-((2,4-difluorobenzyl)oxy)-5'-(2-(2-hydroxypropan-2-yl)pyrimidin-4-yl)-2',3,6-trimethyl-2H-[1,3'-bipyridin]-2-one;
- 3-chloro-4-((2,4-difluorobenzyl)oxy)-5'-(2-(2-hydroxypropan-2-yl)pyrimidin-4-yl)-6-methyl-2H-[1,3'-bipyridin]-2-one;
- 3-chloro-4-((2,4-difluorobenzyl)oxy)-5'-(2-(2-hydroxypropan-2-yl)pyrimidin-4-yl)-2',6-dimethyl-2H-[1,3'-bipyridin]-2-one;
- 5'-(2-(tert-butyl)pyrimidin-4-yl)-3-chloro-4-((2,4-difluorobenzyl)oxy)-6-methyl-2H-[1,3'-bipyridin]-2-one;
- 5'-(2-(tert-butyl)pyrimidin-4-yl)-3-chloro-4-((2,4-difluorobenzyl)oxy)-2',6-dimethyl-2H-[1,3'-bipyridin]-2-one;
- 3-chloro-4-((2,4-difluorobenzyl)oxy)-2''-(2-hydroxypropan-2-yl)-6-methyl-2H-[1,3':5',4''-terpyridin]-2-one;
- 3-chloro-4-((2,4-difluorobenzyl)oxy)-2''-(2-hydroxypropan-2-yl)-2',6-dimethyl-2H-[1,3':5',4''-terpyridin]-2-one;
- 2''-(tert-butyl)-3-chloro-4-((2,4-difluorobenzyl)oxy)-6-methyl-2H-[1,3':5',4''-terpyridin]-2-one; and
- 2''-(tert-butyl)-3-chloro-4-((2,4-difluorobenzyl)oxy)-2',6-dimethyl-2H-[1,3':5',4''-terpyridin]-2-one.

14. The compound according to claim 1, wherein:
X and Y are independently selected from the group consisting of CH and N, with the proviso that when X is CH, Y is N, and when X is N, Y is CH;
R¹ is selected from the group consisting of $C_1$-$C_3$-alkyl, bromo, chloro and fluoro;
R² is alkoxy, optionally substituted with one or more substituents selected from the group consisting of cycloalkyl and aryl; wherein the cycloalkyl or aryl is optionally substituted with one or more substituents independently selected from the group consisting of $C_1$-$C_3$-alkyl and halo;
R³ and R⁴ are independently $C_1$-$C_3$-alkyl, halo or —H; and
R⁵ is five- or six-membered heterocyclyl optionally substituted with one or more substituents independently selected from the group consisting of alkyl, hydroxyalkyl and aminoalkyl.

15. The compound according to claim 14, wherein:
R¹ is methyl, bromo or chloro;
R² is alkoxy optionally substituted with phenyl optionally substituted with one or more halo substituents;
R³ is methyl;
R⁴ is —H, chloro or methyl; and
R⁵ is five- or six-membered heteroaryl optionally substituted with one or more substituents independently selected from the group consisting of alkyl and hydroxyalkyl.

16. The compound according to claim 15, wherein:
R² is alkoxy substituted with phenyl optionally substituted with one or more substituents independently selected from the group consisting of chloro and fluoro; and
R⁵ is pyridinyl or pyrimidinyl, wherein the pyridinyl or pyrimidinyl is optionally substituted with one or more substituents independently selected from the group consisting of alkyl and hydroxyalkyl.

17. The compound according to claim 16, wherein the compound has the structure of Formula (VI):

(VI)

wherein:
X and Y are independently selected from the group consisting of CH and N, with the proviso that when X is CH, Y is N, and when X is N, Y is CH;
R¹ is methyl, bromo or chloro;
R⁴ is —H, chloro or methyl;
R⁵⁰ is —H or methyl; and
R⁵¹ is —H, methyl or hydroxy.

18. The compound according to claim 17, selected from the group consisting of:
- 3-bromo-2'-(2-(tert-butyl)pyrimidin-4-yl)-4-((4-fluorobenzyl)oxy)-5',6-dimethyl-2H-[1,4'-bipyridin]-2-one;
- 2'-(2-(tert-butyl)pyrimidin-4-yl)-3-chloro-4-((4-fluorobenzyl)oxy)-5',6-dimethyl-2H-[1,4'-bipyridin]-2-one;
- 2'-(2-(tert-butyl)pyrimidin-4-yl)-4-((4-fluorobenzyl)oxy)-3,5',6-trimethyl-2H-[1,4'-bipyridin]-2-one;
- 3-bromo-2'-(2-(tert-butyl)pyrimidin-4-yl)-5'-chloro-4-((4-fluorobenzyl)oxy)-6-methyl-2H-[1,4'-bipyridin]-2-one;
- 2'-(2-(tert-butyl)pyrimidin-4-yl)-3,5'-dichloro-4-((4-fluorobenzyl)oxy)-6-methyl-2H-[1,4'-bipyridin]-2-one;
- 2'-(2-(tert-butyl)pyrimidin-4-yl)-5'-chloro-4-((4-fluorobenzyl)oxy)-3,6-dimethyl-2H-[1,4'-bipyridin]-2-one;
- 3-bromo-2'-(2-(tert-butyl)pyrimidin-4-yl)-4-((4-fluorobenzyl)oxy)-6-methyl-2H-[1,4'-bipyridin]-2-one;
- 2'-(2-(tert-butyl)pyrimidin-4-yl)-3-chloro-4-((4-fluorobenzyl)oxy)-6-methyl-2H-[1,4'-bipyridin]-2-one;
- 2'-(2-(tert-butyl)pyrimidin-4-yl)-4-((4-fluorobenzyl)oxy)-3,6-dimethyl-2H-[1,4'-bipyridin]-2-one;
- 3-bromo-2'-(2-(tert-butyl)-5-methylpyrimidin-4-yl)-4-((4-fluorobenzyl)oxy)-5',6-dimethyl-2H-[1,4'-bipyridin]-2-one;
- 2'-(2-(tert-butyl)-5-methylpyrimidin-4-yl)-3-chloro-4-((4-fluorobenzyl)oxy)-5',6-dimethyl-2H-[1,4'-bipyridin]-2-one;
- 2'-(2-(tert-butyl)-5-methylpyrimidin-4-yl)-4-((4-fluorobenzyl)oxy)-3,5',6-trimethyl-2H-[1,4'-bipyridin]-2-one;
- 3-bromo-2'-(2-(tert-butyl)-5-methylpyrimidin-4-yl)-5'-chloro-4-((4-fluorobenzyl)oxy)-6-methyl-2H-[1,4'-bipyridin]-2-one;
- 2'-(2-(tert-butyl)-5-methylpyrimidin-4-yl)-3,5'-dichloro-4-((4-fluorobenzyl)oxy)-6-methyl-2H-[1,4'-bipyridin]-2-one;
- 2'-(2-(tert-butyl)-5-methylpyrimidin-4-yl)-5'-chloro-4-((4-fluorobenzyl)oxy)-3,6-dimethyl-2H-[1,4'-bipyridin]-2-one;

3-bromo-2'-(2-(tert-butyl)-5-methylpyrimidin-4-yl)-4-((4-fluorobenzyl)oxy)-6-methyl-2H-[1,4'-bipyridin]-2-one;

2'-(2-(tert-butyl)-5-methylpyrimidin-4-yl)-3-chloro-4-((4-fluorobenzyl)oxy)-6-methyl-2H-[1,4'-bipyridin]-2-one;

2'-(2-(tert-butyl)-5-methylpyrimidin-4-yl)-4-((4-fluorobenzyl)oxy)-3,6-dimethyl-2H-[1,4'-bipyridin]-2-one;

3-bromo-4-((4-fluorobenzyl)oxy)-2'-(2-isopropylpyrimidin-4-yl)-5',6-dimethyl-2H-[1,4'-bipyridin]-2-one;

3-chloro-4-((4-fluorobenzyl)oxy)-2'-(2-isopropylpyrimidin-4-yl)-5',6-dimethyl-2H-[1,4'-bipyridin]-2-one;

4-((4-fluorobenzyl)oxy)-2'-(2-isopropylpyrimidin-4-yl)-3,5',6-trimethyl-2H-[1,4'-bipyridin]-2-one;

3-bromo-5'-chloro-4-((4-fluorobenzyl)oxy)-2'-(2-isopropylpyrimidin-4-yl)-6-methyl-2H-[1,4'-bipyridin]-2-one;

3,5'-dichloro-4-((4-fluorobenzyl)oxy)-2'-(2-isopropylpyrimidin-4-yl)-6-methyl-2H-[1,4'-bipyridin]-2-one;

5'-chloro-4-((4-fluorobenzyl)oxy)-2'-(2-isopropylpyrimidin-4-yl)-3,6-dimethyl-2H-[1,4'-bipyridin]-2-one;

3-bromo-4-((4-fluorobenzyl)oxy)-2'-(2-isopropylpyrimidin-4-yl)-6-methyl-2H-[1,4'-bipyridin]-2-one;

3-chloro-4-((4-fluorobenzyl)oxy)-2'-(2-isopropylpyrimidin-4-yl)-6-methyl-2H-[1,4'-bipyridin]-2-one;

4-((4-fluorobenzyl)oxy)-2'-(2-isopropylpyrimidin-4-yl)-3,6-dimethyl-2H-[1,4'-bipyridin]-2-one;

3-bromo-4-((4-fluorobenzyl)oxy)-2'-(2-isopropyl-5-methylpyrimidin-4-yl)-5',6-dimethyl-2H-[1,4'-bipyridin]-2-one;

3-chloro-4-((4-fluorobenzyl)oxy)-2'-(2-isopropyl-5-methylpyrimidin-4-yl)-5',6-dimethyl-2H-[1,4'-bipyridin]-2-one;

4-((4-fluorobenzyl)oxy)-2'-(2-isopropyl-5-methylpyrimidin-4-yl)-3,5',6-trimethyl-2H-[1,4'-bipyridin]-2-one;

3-bromo-5'-chloro-4-((4-fluorobenzyl)oxy)-2'-(2-isopropyl-5-methylpyrimidin-4-yl)-6-methyl-2H-[1,4'-bipyridin]-2-one;

3,5'-dichloro-4-((4-fluorobenzyl)oxy)-2'-(2-isopropyl-5-methylpyrimidin-4-yl)-6-methyl-2H-[1,4'-bipyridin]-2-one;

5'-chloro-4-((4-fluorobenzyl)oxy)-2'-(2-isopropyl-5-methylpyrimidin-4-yl)-3,6-dimethyl-2H-[1,4'-bipyridin]-2-one;

3-bromo-4-((4-fluorobenzyl)oxy)-2'-(2-isopropyl-5-methylpyrimidin-4-yl)-6-methyl-2H-[1,4'-bipyridin]-2-one;

3-chloro-4-((4-fluorobenzyl)oxy)-2'-(2-isopropyl-5-methylpyrimidin-4-yl)-6-methyl-2H-[1,4'-bipyridin]-2-one;

4-((4-fluorobenzyl)oxy)-2'-(2-isopropyl-5-methylpyrimidin-4-yl)-3,6-dimethyl-2H-[1,4'-bipyridin]-2-one;

3-bromo-4-((4-fluorobenzyl)oxy)-2'-(2-(2-hydroxypropan-2-yl)pyrimidin-4-yl)-5',6-dimethyl-2H-[1,4'-bipyridin]-2-one;

3-chloro-4-((4-fluorobenzyl)oxy)-2'-(2-(2-hydroxypropan-2-yl)pyrimidin-4-yl)-5',6-dimethyl-2H-[1,4'-bipyridin]-2-one;

4-((4-fluorobenzyl)oxy)-2'-(2-(2-hydroxypropan-2-yl)pyrimidin-4-yl)-3,5',6-trimethyl-2H-[1,4'-bipyridin]-2-one;

3-bromo-5'-chloro-4-((4-fluorobenzyl)oxy)-2'-(2-(2-hydroxypropan-2-yl)pyrimidin-4-yl)-6-methyl-2H-[1,4'-bipyridin]-2-one;

3,5'-dichloro-4-((4-fluorobenzyl)oxy)-2'-(2-(2-hydroxypropan-2-yl)pyrimidin-4-yl)-6-methyl-2H-[1,4'-bipyridin]-2-one;

5'-chloro-4-((4-fluorobenzyl)oxy)-2'-(2-(2-hydroxypropan-2-yl)pyrimidin-4-yl)-3,6-dimethyl-2H-[1,4'-bipyridin]-2-one;

3-bromo-4-((4-fluorobenzyl)oxy)-2'-(2-(2-hydroxypropan-2-yl)pyrimidin-4-yl)-6-methyl-2H-[1,4'-bipyridin]-2-one;

3-chloro-4-((4-fluorobenzyl)oxy)-2'-(2-(2-hydroxypropan-2-yl)pyrimidin-4-yl)-6-methyl-2H-[1,4'-bipyridin]-2-one;

4-((4-fluorobenzyl)oxy)-2'-(2-(2-hydroxypropan-2-yl)pyrimidin-4-yl)-3,6-dimethyl-2H-[1,4'-bipyridin]-2-one;

3-bromo-4-((4-fluorobenzyl)oxy)-2'-(2-(2-hydroxypropan-2-yl)-5-methylpyrimidin-4-yl)-5',6-dimethyl-2H-[1,4'-bipyridin]-2-one;

3-chloro-4-((4-fluorobenzyl)oxy)-2'-(2-(2-hydroxypropan-2-yl)-5-methylpyrimidin-4-yl)-5',6-dimethyl-2H-[1,4'-bipyridin]-2-one;

4-((4-fluorobenzyl)oxy)-2'-(2-(2-hydroxypropan-2-yl)-5-methylpyrimidin-4-yl)-3,5',6-trimethyl-2H-[1,4'-bipyridin]-2-one;

3-bromo-5'-chloro-4-((4-fluorobenzyl)oxy)-2'-(2-(2-hydroxypropan-2-yl)-5-methylpyrimidin-4-yl)-6-methyl-2H-[1,4'-bipyridin]-2-one;

3,5'-dichloro-4-((4-fluorobenzyl)oxy)-2'-(2-(2-hydroxypropan-2-yl)-5-methylpyrimidin-4-yl)-6-methyl-2H-[1,4'-bipyridin]-2-one;

5'-chloro-4-((4-fluorobenzyl)oxy)-2'-(2-(2-hydroxypropan-2-yl)-5-methylpyrimidin-4-yl)-3,6-dimethyl-2H-[1,4'-bipyridin]-2-one;

3-bromo-4-((4-fluorobenzyl)oxy)-2'-(2-(2-hydroxypropan-2-yl)-5-methylpyrimidin-4-yl)-6-methyl-2H-[1,4'-bipyridin]-2-one;

3-chloro-4-((4-fluorobenzyl)oxy)-2'-(2-(2-hydroxypropan-2-yl)-5-methylpyrimidin-4-yl)-6-methyl-2H-[1,4'-bipyridin]-2-one; and 4-((4-fluorobenzyl)oxy)-2'-(2-(2-hydroxypropan-2-yl)-5-methylpyrimidin-4-yl)-3,6-dimethyl-2H-[1,4'-bipyridin]-2-one.

19. A compound according to claim 1, wherein:

X and Y are independently selected from the group consisting of CH and N, with the proviso that when X is CH, Y is N, and when X is N, Y is CH;

$R^1$ is selected from the group consisting of $C_1$-$C_3$-alkyl, bromo, chloro and fluoro;

$R^2$ is alkoxy, optionally substituted with one or more substituents selected from the group consisting of cycloalkyl and aryl; wherein the cycloalkyl or aryl is optionally substituted with one or more substituents independently selected from the group consisting of $C_1$-$C_3$-alkyl and $C_1$-$C_3$-alkoxy;

$R^3$ and $R^4$ are independently $C_1$-$C_3$-alkyl, halo or —H; and $R^5$ is five- or six-membered heterocyclyl optionally substituted with one or more substituents independently selected from the group consisting of alkyl, hydroxyalkyl and aminoalkyl.

20. The compound according to claim 19, wherein:

$R^1$ is methyl, bromo or chloro;

$R^2$ is alkoxy optionally substituted with phenyl optionally substituted with one or more substituents independently selected from the group consisting of $C_1$-$C_3$-alkyl and $C_1$-$C_3$-alkoxy;

$R^3$ is methyl;

$R^4$ is —H, chloro or methyl; and $R^5$ is five- or six-membered heteroaryl optionally substituted with one or more substituents independently selected from the group consisting of alkyl and hydroxyalkyl.

21. The compound according to claim 20, wherein:
R² is alkoxy substituted with phenyl optionally substituted with one or more substituents independently selected from the group consisting of C₁-C₃-alkyl and C₁-C₃-alkoxy; and
R⁵ is pyridinyl or pyrimidinyl, wherein the pyridinyl or pyrimidinyl is optionally substituted with one or more substituents independently selected from the group consisting of alkyl and hydroxyalkyl.

22. The compound according to claim 21, wherein the compound has the structure of Formula (VII):

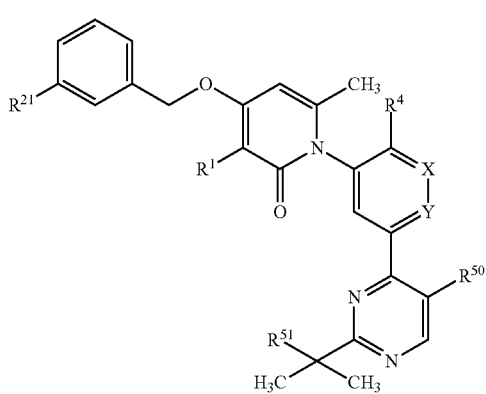

(VII)

wherein:
X and Y are independently selected from the group consisting of CH and N, with the proviso that when X is CH, Y is N, and when X is N, Y is CH;
R¹ is methyl, bromo or chloro;
R⁴ is —H, chloro or methyl;
R²¹ is methyl or methoxy;
R⁵⁰ is —H or methyl; and
R⁵¹ is —H, methyl or hydroxy.

23. The compound according to claim 22, selected from the group consisting of:
3-bromo-2'-(2-(tert-butyl)pyrimidin-4-yl)-5',6-dimethyl-4-((3-methylbenzyl)oxy)-2H-[1,4'-bipyridin]-2-one;
2'-(2-(tert-butyl)pyrimidin-4-yl)-3-chloro-5',6-dimethyl-4-((3-methylbenzyl)oxy)-2H-[1,4'-bipyridin]-2-one;
2'-(2-(tert-butyl)pyrimidin-4-yl)-3,5',6-trimethyl-4-((3-methylbenzyl)oxy)-2H-[1,4'-bipyridin]-2-one;
3-bromo-2'-(2-(tert-butyl)pyrimidin-4-yl)-5'-chloro-6-methyl-4-((3-methylbenzyl)oxy)-2H-[1,4'-bipyridin]-2-one;
2'-(2-(tert-butyl)pyrimidin-4-yl)-3,5'-dichloro-6-methyl-4-((3-methylbenzyl)oxy)-2H-[1,4'-bipyridin]-2-one;
2'-(2-(tert-butyl)pyrimidin-4-yl)-5'-chloro-3,6-dimethyl-4-((3-methylbenzyl)oxy)-2H-[1,4'-bipyridin]-2-one;
3-bromo-2'-(2-(tert-butyl)pyrimidin-4-yl)-6-methyl-4-((3-methylbenzyl)oxy)-2H-[1,4'-bipyridin]-2-one;
2'-(2-(tert-butyl)pyrimidin-4-yl)-3-chloro-6-methyl-4-((3-methylbenzyl)oxy)-2H-[1,4'-bipyridin]-2-one;
2'-(2-(tert-butyl)pyrimidin-4-yl)-3,6-dimethyl-4-((3-methylbenzyl)oxy)-2H-[1,4'-bipyridin]-2-one;
3-bromo-2'-(2-(tert-butyl)-5-methylpyrimidin-4-yl)-5',6-dimethyl-4-((3-methylbenzyl)oxy)-2H-[1,4'-bipyridin]-2-one;
2'-(2-(tert-butyl)-5-methylpyrimidin-4-yl)-3-chloro-5',6-dimethyl-4-((3-methylbenzyl)oxy)-2H-[1,4'-bipyridin]-2-one;
2'-(2-(tert-butyl)-5-methylpyrimidin-4-yl)-3,5',6-trimethyl-4-((3-methylbenzyl)oxy)-2H-[1,4'-bipyridin]-2-one;
3-bromo-2'-(2-(tert-butyl)-5-methylpyrimidin-4-yl)-5'-chloro-6-methyl-4-((3-methylbenzyl)oxy)-2H-[1,4'-bipyridin]-2-one;
2'-(2-(tert-butyl)-5-methylpyrimidin-4-yl)-3,5'-dichloro-6-methyl-4-((3-methylbenzyl)oxy)-2H-[1,4'-bipyridin]-2-one;
2'-(2-(tert-butyl)-5-methylpyrimidin-4-yl)-5'-chloro-3,6-dimethyl-4-((3-methylbenzyl)oxy)-2H-[1,4'-bipyridin]-2-one;
3-bromo-2'-(2-(tert-butyl)-5-methylpyrimidin-4-yl)-6-methyl-4-((3-methylbenzyl)oxy)-2H-[1,4'-bipyridin]-2-one;
2'-(2-(tert-butyl)-5-methylpyrimidin-4-yl)-3-chloro-6-methyl-4-((3-methylbenzyl)oxy)-2H-[1,4'-bipyridin]-2-one;
2'-(2-(tert-butyl)-5-methylpyrimidin-4-yl)-3,6-dimethyl-4-((3-methylbenzyl)oxy)-2H-[1,4'-bipyridin]-2-one;
3-bromo-2'-(2-isopropylpyrimidin-4-yl)-5',6-dimethyl-4-((3-methylbenzyl)oxy)-2H-[1,4'-bipyridin]-2-one;
3-chloro-2'-(2-isopropylpyrimidin-4-yl)-5',6-dimethyl-4-((3-methylbenzyl)oxy)-2H-[1,4'-bipyridin]-2-one;
2'-(2-isopropylpyrimidin-4-yl)-3,5',6-trimethyl-4-((3-methylbenzyl)oxy)-2H-[1,4'-bipyridin]-2-one;
3-bromo-5'-chloro-2'-(2-isopropylpyrimidin-4-yl)-6-methyl-4-((3-methylbenzyl)oxy)-2H-[1,4'-bipyridin]-2-one;
3,5'-dichloro-2'-(2-isopropylpyrimidin-4-yl)-6-methyl-4-((3-methylbenzyl)oxy)-2H-[1,4'-bipyridin]-2-one;
5'-chloro-2'-(2-isopropylpyrimidin-4-yl)-3,6-dimethyl-4-((3-methylbenzyl)oxy)-2H-[1,4'-bipyridin]-2-one;
3-bromo-2'-(2-isopropylpyrimidin-4-yl)-6-methyl-4-((3-methylbenzyl)oxy)-2H-[1,4'-bipyridin]-2-one;
3-chloro-2'-(2-isopropylpyrimidin-4-yl)-6-methyl-4-((3-methylbenzyl)oxy)-2H-[1,4'-bipyridin]-2-one;
2'-(2-isopropylpyrimidin-4-yl)-3,6-dimethyl-4-((3-methylbenzyl)oxy)-2H-[1,4'-bipyridin]-2-one;
3-bromo-2'-(2-isopropyl-5-methylpyrimidin-4-yl)-5',6-dimethyl-4-((3-methylbenzyl)oxy)-2H-[1,4'-bipyridin]-2-one;
3-chloro-2'-(2-isopropyl-5-methylpyrimidin-4-yl)-5',6-dimethyl-4-((3-methylbenzyl)oxy)-2H-[1,4'-bipyridin]-2-one;
2'-(2-isopropyl-5-methylpyrimidin-4-yl)-3,5',6-trimethyl-4-((3-methylbenzyl)oxy)-2H-[1,4'-bipyridin]-2-one;
3-bromo-5'-chloro-2'-(2-isopropyl-5-methylpyrimidin-4-yl)-6-methyl-4-((3-methylbenzyl)oxy)-2H-[1,4'-bipyridin]-2-one;
3,5'-dichloro-2'-(2-isopropyl-5-methylpyrimidin-4-yl)-6-methyl-4-((3-methylbenzyl)oxy)-2H-[1,4'-bipyridin]-2-one;
5'-chloro-2'-(2-isopropyl-5-methylpyrimidin-4-yl)-3,6-dimethyl-4-((3-methylbenzyl)oxy)-2H-[1,4'-bipyridin]-2-one;
3-bromo-2'-(2-isopropyl-5-methylpyrimidin-4-yl)-6-methyl-4-((3-methylbenzyl)oxy)-2H-[1,4'-bipyridin]-2-one;
3-chloro-2'-(2-isopropyl-5-methylpyrimidin-4-yl)-6-methyl-4-((3-methylbenzyl)oxy)-2H-[1,4'-bipyridin]-2-one;
2'-(2-isopropyl-5-methylpyrimidin-4-yl)-3,6-dimethyl-4-((3-methylbenzyl)oxy)-2H-[1,4'-bipyridin]-2-one;
3-bromo-2'-(2-(2-hydroxypropan-2-yl)pyrimidin-4-yl)-5',6-dimethyl-4-((3-methylbenzyl)oxy)-2H-[1,4'-bipyridin]-2-one;

3-chloro-2'-(2-(2-hydroxypropan-2-yl)pyrimidin-4-yl)-5',6-dimethyl-4-((3-methylbenzyl)oxy)-2H-[1,4'-bipyridin]-2-one;

2'-(2-(2-hydroxypropan-2-yl)pyrimidin-4-yl)-3,5',6-trimethyl-4-((3-methylbenzyl)oxy)-2H-[1,4'-bipyridin]-2-one;

3-bromo-5'-chloro-2'-(2-(2-hydroxypropan-2-yl)pyrimidin-4-yl)-6-methyl-4-((3-methylbenzyl)oxy)-2H-[1,4'-bipyridin]-2-one;

3,5'-dichloro-2'-(2-(2-hydroxypropan-2-yl)pyrimidin-4-yl)-6-methyl-4-((3-methylbenzyl)oxy)-2H-[1,4'-bipyridin]-2-one;

5'-chloro-2'-(2-(2-hydroxypropan-2-yl)pyrimidin-4-yl)-3,6-dimethyl-4-((3-methylbenzyl)oxy)-2H-[1,4'-bipyridin]-2-one;

3-bromo-2'-(2-(2-hydroxypropan-2-yl)pyrimidin-4-yl)-6-methyl-4-((3-methylbenzyl)oxy)-2H-[1,4'-bipyridin]-2-one;

3-chloro-2'-(2-(2-hydroxypropan-2-yl)pyrimidin-4-yl)-6-methyl-4-((3-methylbenzyl)oxy)-2H-[1,4'-bipyridin]-2-one;

2'-(2-(2-hydroxypropan-2-yl)pyrimidin-4-yl)-3,6-dimethyl-4-((3-methylbenzyl)oxy)-2H-[1,4'-bipyridin]-2-one;

3-bromo-2'-(2-(2-hydroxypropan-2-yl)-5-methylpyrimidin-4-yl)-5',6-dimethyl-4-((3-methylbenzyl)oxy)-2H-[1,4'-bipyridin]-2-one;

3-chloro-2'-(2-(2-hydroxypropan-2-yl)-5-methylpyrimidin-4-yl)-5',6-dimethyl-4-((3-methylbenzyl)oxy)-2H-[1,4'-bipyridin]-2-one;

2'-(2-(2-hydroxypropan-2-yl)-5-methylpyrimidin-4-yl)-3,5',6-trimethyl-4-((3-methylbenzyl)oxy)-2H-[1,4'-bipyridin]-2-one;

3-bromo-5'-chloro-2'-(2-(2-hydroxypropan-2-yl)-5-methylpyrimidin-4-yl)-6-methyl-4-((3-methylbenzyl)oxy)-2H-[1,4'-bipyridin]-2-one;

3,5'-dichloro-2'-(2-(2-hydroxypropan-2-yl)-5-methylpyrimidin-4-yl)-6-methyl-4-((3-methylbenzyl)oxy)-2H-[1,4'-bipyridin]-2-one;

5'-chloro-2'-(2-(2-hydroxypropan-2-yl)-5-methylpyrimidin-4-yl)-3,6-dimethyl-4-((3-methylbenzyl)oxy)-2H-[1,4'-bipyridin]-2-one;

3-bromo-2'-(2-(2-hydroxypropan-2-yl)-5-methylpyrimidin-4-yl)-6-methyl-4-((3-methylbenzyl)oxy)-2H-[1,4'-bipyridin]-2-one;

3-chloro-2'-(2-(2-hydroxypropan-2-yl)-5-methylpyrimidin-4-yl)-6-methyl-4-((3-methylbenzyl)oxy)-2H-[1,4'-bipyridin]-2-one; and 2'-(2-(2-hydroxypropan-2-yl)-5-methylpyrimidin-4-yl)-3,6-dimethyl-4-((3-methylbenzyl)oxy)-2H-[1,4'-bipyridin]-2-one.

24. The compound according to claim 23, selected from the group consisting of:

3-bromo-2'-(2-(tert-butyl)pyrimidin-4-yl)-4-((3-methoxybenzyl)oxy)-5',6-dimethyl-2H-[1,4'-bipyridin]-2-one;

2'-(2-(tert-butyl)pyrimidin-4-yl)-3-chloro-4-((3-methoxybenzyl)oxy)-5',6-dimethyl-2H-[1,4'-bipyridin]-2-one;

2'-(2-(tert-butyl)pyrimidin-4-yl)-4-((3-methoxybenzyl)oxy)-3,5',6-trimethyl-2H-[1,4'-bipyridin]-2-one;

3-bromo-2'-(2-(tert-butyl)pyrimidin-4-yl)-5'-chloro-4-((3-methoxybenzyl)oxy)-6-methyl-2H-[1,4'-bipyridin]-2-one;

2'-(2-(tert-butyl)pyrimidin-4-yl)-3,5'-dichloro-4-((3-methoxybenzyl)oxy)-6-methyl-2H-[1,4'-bipyridin]-2-one;

2'-(2-(tert-butyl)pyrimidin-4-yl)-5'-chloro-4-((3-methoxybenzyl)oxy)-3,6-dimethyl-2H-[1,4'-bipyridin]-2-one;

3-bromo-2'-(2-(tert-butyl)pyrimidin-4-yl)-4-((3-methoxybenzyl)oxy)-6-methyl-2H-[1,4'-bipyridin]-2-one;

2'-(2-(tert-butyl)pyrimidin-4-yl)-3-chloro-4-((3-methoxybenzyl)oxy)-6-methyl-2H-[1,4'-bipyridin]-2-one;

2'-(2-(tert-butyl)pyrimidin-4-yl)-4-((3-methoxybenzyl)oxy)-3,6-dimethyl-2H-[1,4'-bipyridin]-2-one;

3-bromo-2'-(2-(tert-butyl)-5-methylpyrimidin-4-yl)-4-((3-methoxybenzyl)oxy)-5',6-dimethyl-2H-[1,4'-bipyridin]-2-one;

2'-(2-(tert-butyl)-5-methylpyrimidin-4-yl)-3-chloro-4-((3-methoxybenzyl)oxy)-5',6-dimethyl-2H-[1,4'-bipyridin]-2-one;

2'-(2-(tert-butyl)-5-methylpyrimidin-4-yl)-4-((3-methoxybenzyl)oxy)-3,5',6-trimethyl-2H-[1,4'-bipyridin]-2-one;

3-bromo-2'-(2-(tert-butyl)-5-methylpyrimidin-4-yl)-5'-chloro-4-((3-methoxybenzyl)oxy)-6-methyl-2H-[1,4'-bipyridin]-2-one;

2'-(2-(tert-butyl)-5-methylpyrimidin-4-yl)-3,5'-dichloro-4-((3-methoxybenzyl)oxy)-6-methyl-2H-[1,4'-bipyridin]-2-one;

2'-(2-(tert-butyl)-5-methylpyrimidin-4-yl)-5'-chloro-4-((3-methoxybenzyl)oxy)-3,6-dimethyl-2H-[1,4'-bipyridin]-2-one;

3-bromo-2'-(2-(tert-butyl)-5-methylpyrimidin-4-yl)-4-((3-methoxybenzyl)oxy)-6-methyl-2H-[1,4'-bipyridin]-2-one;

2'-(2-(tert-butyl)-5-methylpyrimidin-4-yl)-3-chloro-4-((3-methoxybenzyl)oxy)-6-methyl-2H-[1,4'-bipyridin]-2-one;

2'-(2-(tert-butyl)-5-methylpyrimidin-4-yl)-4-((3-methoxybenzyl)oxy)-3,6-dimethyl-2H-[1,4'-bipyridin]-2-one;

3-bromo-2'-(2-isopropylpyrimidin-4-yl)-4-((3-methoxybenzyl)oxy)-5',6-dimethyl-2H-[1,4'-bipyridin]-2-one;

3-chloro-2'-(2-isopropylpyrimidin-4-yl)-4-((3-methoxybenzyl)oxy)-5',6-dimethyl-2H-[1,4'-bipyridin]-2-one;

2'-(2-isopropylpyrimidin-4-yl)-4-((3-methoxybenzyl)oxy)-3,5',6-trimethyl-2H-[1,4'-bipyridin]-2-one;

3-bromo-5'-chloro-2'-(2-isopropylpyrimidin-4-yl)-4-((3-methoxybenzyl)oxy)-6-methyl-2H-[1,4'-bipyridin]-2-one;

3,5'-dichloro-2'-(2-isopropylpyrimidin-4-yl)-4-((3-methoxybenzyl)oxy)-6-methyl-2H-[1,4'-bipyridin]-2-one;

5'-chloro-2'-(2-isopropylpyrimidin-4-yl)-4-((3-methoxybenzyl)oxy)-3,6-dimethyl-2H-[1,4'-bipyridin]-2-one;

3-bromo-2'-(2-isopropylpyrimidin-4-yl)-4-((3-methoxybenzyl)oxy)-6-methyl-2H-[1,4'-bipyridin]-2-one;

3-chloro-2'-(2-isopropylpyrimidin-4-yl)-4-((3-methoxybenzyl)oxy)-6-methyl-2H-[1,4'-bipyridin]-2-one;

2'-(2-isopropylpyrimidin-4-yl)-4-((3-methoxybenzyl)oxy)-3,6-dimethyl-2H-[1,4'-bipyridin]-2-one;

3-bromo-2'-(2-isopropyl-5-methylpyrimidin-4-yl)-4-((3-methoxybenzyl)oxy)-5',6-dimethyl-2H-[1,4'-bipyridin]-2-one;

3-chloro-2'-(2-isopropyl-5-methylpyrimidin-4-yl)-4-((3-methoxybenzyl)oxy)-5',6-dimethyl-2H-[1,4'-bipyridin]-2-one;

2'-(2-isopropyl-5-methylpyrimidin-4-yl)-4-((3-methoxybenzyl)oxy)-3,5',6-trimethyl-2H-[1,4'-bipyridin]-2-one;

3-bromo-5'-chloro-2'-(2-isopropyl-5-methylpyrimidin-4-yl)-4-((3-methoxybenzyl)oxy)-6-methyl-2H-[1,4'-bipyridin]-2-one;

3,5'-dichloro-2'-(2-isopropyl-5-methylpyrimidin-4-yl)-4-((3-methoxybenzyl)oxy)-6-methyl-2H-[1,4'-bipyridin]-2-one;

5'-chloro-2'-(2-isopropyl-5-methylpyrimidin-4-yl)-4-((3-methoxybenzyl)oxy)-3,6-dimethyl-2H-[1,4'-bipyridin]-2-one;

3-bromo-2'-(2-isopropyl-5-methylpyrimidin-4-yl)-4-((3-methoxybenzyl)oxy)-6-methyl-2H-[1,4'-bipyridin]-2-one;

3-chloro-2'-(2-isopropyl-5-methylpyrimidin-4-yl)-4-((3-methoxybenzyl)oxy)-6-methyl-2H-[1,4'-bipyridin]-2-one;

2'-(2-isopropyl-5-methylpyrimidin-4-yl)-4-((3-methoxybenzyl)oxy)-3,6-dimethyl-2H-[1,4'-bipyridin]-2-one;

3-bromo-2'-(2-(2-hydroxypropan-2-yl)pyrimidin-4-yl)-4-((3-methoxybenzyl)oxy)-5',6-dimethyl-2H-[1,4'-bipyridin]-2-one;

3-chloro-2'-(2-(2-hydroxypropan-2-yl)pyrimidin-4-yl)-4-((3-methoxybenzyl)oxy)-5',6-dimethyl-2H-[1,4'-bipyridin]-2-one;

2'-(2-(2-hydroxypropan-2-yl)pyrimidin-4-yl)-4-((3-methoxybenzyl)oxy)-3,5',6-trimethyl-2H-[1,4'-bipyridin]-2-one;

3-bromo-5'-chloro-2'-(2-(2-hydroxypropan-2-yl)pyrimidin-4-yl)-4-((3-methoxybenzyl)oxy)-6-methyl-2H-[1,4'-bipyridin]-2-one;

3,5'-dichloro-2'-(2-(2-hydroxypropan-2-yl)pyrimidin-4-yl)-4-((3-methoxybenzyl)oxy)-6-methyl-2H-[1,4'-bipyridin]-2-one;

5'-chloro-2'-(2-(2-hydroxypropan-2-yl)pyrimidin-4-yl)-4-((3-methoxybenzyl)oxy)-3,6-dimethyl-2H-[1,4'-bipyridin]-2-one;

3-bromo-2'-(2-(2-hydroxypropan-2-yl)pyrimidin-4-yl)-4-((3-methoxybenzyl)oxy)-6-methyl-2H-[1,4'-bipyridin]-2-one;

3-chloro-2'-(2-(2-hydroxypropan-2-yl)pyrimidin-4-yl)-4-((3-methoxybenzyl)oxy)-6-methyl-2H-[1,4'-bipyridin]-2-one;

2'-(2-(2-hydroxypropan-2-yl)pyrimidin-4-yl)-4-((3-methoxybenzyl)oxy)-3,6-dimethyl-2H-[1,4'-bipyridin]-2-one;

3-bromo-2'-(2-(2-hydroxypropan-2-yl)-5-methylpyrimidin-4-yl)-4-((3-methoxybenzyl)oxy)-5',6-dimethyl-2H-[1,4'-bipyridin]-2-one;

3-chloro-2'-(2-(2-hydroxypropan-2-yl)-5-methylpyrimidin-4-yl)-4-((3-methoxybenzyl)oxy)-5',6-dimethyl-2H-[1,4'-bipyridin]-2-one;

2'-(2-(2-hydroxypropan-2-yl)-5-methylpyrimidin-4-yl)-4-((3-methoxybenzyl)oxy)-3,5',6-trimethyl-2H-[1,4'-bipyridin]-2-one;

3-bromo-5'-chloro-2'-(2-(2-hydroxypropan-2-yl)-5-methylpyrimidin-4-yl)-4-((3-methoxybenzyl)oxy)-6-methyl-2H-[1,4'-bipyridin]-2-one;

3,5'-dichloro-2'-(2-(2-hydroxypropan-2-yl)-5-methylpyrimidin-4-yl)-4-((3-methoxybenzyl)oxy)-6-methyl-2H-[1,4'-bipyridin]-2-one;

5'-chloro-2'-(2-(2-hydroxypropan-2-yl)-5-methylpyrimidin-4-yl)-4-((3-methoxybenzyl)oxy)-3,6-dimethyl-2H-[1,4'-bipyridin]-2-one;

3-chloro-2'-(2-(2-hydroxypropan-2-yl)-5-methylpyrimidin-4-yl)-4-((3-methoxybenzyl)oxy)-6-methyl-2H-[1,4'-bipyridin]-2-one;

3-chloro-2'-(2-(2-hydroxypropan-2-yl)-5-methylpyrimidin-4-yl)-4-((3-methoxybenzyl)oxy)-6-methyl-2H-[1,4'-bipyridin]-2-one; and 2'-(2-(2-hydroxypropan-2-yl)-5-methylpyrimidin-4-yl)-4-((3-methoxybenzyl)oxy)-3,6-dimethyl-2H-[1,4'-bipyridin]-2-one.

25. A compound of 3-chloro-4-((2,4-difluorobenzyl)oxy)-2'-(2-(2-hydroxypropan-2-yl)pyrimidin-4-yl)-5',6-dimethyl-2H-[1,4'-bipyridin]-2-one, or a pharmaceutically acceptable salt thereof.

26. A pharmaceutical composition comprising a therapeutically effective amount of a compound of claim 1 or a pharmaceutically acceptable salt thereof, and a pharmaceutically acceptable carrier.

27. A method for treating lymphoma comprising administering to a subject in need thereof a therapeutically effective amount of a compound of claim 1 or pharmaceutically acceptable salt thereof.

28. The method of claim 27, wherein the subject is a mammal selected from a canine and a humane.

* * * * *